US006774105B1

(12) United States Patent
Bonadio et al.

(10) Patent No.: US 6,774,105 B1
(45) Date of Patent: Aug. 10, 2004

(54) METHODS OF USING LATENT TGF-β BINDING PROTEINS

(75) Inventors: Jeffrey Bonadio, San Diego, CA (US); Wushan Yin, Ann Arbor, MI (US)

(73) Assignee: The Regents of the University of Michigan, Ann Arbor, MI (US)

(*) Notice: Subject to any disclaimer, the term of this patent is extended or adjusted under 35 U.S.C. 154(b) by 0 days.

(21) Appl. No.: 09/592,685

(22) Filed: Jun. 12, 2000

Related U.S. Application Data

(63) Continuation-in-part of application No. 08/479,722, filed on Jun. 7, 1995, now Pat. No. 6,074,840, which is a continuation-in-part of application No. PCT/US95/02251, filed on Feb. 21, 1995, which is a continuation-in-part of application No. 08/316,650, filed on Sep. 30, 1994, now Pat. No. 5,942,496, which is a continuation-in-part of application No. 08/199,780, filed on Feb. 18, 1994, now Pat. No. 5,763,416.

(51) Int. Cl.[7] ............... G01N 33/53; C07K 14/495; C07K 14/435; A61K 38/17
(52) U.S. Cl. .................. 514/12; 530/350; 435/7.1
(58) Field of Search ................ 530/350; 514/12; 435/7.1

(56) References Cited

U.S. PATENT DOCUMENTS

| | | | |
|---|---|---|---|
| 4,137,921 A | 2/1979 | Okuzumi et al. ......... | 128/335.5 |
| 4,166,800 A | 9/1979 | Fong ......................... | 252/316 |
| 4,181,983 A | 1/1980 | Kulkarni .................... | 3/1 |
| 4,243,775 A | 1/1981 | Rosensaft et al. .......... | 525/415 |
| 4,279,249 A | 7/1981 | Vert et al. ................. | 128/92 D |
| 4,300,565 A | 11/1981 | Rosensaft et al. ........ | 128/335.5 |
| 4,347,234 A | 8/1982 | Wahlig et al. ............. | 424/15 |
| 4,384,975 A | 5/1983 | Fong ........................ | 427/213.36 |
| 4,390,519 A | 6/1983 | Sawyer ..................... | 424/28 |
| 4,409,332 A | 10/1983 | Jefferies et al. ........... | 435/188 |
| 4,455,256 A | 6/1984 | Urist ....................... | 260/112 R |
| 4,472,840 A | 9/1984 | Jefferies ................... | 3/1.9 |
| 4,530,449 A | 7/1985 | Nozawa et al. ........... | 623/16 |

(List continued on next page.)

FOREIGN PATENT DOCUMENTS

| | | |
|---|---|---|
| DE | 42 19 626 A1 | 12/1993 |
| EP | 0 614 974 A2 | 9/1994 |
| WO | WO 90/03733 | 4/1990 |
| WO | WO 90/11092 | 10/1990 |
| WO | WO 90/14074 | 11/1990 |
| WO | WO 91/17424 | 11/1991 |
| WO | WO 92/05199 | 4/1992 |
| WO | WO 92/07573 | 5/1992 |
| WO | WO 93/05751 | 4/1993 |
| WO | WO 93/09229 | 5/1993 |
| WO | WO 93/14778 | 8/1993 |
| WO | WO 93/15109 | 8/1993 |
| WO | WO 93/16739 | 9/1993 |
| WO | WO 94/01139 | 1/1994 |
| WO | WO 94/20615 | 9/1994 |

OTHER PUBLICATIONS

US 5,182,365, 1/1993, Opperman et al. (withdrawn)
Saharinen et al. Association of the small latent transforming growth factor–beta with an eight cysteine repeat of its binding protein LTBP–1. EMBO Journal, (Jan. 15, 1996) 15 (2) 245–53.*
Yin et al. Isolation of a novel latent transforming growth factor–beta binding protein gene (LTBP–3). J. Biol Chem. Apr. 1995 28;270(17):10147–60.*
Saharinen et al. Latent transforming growth factor–beta binding proteins (LTBPs)—structural extracellular matrix proteins for targeting TGF–beta action. Cytokine Growth Factor Rev. Jun. 1999; 10(2):99–117.*
Kanzaki et al. TGF–beta 1 binding protein: a component of the large latent complex of TGF–beta 1 with multiple repeat sequences. CELL, (Jun. 15, 1990) 61 (6) 1051–61.*
Ando, et al., "Localization of Transforming Growth Factor–β and Latent Transforming Growth Factor–β Binding Protein in Rat Kidney," *Kidney International* 47:733–739, 1995.
Chaudhry, et al., "Expression of Transforming Growth Factors Beta 1, Beta 2, Beta 3 in Neuroendocrine Tumors of the Digestive System," *Anticancer Res* 14(5B):2085–91, 1994 (Abstract).
Colosetti, et al., "Axotomy of Rat Facial Nerve Induces TGF–β and Latent TGF–β Binding Protein," *Brain Research Bulletin* 37(6):561–67, 1995.
Dallas, et al., "Characterization and Autoregulation of Latent Transforming Growth Factor β (TGFβ) Complexes in Osteoblast–like Cell Lines," *The Journal of Biological Chemistry*, 269(9):6815–22, 1994.
Eklöv, et al., "Lack of the Latent Transforming Growth Factor β Binding Protein in Malignant, but not Benigh Prostatic Tissue," *Cancer Research*, 53:3193–97, 1993.
Flaumenhaft, "Extracellular Regulation of Basic Fibroblast Growth Factor and Transforming Growth Factor–Beta Activity," *Dissertation Abstracts International*, 53(3):1340B, 1992. (abstract).
Kogawa et al., "[TGF–beta and Platelet]", *Rinsho Ketsueki*, 35(4):370–5, 1994 (abstract).
Koli, "Growth–Inhibitory Effects of Transforming Growth Factor–beta and 1,25–dihydroxyvitamin D(3) on Cultured Epithelial Cells: Relationships to Plasminogen Activation," *Diss. Abstr. Int,* 56(3):629, 1995.
Li, et al., "Mapping of Human and Murine Genes for Latent TGF–β Binding Protein–2 (LTBP2)," *Mammalian Genome* 6:42–45, 1995.
Maeda, et al., "Local Production and Localization of Transforming Growth Factor–beta in Tuberculous Pleurisy." *Clin. Exp. Immunol.,* 92:32–38, 1993.

(List continued on next page.)

Primary Examiner—David S. Romeo
(74) Attorney, Agent, or Firm—Williams, Morgan and Amerson

(57) ABSTRACT

Disclosed are novel nucleic acid and peptide compositions comprising latent TGFβ binding proteins (LTBPs). Also disclosed are methods of using LTBP-2 and LTBP-3 peptides and the DNA segments which encode them.

28 Claims, 8 Drawing Sheets

U.S. PATENT DOCUMENTS

| | | | |
|---|---|---|---|
| 4,538,603 A | 9/1985 | Pawelchak et al. | 128/156 |
| 4,539,981 A | 9/1985 | Tunc | 128/92 B |
| 4,563,350 A | 1/1986 | Nathan et al. | 424/95 |
| 4,563,489 A | 1/1986 | Urist | 524/21 |
| 4,568,559 A | 2/1986 | Nuwayser et al. | 427/3 |
| 4,578,384 A | 3/1986 | Hollinger | 514/8 |
| 4,585,797 A | 4/1986 | Cioca | 514/773 |
| 4,591,501 A | 5/1986 | Cioca | 424/28 |
| 4,596,574 A | 6/1986 | Urist | 623/16 |
| 4,619,989 A | 10/1986 | Urist | 530/417 |
| 4,623,588 A | 11/1986 | Nuwayser et al. | 428/402.24 |
| 4,703,108 A | 10/1987 | Silver et al. | 530/356 |
| 4,711,783 A | 12/1987 | Huc et al. | 424/460 |
| 4,741,337 A | 5/1988 | Smith et al. | 128/334 R |
| 4,744,365 A | 5/1988 | Kaplan et al. | 128/335.5 |
| 4,761,471 A | 8/1988 | Urist | 530/350 |
| 4,776,890 A | 10/1988 | Chu | 106/161 |
| 4,789,663 A | 12/1988 | Wallace et al. | 514/21 |
| 4,789,732 A | 12/1988 | Urtist | 530/350 |
| 4,795,804 A | 1/1989 | Urist | 530/350 |
| 4,798,786 A | 1/1989 | Tice et al. | 435/177 |
| 4,806,523 A | 2/1989 | Bentz et al. | 514/2 |
| 4,818,542 A | 4/1989 | DeLuca et al. | 424/491 |
| 4,833,125 A | 5/1989 | Neer et al. | 514/12 |
| 4,837,285 A | 6/1989 | Berg et al. | 530/356 |
| 4,839,130 A | 6/1989 | Kaplan et al. | 264/235 |
| 4,844,854 A | 7/1989 | Kaplan et al. | 264/235 |
| 4,865,846 A | 9/1989 | Kaufman | 424/428 |
| 4,877,864 A | 10/1989 | Wang et al. | 530/324 |
| 4,882,150 A | 11/1989 | Kaufman | 424/428 |
| 4,889,119 A | 12/1989 | Jamiolkowski et al. | 606/220 |
| 4,898,186 A | 2/1990 | Ikada et al. | 606/62 |
| 4,898,734 A | 2/1990 | Mathiowitz et al. | 424/426 |
| 4,902,508 A | 2/1990 | Badylak et al. | 424/95 |
| 4,916,193 A | 4/1990 | Tang et al. | 525/413 |
| 4,938,763 A | 7/1990 | Dunn et al. | 604/891.1 |
| 4,946,450 A | 8/1990 | Erwin | 604/294 |
| 4,952,402 A | 8/1990 | Sparks et al. | 424/419 |
| 4,956,178 A | 9/1990 | Badylak et al. | 424/551 |
| 4,957,902 A | 9/1990 | Grinnell | 514/17 |
| 4,961,707 A | 10/1990 | Magnusson et al. | 433/215 |
| 4,968,590 A | 11/1990 | Kuberasampath et al. | 530/326 |
| 4,975,526 A | 12/1990 | Kuberasampath et al. | 530/350 |
| 4,975,527 A | 12/1990 | Koezuka et al. | 530/356 |
| 4,988,358 A | 1/1991 | Eppley et al. | 623/16 |
| 5,001,169 A | 3/1991 | Nathan et al. | 523/113 |
| 5,004,602 A | 4/1991 | Hutchinson | 424/78 |
| 5,007,939 A | 4/1991 | Delcommune et al. | 623/66 |
| 5,011,691 A | 4/1991 | Oppermann et al. | 424/423 |
| 5,011,692 A | 4/1991 | Fujioka et al. | 424/426 |
| 5,013,649 A | 5/1991 | Wang et al. | 435/69.1 |
| 5,035,893 A | 7/1991 | Shioya et al. | 424/447 |
| 5,037,749 A | 8/1991 | Findlay | 435/176 |
| 5,039,660 A | 8/1991 | Leonard et al. | 514/8 |
| 5,051,272 A | 9/1991 | Hermes et al. | 427/2 |
| 5,059,123 A | 10/1991 | Jernberg | 433/215 |
| 5,077,049 A | 12/1991 | Dunn et al. | 424/426 |
| 5,080,665 A | 1/1992 | Jarrett et al. | 606/219 |
| 5,081,106 A | 1/1992 | Bentley et al. | 514/5 |
| 5,084,051 A | 1/1992 | Törmälä et al. | 606/77 |
| 5,103,840 A | 4/1992 | Kavoussi | 128/899 |
| 5,106,626 A | 4/1992 | Parsons et al. | 424/423 |
| 5,106,748 A | 4/1992 | Wozney et al. | 435/252.3 |
| 5,108,753 A | 4/1992 | Kuberasampath et al. | 424/422 |
| 5,108,755 A | 4/1992 | Daniels et al. | 424/426 |
| 5,108,922 A | 4/1992 | Wang et al. | 435/240.2 |
| 5,110,604 A | 5/1992 | Chu et al. | 424/484 |
| 5,116,738 A | 5/1992 | Wang et al. | 435/69.1 |
| 5,118,667 A | 6/1992 | Adams et al. | 514/12 |
| 5,120,322 A | 6/1992 | Davis et al. | 604/265 |
| 5,124,155 A | 6/1992 | Reich | 424/428 |
| 5,128,136 A | 7/1992 | Bentley et al. | 424/443 |
| 5,128,326 A | 7/1992 | Balazs et al. | 514/54 |
| 5,133,755 A | 7/1992 | Brekke | 623/16 |
| 5,137,669 A | 8/1992 | Leonard et al. | 264/120 |
| 5,141,905 A | 8/1992 | Rosen et al. | 435/69.1 |
| 5,143,730 A | 9/1992 | Fues et al. | 424/426 |
| 5,162,114 A | 11/1992 | Kuberasampath et al. | 424/423 |
| 5,162,430 A | 11/1992 | Rhee et al. | 525/54.1 |
| 5,164,368 A | 11/1992 | Recker | 514/12 |
| 5,166,058 A | 11/1992 | Wang et al. | 435/69.1 |
| 5,168,050 A | 12/1992 | Hammonds, Jr. et al. | 435/69.1 |
| 5,171,217 A | 12/1992 | March et al. | 604/53 |
| 5,171,574 A | 12/1992 | Kuberasampath et al. | 424/423 |
| 5,171,579 A | 12/1992 | Ron et al. | 424/486 |
| 5,171,670 A | 12/1992 | Kronenberg et al. | 435/68.1 |
| 5,185,152 A | 2/1993 | Peyman | 424/427 |
| 5,187,076 A | 2/1993 | Wozney et al. | 435/69.1 |
| 5,192,741 A | 3/1993 | Orsolini et al. | 514/4 |
| 5,196,185 A | 3/1993 | Silver et al. | 424/45 |
| 5,197,977 A | 3/1993 | Hoffman, Jr. et al. | 623/1 |
| 5,206,028 A | 4/1993 | Li | 424/484 |
| 5,208,041 A | 5/1993 | Sindrey | 424/562 |
| 5,208,219 A | 5/1993 | Ogawa et al. | 514/12 |
| 5,223,263 A | 6/1993 | Hostetler et al. | 424/450 |
| 5,227,157 A | 7/1993 | McGinity et al. | 424/78.02 |
| 5,229,495 A | 7/1993 | Ichijo et al. | |
| 5,250,302 A | 10/1993 | Oppermann et al. | 424/422 |
| 5,250,584 A | 10/1993 | Ikada et al. | 523/114 |
| 5,258,494 A | 11/1993 | Oppermann et al. | 530/326 |
| 5,263,985 A | 11/1993 | Bao et al. | 623/16 |
| 5,264,618 A | 11/1993 | Felgner et al. | 560/224 |
| 5,266,683 A | 11/1993 | Oppermann et al. | 530/326 |
| 5,268,178 A | 12/1993 | Calhoun et al. | 424/426 |
| 5,270,300 A | 12/1993 | Hunziker | 514/12 |
| 5,271,961 A | 12/1993 | Mathiowitz et al. | 427/213.31 |
| 5,273,964 A | 12/1993 | Lemons | 514/2 |
| 5,275,826 A | 1/1994 | Badylak et al. | 424/551 |
| 5,278,201 A | 1/1994 | Dunn et al. | 523/113 |
| 5,278,202 A | 1/1994 | Dunn et al. | 523/113 |
| 5,280,109 A | 1/1994 | Miyazono et al. | |
| 5,281,419 A | 1/1994 | Tuan et al. | 424/426 |
| 5,281,422 A | 1/1994 | Badylak et al. | 424/551 |
| 5,286,634 A | 2/1994 | Stadler et al. | 435/172.3 |
| 5,288,496 A | 2/1994 | Lewis | 424/426 |
| 5,292,802 A | 3/1994 | Rhee et al. | 525/54.1 |
| 5,306,303 A | 4/1994 | Lynch | 623/16 |
| 5,308,623 A | 5/1994 | Fues et al. | 424/426 |
| 5,308,889 A | 5/1994 | Rhee et al. | 523/113 |
| 5,317,010 A | 5/1994 | Pang et al. | 514/12 |
| 5,320,624 A | 6/1994 | Kaplan et al. | 606/77 |
| 5,324,307 A | 6/1994 | Jarrett et al. | 606/219 |
| 5,324,519 A | 6/1994 | Dunn et al. | 424/426 |
| 5,324,520 A | 6/1994 | Dunn et al. | 424/435 |
| 5,324,819 A | 6/1994 | Oppermann et al. | 530/350 |
| 5,326,350 A | 7/1994 | Li | 623/11 |
| 5,326,357 A | 7/1994 | Kandel | 623/16 |
| 5,328,955 A | 7/1994 | Rhee et al. | 525/54.1 |
| 5,344,654 A | 9/1994 | Rueger et al. | 424/423 |
| 5,346,993 A | 9/1994 | Miyazono et al. | |
| 5,350,580 A | 9/1994 | Muchow et al. | 424/437 |
| 5,352,463 A | 10/1994 | Badylak et al. | 424/551 |
| 5,354,557 A | 10/1994 | Oppermann et al. | 424/423 |
| 5,360,610 A | 11/1994 | Tice et al. | 424/426 |
| 5,366,508 A | 11/1994 | Brekke | 623/16 |
| 5,366,733 A | 11/1994 | Brizzolara et al. | 424/426 |
| 5,366,734 A | 11/1994 | Hutchinson | 424/426 |
| 5,366,875 A | 11/1994 | Wozney et al. | 435/69.1 |
| 5,372,821 A | 12/1994 | Badylak et al. | 424/551 |
| 5,445,833 A | 8/1995 | Badylak et al. | 424/551 |
| 5,656,450 A | 8/1997 | Boyan et al. | 435/68.1 |

6,074,840 A    6/2000  Bonadio et al. ............ 435/69.1

OTHER PUBLICATIONS

Miyazono, et al., "Structure and Function of Latent Forms of Transforming Growth Factor–beta (Meeting abstract)," *Seventh International Conference of the International Society of Differentiation, Cellular Programmes for Growth Differentiation and Neoplasia.* (1992):58. 1992.

Mizoi, et al. "Immunohistochemical Identification of Transforming Growth Factor–beta and Its Binding Protein in Human Gastrointestinal Carcinoma," *Tojoku J. Exp. Med.,* 168(2):271–3. 1992. (abstract).

Mizoi, et al., "Immunoelectron Microscopic Localization of Transforming Growth Factor $_1$ and Latent Transforming Growth Factor $\beta_1$ Binding Protein in Human Gastrointestinal Carcinomas: Qualitative Difference Between Cancer Cells and Stromal Cells," *Cancer Research,* 53:183–190, 1993.

Rifkin, "TGF–β Formation; Mechanisms and Consequences," *J. Cellular Biochem.* Suppl. 19B, 3, 1995.

Taipale, et al., "Control of TGF–beta 1, Its Latent Form Binding Protein (LTBP) and Typ0e II Receptor Expression During Differentiation of Human Myeloid Leukemia Cells Lines (Meeting Abstract)," *EACR–12: 12th Biennial Meeting of the European Association for Cancer Research,* 1993.

Tamaki et al., "TGF–β1 in Glomerulosclerosis and Interstitial Fibrosis of Adriamycin Nephropathy," *Kidney International,* 45:525–36, 1994.

Van Laethem, et al., "Localization of Transforming Growth Factor β1 and Its Latent Binding Protein in Human Chronic Pancreatitis," *Gastroenterology* 108:1873–81, 1995.

Vilafranca, et al., "Muscle Fibre Expression of Transforming Growth Factor–beta 1 and Latent Transforming Growth Factor–beta Binding Protein in Canine Masticatory Muscle Myositis," *J. Comp. Pathol.* 112(3):299–306, 1995.

Waltenberger, et al., "Involvement of Transforming Growth Factor–β in the Formation of Fibrotic Lesions in Carcinoid Heart Disease," *American Journal of Pathology,* 142(1):71–8. 1993.

Waltenberger, et al., "Induction of Transforming Growth Factor–β during Cardiac Allograft Rejection," *The Journal of Immunology,* 151(2):1147–57, 1993.

Alper, "Boning Up: Newly Isolated Proteins Heal Bad Breaks", *Science,* 263:324–325, 1994.

Bandara, G., et al., "Gene Transfer to Synoviocytes: Prospects for Gene Treatment of Arthritis", *DNA and Cell Biology,* 11(3):227–231, 1992.

Beck, L. Steven, et al., "Rapid Publication TGF–β$_1$ Induces Bone Closure of Skull Defects", *J. Bone Miner. Res.,* 6(11):1257–1265, 1991.

Boden, S.D., et al., "Estrogen Receptor mRNA Expression in Callus During Fracture Healing in the Rat", *Calcif Tissue Int,* 45:324–325, 1989.

Bonnarens and Einhorn, "Production of a Standard Closed Fracture in Laboratory Animal Bone", *J. Orthop. Res.,* 2:97–101, 1984.

Carrington, Jill L., et al., "Accumulation, Localization, and Compartmentation of Transforming Growth Factor β During Endochondral Bone Development", *J. Cell Biol.,* 107:1969–1975, 1988.

Centrella, Michael et al., "Skeletal Tissue and Transforming Growth Factor β", *FASEB J.,* 2:3066–3073, 1988.

Chen, Theresa L., et al., "Bone Morphogenetic Protein–2b Stimulation of Growth and Osteogenic Phenotypes in Rat Osteoblast–like Cells: Comparison with TGF–β$_1$", *J. Bone Miner. Res.,* 6(12):1387–1393, 1991.

Cunningham, Noreen S., et al., "Osteogenin and Recombinant Bone Morphogenetic Protein 2B are Chemotactic for Human Monocytes and Stimulate Transforming Growth Factor β$_1$ mRNA Expression", *Proc. Natl. Acad. Sci. USA,* 89:11740–11744, 1992.

Gunasekaran, S, et al., "Mineralized Collagen as a Substitute for Autograft Bone that Can Deliver Bone Morphogenic Protein", *The 19th Annual Meeting of the Society for Biomaterials,* p. 253, 1993.

Gunasekaran, S., et al., "Role of Mineralized Collagen as an Osteoconductive Biomaterial", *The 19th Annual Meeting of the Society for Biomaterials,* p. 161, 1993.

Gunasekaran, S., et al., "Mineralization of Collagen Without Nucleating Proteins", 11:30 A.M. V7.5, p. 426.

Horowitz, Mark C., et al., "Functional and Molecular Changes in Colony Stimulating Factor Secretion by Osteoblasts", *Connective Tissue Research,* 20:159–168, 1989.

Huggins, C.B., et al., "Experiments on the Theory of Osteogenesis", *Arch. Surg.,* 32(6):915–931, 1936.

Izumi, Toshihiro, et al., "Transforming Growth Factor β$_1$ Stimulates Type II Collagen Expression in Cultured Periosteum–Derived Cells", *J. Bone Miner. Res.,* 7(1):115–121, 1992.

Jingushi, Seiya, et al., "Genetic Expression of Extracellular Matrix Proteins Correlates with Histologic Changes During Fracture Repair", *J. Bone Miner. Res.,* 7(9):1045–1055, 1992.

Jingushi, S., et al., "Acidic Fibroblast Growth Factor (aFGF) Injection Stimulates Cartilage Enlargement and Inhibits Cartilage Gene Expression in Rat Fracture Healing", *J. Orthop. Res.,* 8:364–371, 1990.

Joyce, Michael E., et al., "Role of Growth Factors in Fracture Healing", *Clinical and Experimental Approaches to Dermal and Epidermal Repair: Normal and Chronic Wounds,* 391–416, 1991.

Joyce, Michael E., et al., "Transforming Growth Factor–β and the Initiation of Chondrogenesis and Osteogenesis in the Rat Femur", *The J. Cell Biol.,* 110:2195–2207, 1990.

Luyten, Frank P., et al., "Purification and Partial amino Acid Sequence of Osteogenin, a Protein Initiating Bone Differentiation", *J. Biol. Chem.,* 264(23):13377–13380, 1989.

O'Malley, Jr. and Ledley "Somatic Gene Therapy in Otolaryngology–Head and Neck Surgery", *Arch Otolaryngol Head Neck Surg,* 119:1191–1197, 1993.

Ozkaynak, Engin, et al., "OP–1 cDNA Encodes an Osteogenic Protein in the TGF–β Family", *EMBO J.,* 9(7):2085–2093, 1990.

Paralkar, Vishwas M., et al., "Identification and Characterization of Cellular Binding Proteins (Receptors) for Recombinant Human Bone Morphogenetic Protein 2B, an Initiator of Bone Differentiation Cascade", *Proc. Natl. Acad. Sci. USA,* 88:3397–3401, 1991.

Roessier, Blake J., et al., "Adenoviral–mediated Gene Transfer to Rabbit Synovium In Vivo", *J. Clin. Invest.,* 92:1085–1092, 1993.

Rosen, Vicki, et al., "Purification and Molecular Cloning of a Novel Group of BMPS and Localization of BMP MRNA in Developing Bone", *Connect. Tissue Res.,* 20:313–319, 1989.

Sampath, T.K., et al., "In Vitro Transformation of Mesenchymal Cells Derived From Embryonic Muscle into Cartilage in Response to Extracellular Matrix Components of Bone", *Proc. Natl. Acad. Sci. USA*, 81:3419–3423, 1984.

Sampath and Reddi, "Dissociative Extraction and Reconstitution of Extracellular Matrix Components Involved in Local Bone Differentiation", *Proc. Natl. Acad. Sci. USA*, 78(12):7599–7603, 1981.

Sandusky, G.E., Jr. et al., "Histologic Findings After In Vivo Placement of Small Intestine Submucosal Vascular Grafts and Saphenous Vein Grafts in the Carotid Artery in Dogs", *American Journal of Pathology*, 140(2):317–324, 1992.

Shimell, Mary Jane, et al., "The Drosophila Dorsal–Ventral Patterning Gene tolloid is Related to Human Bone Morphogenetic Protein 1", *Cell*, 67:469–481, 1991.

Srivastava, Carolyn H., et al., "Construction of a Recombinant Human Parvovirus B19: Adenoasociated Virus 2 (AAV) DNA Inverted Terminal Repeats are Functional in an AAV–B19 Hybrid Virus", *Proc. Natl. Acad. Sci. USA*, 86:8078–8082, 1989.

Toriumi, Dean M., et al., "Mandibular Reconstruction With a Recombinant Bone–Inducing Factor", *Arch Otolaryngol Head Neck Surg*, 117:1101–1112, 1991.

Ulmer, Jeffrey B., et al., "Heterologous Protection Against Influenza by Injection of DNA Encoding a Viral Protein", *Science*, 259:1745–1749, 1993.

Urist, Marshall R., et al., "Bone Cell Differentiation Growth Factors", *Science*, 220:680–220, 1983.

Urist, Marshall R., "Bone: Formation by Autoinduction", *Science*, 150:893–899, 1965.

Wang, Elizabeth A., et al., "Recombinant Human Bone Morphogenetic Protein Induces Bone Formation", *Proc. Natl. Acad. Sci. USA*, 87:2220–2224, 1990.

Wilson, James M., et al., "Somatic Gene Transfer in the Development of an Animal Model for Primary Hyperparathyroidism", *Endocrinology*, 130(5):2947–2954, 1992.

Wolff, Jon A., et al., "Direct Gene Transfer into Mouse Muscle In Vivo", *Science*, 247:1465–1468, 1990.

Wozney, John M., et al., "Novel Regulators of Bone Formation: Molecular Clones and Activities", *Science*, 242:1528–1534, 1988.

Yasko, Alan W., et al., "The Healing of Segmental Bone Defects, Induced by Recombinant Human Bone Morphogenetic Protein (rhBMP–2)", *The Journal of Bone and Joint Surgery*, 74–A(5):659–670, 1992.

Agarwala, Neena, et al, "Specific Binding of Parathyroid Hormone to Living Osteoclasts", *Journal of Bone and Mineral Research*, 7:531–539, 1992.

Bonadio et al., "Transgenic mouse model of the mild dominant form of osteogenesis imperfecta," *Proc. Natl. Acad. Sci. USA*, 87:7145–7149, 1990.

Davidson et al., "A model system for in vivo gene transfer into the central nervous system using an adenoviral vector," *Nature Genetics*, 3:219–223, 1993.

Falcone et al., "Macrophage and Foam Cell Release of Matrix–bound Growth Factors," *The Journal of Biological Chemistry*, 268(15):11951–11958, 1993.

Flaumenhaft et al., "Role of the Latent TGF–β Binding Protein in the Activation of Latent TGF–β by Co–Cultures of Endothelial and Smooth Muscle Cells," *The Journal of Cell Biology*, 120(4):995–1002, 1993.

Majmudar et al., "Bone Cell Culture in a Three–Dimensional Polymer Bead Stabilizes the Differentiated Phenotype and Provides Evidence That Osteoblastic Cells Synthesize Type III Collagen and Fibronectin," *Journal of Bone and Mineral Research*, 6(8):869–881, 1991.

Miyazono et al., "Retention of the Transforming Growth Factor–β1 Precursor in the Golgi Complex in a Latent Endoglycosidase H–sensitive Form," *The Journal of Biological Chemistry*, 267(8):5668–5675, 1992.

Pereira et al., "Genomic organization of the sequence coding for fibrillin, the defective gene product in Marfan syndrome," *Human Molecular Genetics*, 2(7):961–968, 1993.

Seitz et al., "Effect of Transforming Growth Factor β on Parathyroid Hormone Receptor Binding and cAMP Formation in Rat Osteosarcoma Cells", *Journal of Bone and Mineral Research*, 7:541–546, 1992.

Selander–Sunnerhagen et al., "How an Epidermal Growth Factor (EGF)–like Domain Binds Calcium," *The Journal of Biological Chemistry*, 267(27):19642–19649, 1992.

Steiner et al., "The New Enzymology of Precursor Processing Endoproteases," *The Journal of Biological Chemistry*, 267(33):23435–23438, 1992.

Stratford–Perricaudet et al., "Widespread Long–term Gene Transfer to Mouse Skeletal Muscles and Heart," *J. Clin. Invest.*, 90:626–630, 1992.

Benezra et al., "Thrombin–Induced Release of Active Basic Fibroblast Growth Factor–Heparan Sulfate Complexes from Subendothelial Extracellular Matrix," *Blood*, 81(12):3324–3331, Jun., 1993.

Colosetti et al., "$Ca^{2+}$ binding of latent transforming growth factor–β1 binding protein," *FEBS*, 320(2):140–144, Apr., 1993.

Falcone et al., "Macrophage and Foam Cell Release of Matrix–bound Growth Factors," *The Journal of Biological Chemistry*, 268(16):11951–11958, Jun., 1993.

Flaumenhaft et al., "Role of the Latent TGF–β Binding Protein in the Activation of Latent TGF–β by Co–Cultures of Endothelial and Smooth Muscle Cells," *The Journal of Cell Biology*, 120(4):995–1002, Feb., 1993.

Kanzaki et al., "TGF–β1 Binding Protein: A Component of the Large Latent Complex of TGF–β1 with Multiple Repeat Sequences," *Cell*, 61:1051–1061, Jun., 1990.

Miyazono et al., "Latent High Molecular Weight Complex of Transforming Growth Factor β1," *The Journal of Biological Chemistry*, 263(13):6407–6415, May, 1988.

Miyazono et al., "A role of the latent TGF–β1–binding protein in the assembly and secretion of TGF–β1," *The EMBO Journal*, 10(5):1091–1101, 1991.

Miyazono et al., "Retention of the Transforming Growth Factor–β1 Precursor in the Golgi Complex in a Latent Endoglycosidase H–sensitive Form," *The Journal of Biological Chemistry*, 267(8):5668–5675, Mar., 1992.

Morén et al., "Identification and Characterization of LTBP–2, a Novel Latent Transforming Growth Factor–β–binding Protein," *The Journal of Biological Chemistry*, 269(51):32469–32478, Dec., 1994.

Olofsson et al, "Transforming Growth Factor–β1, —β2, and —β3 Secreted by a Human Glioblastoma Cell Line," *The Journal of Biological Chemistry*, 267(27):19482–19488, Sep., 1992.

Taketazu et al., "Enhanced Expression of Transforming Growth Factor–βs and Transforming Growth Factor–β Type II Receptor in the Synovial Tissues of Patients with Rheumatoid Arthritis," *Laboratory Investigation*, 70(5):620–630, 1994.

Taipale et al., "Latent Transforming Growth Factor–β1 Associates to Fibroblast Extracellular Matrix via Latent TGF–β Binding Protein," *The Journal of Cell Biology*, 124(1 & 2):171–181, Jan., 1994.

Tsuji et al., "Molecular cloning of the large subunit of transforming growth factor type β masking protein and expression of the mRNA in various rat tissues," *Proc. Natl. Acad. Sci. USA*, 87:8835–8839, Nov., 1990.

Wakefield et al., "Latent Transforming Growth Factor–β from Human Platelets," *The Journal of Biological Chemistry*, 263(16):7646–7654, Jun., 1988.

Yin et al., "Isolation of a Novel Latent Transforming Growth Factor–β Binding Protein Gene (LTBP–3)," *The Journal of Biological Chemistry*, 270(17):10147–10160, Apr., 1995.

Rosen and Thies, "The BMP proteins in bone formation and repair," *Trends in Genetics*, 8(3):97–102, Mar., 1992.

Badylak et al., "Directed Connective Tissue Remodeling Upon a Biologic Collagen Substrate," *J. Cell Biochem. Supplement 16F*, p. 124, Apr. 3–16, 1992.

Benevisty and Reshef, "Direct introduction of genes into rats and expression of the genes," *Proc. Natl. Acad Sci. USA*, 83:9551–9555, Dec. 1986.

Bonadio and Goldstein, "Direct Gene Transfer into Skeletal Tissues In Vivo," *Gene Therapy Meeting; Cold Spring Harbor*, Conference Abstract, Sep. 21–25, 1994.

Edelman et al., "c–myc in Vasculoproliferative Disease," *Circulation Research*, 76(2):1.2–1.8, Feb., 1995.

Evans and Robbins, "Possible Orthopaedic Applications of Gene Therapy," *The Journal of Bone and Joint Surgery*, 77–A(7):1103–1114, Jul., 1995.

Indolfi et al., "Inhibition of cellular ras prevents smooth muscle cell proliferation after vascular injury in vivo," *Nature Medicine*, 1(6):541–545, Jun., 1995.

Invention Disclosure entitled "Small Intestinal Submucosa as Biomaterial to Promote Gene Transfer," Stephen G. Badylak, Jeffrey Bonadio and Sherry L. Voytik, Sep. 4, 1992.

Kaneda et al., "Increased Expression of DNA Cointroduced with Nuclear Protein in Adult Rat Liver," *Science*, 243:375–378, Jan., 1989.

Mannino and Gould–Fogerite, "Liposome Mediated Gene Transfer," *BioTechniques*, 6(7):682–690, 1988.

Mumper et al., "Interactive Polymeric Gene Delivery Systems for Enhanced Muscle Expression," *Abstract*, American Assoc. of Pharmaceutical Science, Miami Beach, FL, Nov. 6–9, 1995.

Nicolau et al., "In vivo expression of rat insulin after intravenous administration of the liposome–entrapped gene for rat insulin 1," *Proc. Natl. Acad. Sci. USA*, 80:1068–1072, Feb., 1983.

Simons et al., "Antisense c–myb oligonucleotides inhibit intimal arterial smooth muscle cell accumulation in vivo," *Nature*, 359:67–70, Sep., 1992.

Sumner et al., "Enhancement of Bone Ingrowth by Transforming Growth Factor–β," *The Journal of Bone and Joint Surgery*, 77–A(8):1135–1147, Aug., 1995.

Wolff et al., "Conditions Affecting Direct Gene Transfer into Rodent Muscle In Vivo," *BioTechniques*, 11(4): 474–485, 1991.

Wolff et al., "Expression of naked plasmids by cultured myotubes and entry of plasmids into T tubules and caveolae of mammalian skeletal muscle," *Journal of Cell Science*, 103:1249–1259, 1992.

Wu and Wu, "Receptor–mediated Gene Delivery and Expression in Vivo," *The Journal of Biological Chemistry*, 263(29):14621–14624, 1988.

Yin et al., "Molecular Cloning of a Novel Fibrillin–Like cDNA: Expression in Callus Tissue as Alternatively Spliced Transcripts," *40th Annual Meeting, Orthopaedic Research Society*, Conference Abstract, Feb. 21–24, 1994.

Zhu et al., "Direct Gene Transfer into Regenerating Achilles' Tendon," *40th Annual Meeting, Orthopaedic Research Society*, Conference Abstract, Feb. 21–24, 1994.

U.S. patent application Ser. No. 08/176,565; filed Jan. 3, 1994; entitled "Fluidized Intestinal Submucosa and its Use as an Injectable Tissue Graft".

U.S. patent application Ser. No. 08/343,204; filed Nov. 22, 1994; entitled "Fluidized Intestinal Submucosa and its Use as an Injectable Tissue Graft".

U.S. patent application Ser. No. 08/390.700; filed Feb. 17, 1995; entitled "Compositions and Method for Production of Transformed Cells".

U.S. patent application Ser. No. 08/386,432; filed Feb. 10, 1995; entitled "Bone Graft Composition".

U.S. patent application Ser. No. 08/386,452; filed Feb. 10, 1995; entitled "Submucosa as a Growth Substrate for Cells.".

Zhang et al., "Structure and Expression of Filbrillin–2, A Novel Microfibrillar Component Preferentially Located in Elastic Matrices", *The Journal of Cell Biology*, 124:855–863, 1994.

\* cited by examiner

FIG. 3A FIG. 3C FIG. 3E
anti-sense probe
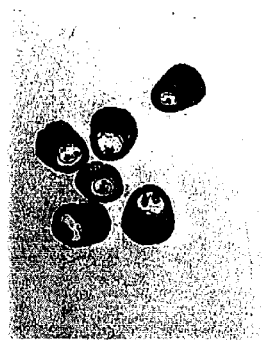  
sense probe
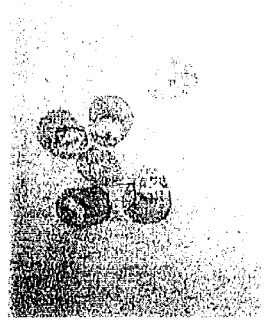
day 8.5 - 9.0  day 13.5  day 16.5
FIG. 3B FIG. 3D FIG. 3F

METHODS OF USING LATENT TGF-β BINDING PROTEINS

The present application is a continuation-in-part of U.S. Ser. No. 08/479,722, filed Jun. 7, 1995, which issued as U.S. Pat. No. 6074,840 on Jun. 13, 2000; which is a continuation-in-part of PTC/US95/02251, filed Feb. 21, 1995; which is a continuation-in-part of U.S. Ser. No. 08/316,650, filed Sep. 30, 1994, which issued as U.S. Pat. No. 5,942,496 on Aug. 24, 1999; which is a continuation-in-part of U.S. Ser. No. 08/199,780, filed Feb. 18, 1994, which issued as U.S. Pat. No. 5,763,416 on Jun. 9, 1998; the entire text and figures of which disclosures are specifically incorporated herein by reference without disclaimer. The United States government has certain rights in the present invention pursant to Grant HL-41926 from the National Institutes of Health.

BACKGROUND OF THE INVENTION

A. Field of the Invention

The present invention relates generally to the field of molecular biology. More particularly it relates to latent TGFβ binding protein (LTBP) genes, compositions and methods of use.

B. Description of the Related Art

1. TGF-β

Five TGF-β family members, which share 66–82% sequence identity, have been identified (Kingsley, 1994). Whereas TGF-β1 was cloned from a cDNA library derived from human placenta, TGF-β2 was subsequently purified from several mammalian cells and tissues, and TGF-β3, -β4, and -β5 were cloned by low stringency hybridization from mammalian, avian and amphibian cDNA libraries, respectively. Peptide growth factors/cytokines have also been identified that share sequence homology ($\leq 40\%$) with the TGF-βs (collectively, the TGF-βs plus these other cytokines make up the TGF-β superfamily). A unifying feature of the biology of these other cytokines (i.e., the Mullerian inhibiting substance, bone morphogenetic proteins, growth and differentiation factors, activin/inhibin, Drosophila decapentaplegic complex, and amphibian Vg1 protein) is the ability to regulate developmental processes. In every case where information is available, superfamily members are synthesized as larger precursors that are processed at endoproteolytic cleavage motifs, and they terminate with the sequence C-X-C-X. The three dimensional crystal structure of the TGF-β2 homodimer was recently reported (McDonald and Hendrickson, 1993). This work has led to the interesting and novel suggestion that TGF-β is related to certain peptide growth factors (e.g., NGF, PDGF, v-SIS) in a way that could not have been predicted from the deduced amino acid analysis.

2. Latent TGF-β Complexes

Many cell types produce TGF-β, and almost all cells bind TGF-β with affinities in the picomolar range—e.g., the type I and type II TGF-β cell surface receptors (glycoproteins of 53 and 75 kDa, respectively) are present in essentially all cells (Miyazono et al., 1994). Thus, TGF-β has powerful effects on most cell types, and cytokines such as TGF-β are thought to exert broad control the tissue remodeling that occurs during development, wound repair, and other situations (Sporn et al., 1986; Moses et al., 1990). (For a comprehensive all review of TGF-β effects, see Roberts and Sporn, 1990). For example, TGF-β was initially identified as a factor that stimulated the anchorage independent growth of rodent fibroblasts (Assoian et al., 1983; Frolik et al., 1983; Roberts et al., 1983). It is now known, however, that TGF-β acts as a potential growth inhibitor for most cells, i.e., epithelial, endothelial, and hematopoietic progenitor cells; both stimulates and inhibits cellular differentiation; induces extracellular matrix production by stimulating the expression of matrix macromolecules, stimulating the expression of matrix protease inhibitors, and decreasing the expression of matrix degrading proteases; inhibits the functional activities of immune cells; induces the chemotaxis of fibroblasts, macrophages, and smooth muscle cells; induces angiogenesis in vivo; inhibits endothelial migration; induces the expression of cell surface receptors for other cytokines (e.g., the EGF receptor); promotes the healing of incisional wounds; inhibits osteoblast proliferation in vitro; and induces new bone formation in vivo.

A molecular explanation for these complex (and, at times, conflicting) effects is not yet available, but hypotheses do exist. Sporn et al. (1986) have suggested, for example, that the ability of TGF-β to stimulate or inhibit the proliferation of mesenchymal cells depends on the state of cellular differentiation and the entire set of growth factors operant in that cell population. As such, the "biological meaning" of TGF-β signal transduction depends on the context (i.e., availability and presentation) of other growth factors present in the local environment: Fischer rat 3T3 cells transfected with a myc gene and incubated with TGF-β and PDGF proliferate in soft agar, whereas the same cells in the presence of TGF-β and EGF fail to grow (Roberts et al., 1985).

Whatever the mechanism, the autocrine and paracrine activities of TGF-β clearly must be regulated with precision. One regulatory strategy involves the temporal and spatial control of TGF-β gene expression. A second strategy involves the production and storage of TGF-β as a latent complex that is activated only under certain physiological and pathological conditions—e.g., tissue morphogenesis and remodeling, and wound healing. TGF-β1 can be isolated from serum and from most tissues as a latent complex (Pircher et al., 1986; Miyazono et al., 1988; Wakefield et al., 1988). In this regard, the latent complex has been purified from human platelets and characterized in detail (Miyazono et al., 1988). Following a 6-step protocol, the purified complex yielded protein bands of Mr 25,000 and 210,000 on SDS-PAGE under nonreducing conditions. After reduction, the 25 kDa band was shown to consist of subunits of Mr 12,500. On the other hand, the 210 kDa band consisted of a Mr 40,000 subunit and Mr 125–160,000 subunit.

TGF-β is also secreted from several producer cell lines in culture as a latent complex of 235 kDa (Gentry et al., 1987). TGF-β1 is initially synthesized in vitro as a 390 amino acid precursor that consists of a signal peptide, an amino-terminal propeptide, and the mature growth factor. Two precursor chains associate to form a disulfide-bonded dimer with latent activity. Homodimers occur most commonly, but heterodimers may also form (Ogawa et al., 1992). The full length dimer is cleaved at a endoproteolytic cleavage motif, but the propeptide dimer (i.e., the latency associated peptide or LAP) and the mature growth factor dimer typically remain non-covalendy associated. The mature TGF-β dimer is now known to be the 25 kDa band identified after nonreducing SDS-PAGE of the purified latent complex from platelets. In addition, LAP is known to be a component of the 210 kDa band identified after nonreducing SDS-PAGE of the purified latent complex from platelets (i.e., LAP has been shown to consist of two of the 40 kDa subunits).

Together LAP and the mature TGF-β dimer form the small latent complex. As demonstrated in platelets, small latent complexes may be associated with additional high molecular weight proteins, the best characterized of which is the latent TGF-β binding protein or LTBP (Kanzaki et al., 1990). (LTBP has been shown to be the 125–160 kDa subunit of the purified latent complex from platelets). Latent TGF-β complexes that contain LTBP are also known as large latent complexes. In contrast to platelet LTBP, the LTBP produced by fibroblasts typically is a 190 kDa polypeptide. The smaller size of platelet LTBP may be due to proteolytic processing or alternative splicing (Kanzaki et al., 1990; Tsuji et al., 1990).

3. LAP and Latency TGF-β latency results in part from the non-covalent association of the propeptide dimer and the mature TGF-β dimer (Pircher et al., 1984; Gentry et al., 1988; Wakefield et al., 1989). A cDNA for the TGF-β1 precursor was expressed in Chinese Hamster Ovary (CHO) cells, which do not express LTBP (Gentry et al., 1988), and almost all TGF-β activity recovered from the medium of transfected cells was latent. Use of deletion constructs has demonstrated that synthesis of biologically active TGF-β1 can proceed only from the first ATG codon, implicating LAP in the proper assembly of the small latent complex in these cells. Taken together, these studies indicate that LAP is sufficient to achieve the latent state. More recent studies have shown that carbohydrate structures within LAP make an important contribution to the latent state. For example, treatment of the latent form of TGF-β1 with endoglycosidase F led to activation of TGF-β (Miyazono and Heldin, 1989). (The structure of the mature TGF-β dimer was not affected by enzyme treatment). In particular, sialic acid residues seemed to be important, as treatment of the purified latent complex with sialidase was also able to activate TGF-β from the latent state.

4. Modulation of Latency

Latent complexes must be dissociated to activate mature TGF-β, art dissociation is considered to be a critical step in governing TGF-β effects (Twardzik et al., 1990; Sato et al., 1993). Dissociation by chemical treatment of the latent complex purified from platelets has been investigated (Miyazono et al., 1990). Incubation of the purified complex under conditions of varying pH revealed that TGF-β activity was unmasked at values below pH 3.5 and above pH 12.5. Incubation of latent TGF-β in 0.02% SDS or 8 M urea also effectively unmasked TGF-β activity, but incubation in 5 M NaCl did not. Wakefield et al. (Wakefield et al., 1989) have reported that, after activation, TGF-β1 and LAP reassociate in a time- and concentration-dependent manner under neutral, nondenaturing conditions. These results are consistent with the idea that the mature TGF-β dimer is non-covalently associated with LAP.

Latent TGF-β complexes are also dissociated by the action of certain enzymes. For example, latent TGF-β is activated by plasmin, which disrupts the structure of the large latent complex (Lyons et al., 1988; Taipale et al., 1995). Similar data exist for other enzymes, e.g., cathepsin D, mast cell chymase, leukocyte elastase, and the glycosidases. Recently, osteoclast-derived cells were shown to be capable of activating latent TGF-β in vitro (Oreffo et al., 1989). Osteoclast activation is of particular interest because of the hypothesis that TGF-β serves as a link between bone turnover and formation during bone remodeling (Centrella et al., 1991). The mechanism of TGF-β activation by osteoclasts is not known at present, but it is reasonable to think that local alteration of pH due to action of proton pumps in the osteoclast plasma membrane or the release of osteoclast-derived proteases may be involved in the activation process. Related to these observations, activated macrophages (as might be found at a wound site or during tissue morphogenesis) secrete sialidase and other proteases (Pilatte et al., 1987), and they can lower the local pH to 4.0 (Silver et al., 1988), both of which could contribute to TGF-β activation in vivo. As mentioned above, acidification weakens the non-covalent interaction between LAP and the mature TGF-β dimer (Wakefield et al., 1989).

SUMMARY OF THE INVENTION

The present invention concerns in an overall and general sense novel DNA segments and recombinant vectors encoding LTBP-2 or LTBP-3, and the creation and use of recombinant host cells through the application of DNA technology, that express LTBP-2 or LTBP-3 gene products. As such, the invention concerns DNA segment comprising an isolated gene that encodes a protein or peptide that includes an amino acid sequence essentially as set forth by a contiguous sequence from SEQ ID NO:2 or SEQ ID NO:4. These DNA segments are represented by those that include a nucleic acid sequence essentially as set forth by a contiguous sequence from SEQ ID NO:1 or SEQ ID NO:3.

Compositions that include a purified protein that has an amino acid sequence essentially as set forth by the amino acid sequence of SEQ ID NO:2 or SEQ ID NO:4 are also encompassed by the invention.

The TGF-βs represent a family of structurally related molecules with diverse effects on mammalian cell shape, growth, and differentiation (Roberts and Sporn, 1990). Initially synthesized as a precursor consisting of an amino-terminal propeptide followed by mature TGF-β, two chains of nascent pro-TGF-β associate in most tissues to form a Mr ~106,000 inactive disulfide-bonded dimer. Homodimers are most common, but heterodimers have also been described (Cheifetz et al., 1987; Ogawa et al., 1992). During biosynthesis the mature TGF-β dimer is cleaved from the propeptide dimer. TGF-β latency results in part from the non-covalent association of propeptide and mature TGF-β dimers (Pircher et al., 1984, 1986; Wakefield et al., 1987; Millan et al., 1992; Miyazono and Heldin, 1989). Consequently, the propeptide dimer is often referred to as the latency associated protein (LAP), and LAP plus the disulfide-bonded TGF-β dimer are also known as the small latent complex. In the extracellular space small latent complexes must be dissociated to activate mature TGF-β. The mechanism of activation of the latent complex is thought to be one of the most important steps governing TGF-β effects (Lyons et al., 1988; Antonelli-Orlidge et al., 1989; Twardzik et al., 1990; Sato et al., 1993).

In certain lines of cultured cells small latent growth factor complexes may contain additional high molecular weight proteins. The best characterized of these high molecular weight proteins is the latent TGF-β binding protein, or LTBP (Miyazono et al., 1988; Kanzaki et al., 1990; Tsuji et al., 1990; Olofsson et al., 1992; Taketazu et al., 1994). LTBP produced by different cell types is heterogeneous in size, perhaps because of alternative splicing or because of tissue-specific proteolytic processing (Miyazono et al., 1988; Wakefield et al., 1988; Kanzaki et al., 1990; Tsuji et al., 1990). Latent TGF-β complexes that contain LTBP are known as large latent complexes. LTBP has no known covalent linkage to mature TGF-β, but rather it is linked by a disulfide bond to LAP.

Regarding the novel protein LTBP-2 or LTBP-3, the present invention concerns DNA segments, that can be isolated from virtually any mammalian source, that are free from total genomic DNA and that encode proteins having LrBP-2-like or LTBP-3-like activity. DNA segments encoding LTBP-2-like or LTBP-3-like species may prove to encode proteins, polypeptides, subunits, functional domains, and the like.

As used herein, the term "DNA segment" refers to a DNA molecule that has been isolated free of total genomic DNA of a particular species. Therefore, a DNA segment encoding LTBP-2 or LTBP-3 refers to a DNA segment that contains LTBP-2 or LTBP-3 coding sequences yet is isolated away from, or purified free from, total genomic DNA of the species from which the DNA segment is obtained. Included within the term "DNA segment", are DNA segments and smaller fragments of such segments, and also recombinant vectors, including, for example, plasmids, cosmids, phagemids, phage, viruses, and the like.

Similarly, a DNA segment comprising an isolated or purified LTBP-2 or LTBP-3 gene refers to a DNA segment including LTBP-2 or LTBP-3 coding sequences and, in certain aspects, regulatory sequences, isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences, cDNA sequences and smaller engineered gene segments that express, or may be adapted to express, proteins, polypeptides or peptides.

"Isolated substantially away from other coding sequences" means that the gene of interest, in this case, a gene encoding LTBP-2 or LTBP-3, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences that encode an LTBP-2 or LTBP-3 species that includes within its amino acid sequence an amino acid sequence essentially as set forth in SEQ ID NO:2 or SEQ ID NO:4. In other particular embodiments, the invention concerns isolated DNA segments and recombinant vectors incorporating DNA sequences that include within their sequence a nucleotide sequence essentially as set forth in SEQ ID NO:1 or SEQ ID NO:3.

The term "a sequence essentially as set forth in SEQ ID NO:2 or SEQ ID NO:4" means that the sequence substantially corresponds to a portion of SEQ ID NO:2 or SEQ ID NO:4 and has relatively few amino acids that are not identical to, or a biologically functional equivalent of, the amino acids of SEQ ID NO:2 or SEQ ID NO:4. The term "biologically functional equivalent" is well understood in the art and is further defined in detail herein (for example, see section 7, preferred embodiments). Accordingly, sequences that have between about 70% and about 80%; or more preferably, between about 81% and about 90%; or even more preferably, between about 91% and about 99%; of amino acids that are identical or functionally equivalent to the amino acids of SEQ ID NO:2 or SEQ ID NO:4 will be sequences that are "essentially as set forth in SEQ ID NO:2 or SEQ ID NO:4".

In certain other embodiments, the invention concerns isolated DNA segments and recombinant vectors that include within their sequence a nucleic acid sequence essentially as set forth in SEQ ID NO:1 or SEQ ID NO:3. The term "essentially as set forth in SEQ ID NO:1 or SEQ ID NO:3" is used in the same sense as described above and means that the nucleic acid sequence substantially corresponds to a portion of SEQ ID NO:1 or SEQ ID NO:3 and has relatively few codons that are not identical, or functionally equivalent, to the codons of SEQ ID NO:1 or SEQ ID NO:3. Again, DNA segments that encode proteins exhibiting LTBP-2-like or LTBP-3-like activity will be most preferred.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Naturally, the present invention also encompasses DNA segments that are complementary, or essentially complementary, to the sequence set forth in SEQ ID NO:1 or SEQ ID NO:3. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1 or SEQ ID NO:3, under relatively stringent conditions such as those described herein.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared that include a short contiguous stretch identical to or complementary to SEQ ID NO:1 or SEQ ID NO:3, such as about 14 nucleotides, and that are up to about 10,000 or about 5,000 base pairs in length, with segments of about 3,000 being preferred in certain cases. DNA segments with total lengths of about 1,000, about 500, about 200, about 100 and about 50 base pairs in length (including all intermediate lengths) are also contemplated to be useful.

It will be readily understood that "intermediate lengths", in these contexts, means any length between the quoted ranges, such as 14, 15, 16, 17, 18, 19, 20, etc.; 21, 22, 23, etc.; 30, 31, 32, etc.; 50, 51, 52, 53, etc.; 100, 101, 102, 103, etc.; 150, 151, 152, 153, etc.; including all integers through the 200–500; 500–1,000; 1,000–2,000; 2,000–3,000; 3,000–5,000; 5,000–10,000 ranges, up to and including sequences of about 12,001, 12,002, 13,001, 13,002 and the like.

It will also be understood that this invention is not limited to the particular nucleic acid and amino acid sequences of SEQ ID NO:1 or SEQ ID NO:3; and SEQ ID NO:2 or SEQ ID NO:4, respectfully. Recombinant vectors and isolated DNA segments may therefore variously include the LTBP-2 or LTBP-3 coding regions themselves, coding regions bearing selected alterations or modifications in the basic coding region, or they may encode larger polypeptides that nevertheless include LTBP-2 or LTBP-3-coding regions or may encode biologically functional equivalent proteins or peptides that have variant amino acids sequences.

The DNA segments of the present invention encompass biologically functional equivalent LTBP-2 or LTBP-3 proteins and peptides. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level.

If desired, one may also prepare fusion proteins and peptides, e.g., where the LTBP-2 or LTBP-3 coding regions are aligned within the same expression unit with other proteins or peptides having desired functions, such as for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which the coding portion of the DNA segment, whether encoding a full length protein or smaller peptide, is positioned under the control of a promoter. The promoter may be in the form of the promoter that is naturally associated with a LTBP-2 or LTBP-3 gene, as may be obtained by isolating the 5' non-coding sequences located upstream of the coding segment or exon, for example, using recombinant cloning and/or PCR™ technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with an LTBP-2 or LTBP-3 gene in its natural environment. Such promoters may include LTBP-2 or LTBP-3 promoters normally associated with other genes, and/or promoters isolated from any bacterial, viral, eukaryotic, or mammalian cell. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the Pichia expression vector system (Pharmacia LKB Biotechnology).

In connection with expression embodiments to prepare recombinant LTBP-2 or LTBP-3 proteins and peptides, it is contemplated that longer DNA segments will most often be used, with DNA segments encoding the entire LTBP-2 or LTBP-3 protein or functional domains, subunits, etc. being most preferred. However, it will be appreciated that the use of shorter DNA segments to direct the expression of LTBP-2 or LTBP-3 peptides or epitopic core regions, such as may be used to generate anti-LTBP-2 or LTBP-3 antibodies, also falls within the scope of the invention. DNA segments that encode peptide antigens from about 15 to about 50 amino acids in length, or more preferably, from about 15 to about 30 amino acids in length are contemplated to be particularly useful.

The LTBP-2 or LTBP-3 gene and DNA segments may also be used in connection with somatic expression in an animal or in the creation of a transgenic animal. Again, in such embodiments, the use of a recombinant vector that directs the expression of the full length or active LTBP-2 or LTBP-3 protein is particularly contemplated.

In addition to their use in directing the expression of the LTBP-2 or LTBP-3 protein, the nucleic acid sequences disclosed herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the some sequence as, or is complementary to, a 14 nucleotide long contiguous sequence of SEQ ID NO:1 or SEQ ID NO:3 will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to LTBP-2 or LTBP-3-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of 10–14, 15–20, 30, 50, or even of 100–200 nucleotides or so, identical or complementary to SEQ ID NO:1 or SEQ ID NO:3, are particularly contemplated as hybridization probes for use in, e.g., Southern and Northern blotting. This would allow LTBP-2 or LTBP-3 structural or regulatory genes to be analyzed, both in diverse cell types and also in various mammalian cells. The total size of fragment, as well as the size of the complementary stretch(es), will ultimately depend on the intended use or application of the particular nucleic acid segment. Smaller fragments will generally find use in hybridization embodiments, wherein the length of the contiguous complementary region may be varied, such as between about 10–14 and about 100 nucleotides, but larger contiguous complementarity stretches may be used, according to the length complementary sequences one wishes to detect.

The use of a hybridization probe of about 10–14 nucleotides in length allows the formation of a duplex molecule that is both stable and selective. Molecules having contiguous complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 contiguous nucleotides, or even longer where desired.

Hybridization probes may be selected from any portion of any of the sequences disclosed herein. All that is required is to review the sequence set forth in SEQ ID NO:1 or SEQ ID NO:3 and to select any continuous portion of the sequence, from about 10–14 nucleotides in length up to and including the full length sequence, that one wishes to utilize as a probe or primer. The choice of probe and primer sequences may be governed by various factors, such as, by way of example only, one may wish to employ primers from towards the termini of the total sequence.

The process of selecting and preparing a nucleic acid segment that includes a contiguous sequence from within SEQ ID NO:1 or SEQ ID NO:3 may alternatively be described as preparing a nucleic acid fragment. Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,603,102 (incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of LTBP-2 or LTBP-3 gene or cDNA fragments. Depending on the application envisioned, one will desire to employ varying conditions of hybridization to achieve varying degrees of selectivity of probe towards target sequence. For applications requiring high selectivity, one will typically desire to employ relatively stringent conditions to forms the hybrids, e.g., one will select relatively low salt and/or high temperature conditions, such as provided by about 0.02 M to about 0.15 M NaCl at temperatures of 50° C. to 70° C. Such selective conditions tolerate little, if any, mismatch between the probe and the template or target strand, and would be particularly suitable for isolating LTBP-2 or LTBP-3 genes.

Of course, for some applications, for example, where one desires to prepare mutants employing a mutant primer strand hybridized to an underlying template or where one seeks to isolate LTBP-2 or LTBP-2 or LTBP-3-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 3A, FIG. 3B, FIG. 3C, FIG. 3D, FIG. 3E and FIG. 3F. Overview of expression of the new LTBP-like (LTBP-2 or LTBP-3) gene during murine development as determined by tissue in situ hybridization. FIG. 3A, FIG. 3B, FIG. 3C, FIG. 3D, FIG. 3E and FIG. 3F are autoradiograms made by direct exposure of tissue sections to film after hybridization with radiolabeled probes. Identical conditions were maintained throughout autoradiography and photography, thereby allowing a comparison of the overall strength of hybridization in all tissue sections. The transcript is expressed in connective tissue, mesenchyme, liver, heart and CNS.

FIG. 3A. Day 8.5–9.0; sections contain embryos surrounded by intact membranes, uterine tissues, and the placental disk, cut in random planes; anti-sense probe.

FIG. 3B. Day 8.5–9.0; sections contain embryos surrounded by intact membranes, uterine tissues, and the placental disk, cut in random planes; sense probe.

FIG. 3C. Day 13.5; sections contain isolated whole embryos sectioned in the sagittal plane near or about the mid-line; anti-sense probe.

FIG. 3D. Day 13.5; sections contain isolated whole embryos sectioned in the sagittal plane near or about the mid-line; sense probe.

FIG. 3E. Day 16.5; sections contain isolated whole embryos sectioned in the sagittal plane near or about the mid-line, anti-sense probe.

FIG. 3F. Day 16.5; sections contain isolated whole embryos sectioned in the sagittal plane near or about the mid-line, sense probe.

DESCRIPTION OF THE PREFERRED EMBODIMENT

Figure 1:
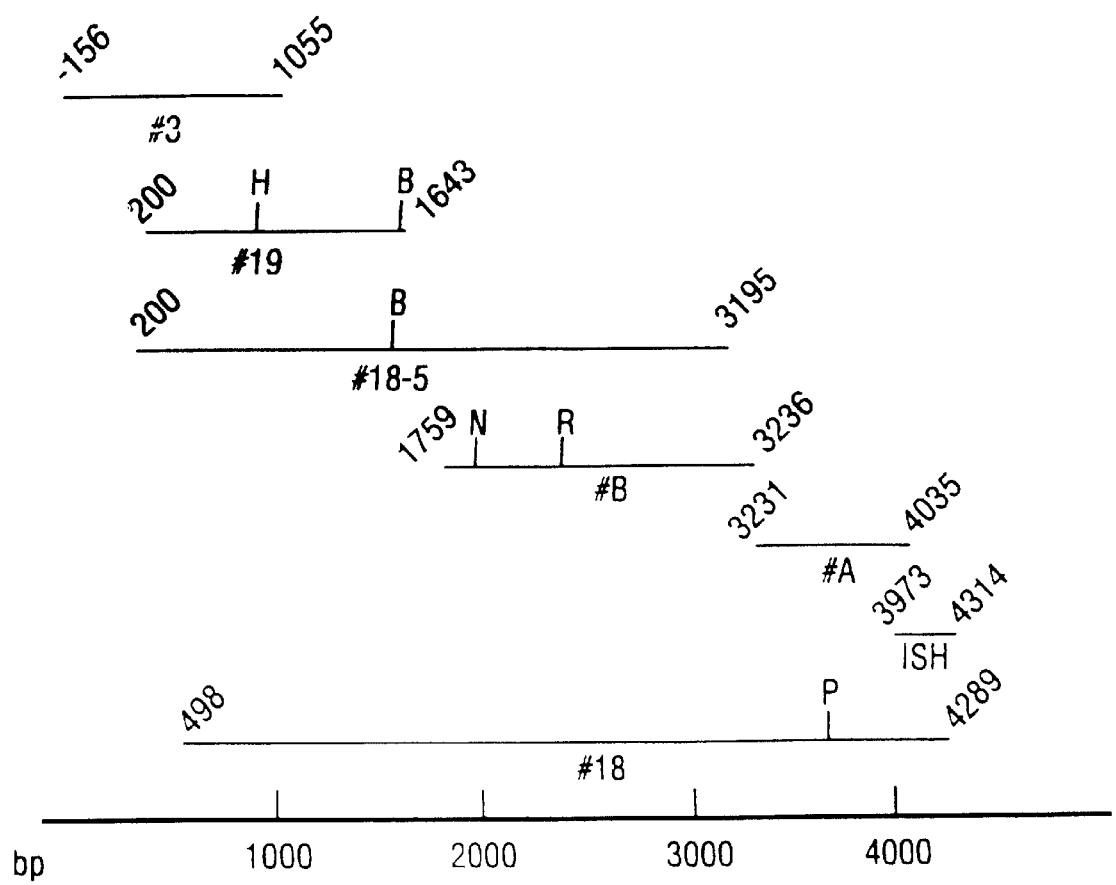
FIG. 1. Overlapping murine cDNA clones representing the LTBP-like (LTBP-2 or LTBP-3) sequence. A partial representation of restriction sites is shown. N, NcoI; P, PvuII; R, RsaII; B, BamHI; H, HindIII. The numbering system at the bottom assumes that the "A" of the initiator Met codon is nt #1.

1. Applications of Bone Repair Technology to Human Treatment

The following is a brief discussion of four human conditions to exemplify the variety of diseases and disorders that would benefit from the development of new technology to improve bone repair and healing processes. In addition to the following, several other conditions, such as, for example, vitamin D deficiency; wound healing in general; soft skeletal tissue repair; and cartilage and tendon repair and regeneration, may also benefit from technology concerning the stimulation of bone progenitor cells.

The first example is the otherwise healthy individual who suffers a fracture. Often, clinical bone fracture is treated by casting to alleviate pain and allow natural repair mechanisms to repair the wound. While there has been progress in the treatment of fracture in recent times, even without considering the various complications that may arise in treating fractured bones, any new procedures to increase bone healing in normal circumstances would represent a great advance.

A second example which may benefit from new treatment methods is osteogenesis imperfecta (OI). OI encompasses various inherited connective tissue diseases that involve bone and soft connective tissue fragility in humans (Byers and Steiner, 1992; Prockop, 1990). About one child per 5,000–20,000 born is affected with OI and the disease is associated with significant morbidity throughout life. A certain number of deaths also occur, resulting in part from the high propensity for bone fracture and the deformation of abnormal bone after fracture repair (OI types II–IV; Bonadio and Goldstein, 1993). The relevant issue here is quality of life; clearly, the lives of affected individuals would be improved by the development of new therapies designed to stimulate and strengthen the fracture repair process.

OI type I is a mild disorder characterized by bone fracture without deformity, blue sclerae, normal or near normal stature, and autosomal dominant inheritance (Bonadio and Goldstein, 1993). Osteopenia is associated with an increased rate of lone bone fracture upon ambulation (the fracture frequency decreases dramatically at puberty and during young adult life, but increases once again in late middle age). Hearing loss, which often begins in the second or third decade, is a feature of this disease in about half the families and can progress despite the general decline in fracture frequency. Dentinogenesis imperfecta is observed in a subset of individuals.

In contrast, OI types II–VI represent a spectrum of more severe disorders associated with a shortened life-span. OI type II, the perinatal lethal form, is characterized by short stature, a soft calvarium, blue sclerae, fragile skin, a small chest, floppy appearing lower extremities (due to external rotation and abduction of the femurs), fragile tendons and ligaments, bone fracture with severe deformity, and death in the perinatal period due to respiratory insufficiency. Radiographic signs of bone weakness include compression of the femurs, bowing of the tibiae, broad and beaded ribs, and calvarial thinning.

OI type III is characterized by short stature, a triangular facies, severe scoliosis, and bone fracture with moderate deformity. Scoliosis can lead to emphysema and a shortened life-span due to respiratory insufficiency. OI type IV is characterized by normal sclerae, bone fracture with mild to moderate deformity, tooth defects, and a natural history that essentially is intermediate between OI type II and OI type I.

More than 200 OI mutations have been characterized since 1989 (reviewed in Byers and Steiner, 1992; Prockop, 1990). The vast majority occur in the COL1A1 and COL1A2 genes of type I collagen. Most cases of OI type I appear to result from heterozygous mutations in the COL1A1 gene that decrease collagen production but do not alter primary structure, i.e., heterozygous null mutations affecting COL1A1 expression. Most cases of OI types II–IV result from heterozygous mutations in the COL1A1 and COL1A2 genes that alter the structure of collagen.

A third important example is osteoporosis. The term osteoporosis refers to a heterogeneous group of disorders characterized by decreased bone mass and fractures. An estimated 20–25 million people are at increased risk for fracture because of site-specific bone loss. Risk factors for osteoporosis include increasing age, gender (more females), low bone mass, early menopause, race (Caucasians), low calcium intake, reduced physical activity, genetic factors, environmental factors (including cigarette smoking and abuse of alcohol or caffeine), and deficiencies in neuromuscular control that create a propensity to fall.

More than a million fractures in the USA each year can be attributed to osteoporosis, and in 1986 alone the treatment of osteoporosis cost an estimated 7–10 billion health care dollars. Demographic trends (i.e., the gradually increasing age of the US population) suggest that these costs may increase 2–3 fold by the year 2020 if a safe and effective treatment is not found. Clearly, osteoporosis is a significant health care problem.

Clinically, osteoporosis is segregated into type I and type II. Type I osteoporosis occurs predominantly in middle aged women and is associated with estrogen loss at the menopause, while osteoporosis type II is associated with advancing age. Much of the morbidity and mortality associated with osteoporosis results from immobilization of elderly patients following fracture.

Current therapies for osteoporosis patients focus on fracture prevention, not fracture repair. This remains an important consideration because of the literature, which clearly states that significant morbidity and mortality are associated with prolonged bed rest in the elderly, particularly those who have suffered hip fractures. Complications of bed rest include blood clots and pneumonia. These complications are recognized and measures are usually taken to avoid them, but these measures hardly represent the best approach to therapy. Thus, the osteoporotic patient population would benefit from new therapies designed to strengthen bone and speed up the fracture repair process, thereby getting these people on their feet before the complications arise.

A fourth example is related to bone reconstruction and, specifically, the ability to reconstruct defects in bone tissue that result from traumatic injury; cancer or cancer surgery; birth defect; a developmental error or heritable disorder; or aging. There is a significant orthopaedic need for more stable total joint implants, and cranial and facial bone are particular targets for this type of reconstructive need. The availability of new implant materials, e.g., titanium, has permitted the repair of relatively large defects. Titanium implants provide excellent temporary stability across bony defects. However, experience has shown that a lack of viable bone bridging the defect can result in exposure of the appliance, infection, structural instability and, ultimately, failure to repair the defect.

Autologous bone grafts are another possible reconstructive modality, but they have several demonstrated disadvantages in that they must be harvested from a donor site such as iliac crest or rib, they usually provide insufficient bone to completely fill the defect, and the bone that does form is sometimes prone to infection and resorption. Partially purified xenogeneic preparations are not practical for clinical use because microgram quantities are purified from kilograms of bovine bone, making large scale commercial production both costly and impractical. Allografts and demineralized bone preparations are therefore often employed.

Microsurgical transfers of free bone grafts with attached soft tissue and blood vessels can close bony defects with an immediate source of blood supply to the graft. However, these techniques are time consuming, have been shown to produce a great deal of morbidity, and can only be used by specially trained individuals. Furthermore, the bone implant is often limited in quantity and is not readily contoured. In the mandible, for example, the majority of patients cannot wear dental appliances using presently accepted techniques (even after continuity is established), and thus gain little improvement in the ability to masticate. Toriumi et al., have written that, "reconstructive surgeons should have at their disposal a bone substitute that would be reliable, biocompatible, easy to use, and long lasting and that would restore mandibular continuity with little associated morbidity."

In connection with bone reconstruction, specific problem areas for improvement are those concerned with treating large defects, such as created by trauma, birth defects, or particularly, following tumor resection. The success of orthopaedic implants, interfaces and artificial joints could conceivably be improved if the surface of the implant, or a functional part of an implant, were to be coated with a bone stimulatory agent. The surface of implants could be coated with one or more appropriate materials in order to promote a more effective interaction with the biological site surrounding the implant and, ideally, to promote tissue repair.

2. Bone Repair

Bone tissue is known to have the capacity for repair and regeneration and there is a certain understanding of the cellular and molecular basis of these processes. The initiation of new bone formation involves the commitment, clonal expansion, and differentiation of progenitor cells. Once initiated, bone formation is promoted by a variety of polypeptide growth factors, Newly formed bone is then maintained by a series of local and systemic growth and differentiation factors.

The concept of specific bone growth-promoting agents is derived from the work of Huggins and Urist. Huggins et al., 1936, demonstrated that autologous transplantation of canine incisor tooth to skeletal muscle resulted in local new bone formation (Huggins et al., 1936). Urist and colleagues reported that demineralized lyophilized bone segments induced bone formation (Urist, 1965; Urist et al., 1983), a process that involved macrophage chemotaxis; the recruitment of progenitor cells; the formation of granulation tissue, cartilage, and bone; bone remodeling; and marrow differentiation. The initiation of cartilage and bone formation in an extraskeletal site, a process referred to as osteoinduction, has permitted the unequivocal identification of initiators of bone morphogenesis (Urist, 1965; Urist et al., 1983; Sampath et al., 1984; Wang et al., 1990; Cunningham et al., 1992).

Significant progress has now been made in characterizing the biological agents elaborated by active bone tissue during growth and natural bone healing. Demineralized bone matrix is highly insoluble; Sampath and Reddi (1981) showed that only 3% of the proteins can be extracted using strong combinations of denaturants and detergents. They also showed that the unfractionated demineralized bone extract will initiate bone morphogenesis, a critical observation that led to the purification of "osteoinductive" molecules. Families of proteinaceous osteoinductive factors have now been purified and characterized. They have been variously referred to in the literature as bone morphogenetic or morphogenic proteins (BMPs), osteogenic bone inductive proteins or osteogenic proteins (OPs).

3. Bone Repair and Growth Factors and Cytokines

Following their initial purification, several bone morphogenetic protein genes have now been cloned using molecular techniques (Wozney et al., 1988; Rosen et al., 1989; summarized in Alper, 1994). This work has established BMPs as members of the transforming growth factor-$\beta$ (TGF-$\beta$) superfamily based on DNA sequence homologies. Other TGF molecules have also been shown to participate in new bone formation, and TGF-$\beta$ is regarded as a complex multifunctional regulator of osteoblast function (Centrella et al., 1988; Carrington et al., 1988; Seitz et al., 1992). Indeed, the family of transforming growth factors (TGF-$\beta$1, TGF-$\beta$2, and TGF-$\beta$3) has been proposed as potentially useful in the treatment of bone disease (U.S. Pat. No. 5,125,978, incorporated herein by reference).

Transforming growth factors (TGFs) have a central role in regulating tissue healing by affecting cell proliferation, gene expression, and matrix protein synthesis (Roberts and Sporn, 1989). While not necessarily a direct effect, evidence has been provided that TGF-$\beta$1 and TGF-$\beta$2 can initiate both chondrogenesis and osteogenesis (Joyce et al., 1990; Izumi et al., 1992; Jingushi et al., 1992). In these studies new cartilage and bone formation appeared to be dose dependent (i.e., dependent on the local growth factor concentration).

The data also suggested that TGF-$\beta$1 and TGF-$\beta$2 stimulated cell differentiation by a similar mechanism, even though they differed in terms of the ultimate amount of new cartilage and bone that was formed.

Other growth factors/hormones besides TGF and BMP may influence new bone formation following fracture. Bolander and colleagues injected recombinant acidic fibroblast growth factor into a rat fracture site (Jingushi et al., 1990). The major effect of multiple high doses (1.0 mg/50 ml) was a significant increase in cartilage tissue in the fracture gap, while lower doses had no effect. These investigators also used the reverse transcriptase-polymerase chain reaction (PCR™) technique to demonstrate expression of estrogen receptor transcripts in callus tissue (Boden et al., 1989). These results suggested a role for estrogen in normal fracture repair.

Horowitz and colleagues have shown that activated osteoblasts will synthesize the cytokine, macrophage colony stimulating factor (Horowitz et al., 1989). The osteotropic agents used in this study included lipopolysaccharide, PTH1-84, PTH1-34, vitamin D and all-trans retinoic acid. This observation has led to the suggestion that osteoblast activation following fracture may lead to the production of cytokines that regulate both hematopoiesis and new bone formation. Various other proteins and polypeptides that have been found to be expressed at high levels in osteogenic cells, such as, e.g., the polypeptide designated Vgr-1 (Lyons et al., 1989), also have potential for use in connection with the present invention.

4. Protein Administration and Bone Repair

Several studies have been conducted in which preparations of protein growth factors, including BMPs, have been administered to animal in an effort to stimulate bone growth. The results of four such exemplary studies are described blow.

Toriumi et al., studied the effect of recombinant BMP-2 on the repair of surgically created defects in the mandible of adult dogs (Toriumi et al., 1991). Twenty-six adult hounds were segregated into three groups following the creation of a 3 cm full thickness mandibular defect: 12 animals received test implants composed of inactive dog bone matrix carrier and human BMP-2, 10 animals received control implants composed of carrier without BMP-2, and BMP4 animals received no implant. The dogs were euthanized at 2.5–6 months, and the reconstructed segments were analyzed by radiography, histology, histomorphometry, and biomechanical testing. Animals that received test implants were euthanized after 2.5 months because of the presence of well mineralized bone bridging the defect. The new bone allowed these animals to chew a solid diet, and the average bending strength of reconstructed mandibles was 27% of normal ('normal' in this case represents the unoperated, contralateral hemimandible). In contrast, the implants in the other two groups were non-functional even after 6 months and showed minimal bone formation.

Yasko et al., published a related study in which the effect of BMP-2 on the repair of segmental defects in the rat femur was examined (Yasko et al., 1992). The study design included a group that received a dose of 1.4 mg of BMP-2, another group that received 11.0 mg of BMP-2, and a control group that received carrier matrix alone. Endochondral bone formation was observed in both groups of animals that received BMP-2. As demonstrated by radiography, histology, and whole bone (torsion) tests of mechanical integrity, the larger dose resulted in functional repair of the 5-mm defect beginning 4.5 weeks after surgery. The lower dose resulted in radiographic and histological evidence of new bone formation, but functional union was not observed even after 9 weels post surgery. There was also no evidence of bone formation in control animals at this time.

Chen et al., showed that a single application of 25–100 mg of recombinant TGF-β1 adjacent to cartilage induced endochondral bone formation in the rabbit ear full thickness skin wounds (Chen et al., 1991). Bone formation began 21 days following the creation of the wound and reached a peak at day 42, as demonstrated by morphological methods. Active bone remodeling was observed beyond this point.

In a related study, Beck et. al., demonstrated that a single application of TGF-β1 in a 3% methylcellulose gel was able to repair surgically induced large skull defects that otherwise heal by fibrous connective tissue and never form bone (Beck et al., 1991). Bony closure was achieved within 28 days of the application of 200 mg of TGF-β1 and the rate of healing was shown to be dose dependent.

Studies such as those described above have thus established that exogenous growth factors can be used to stimulate new bone formation/repair/regeneration in vivo. Certain U.S. Patents also concern methods for treating bone defects or inducing bone formation. For example, U.S. Pat. No. 4,877,864 relates to the administration of a therapeutic composition of bone inductive protein to treat cartilage and/or bone defects; U.S. Pat. No. 5,108,753 concerns the use of a device containing a pure osteogenic protein to induce endochondral bone formation and for use in periodontal, dental or craniofacial reconstructive procedures.

5. Recombinant Expression

The use of recombinant expression systems in the preparation of LTBP-2 and LTBP-3 polypeptides is particularly contemplated. To express a recombinant LTBP-2 and LTBP-3 polypeptides, whether mutant or wild-type, in accordance with the present invention one would prepare an expression vector that comprises an LTBP-2- or LTBP-3- encoding nucleic acid segment under the control of one or more promoters. The "upstream" promoters stimulate transcription of the DNA and promote expression of the encoded recombinant protein. This is the meaning of "recombinant expression" in this context.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli* and *B. subtilis* transformed with recombinant bacteriophage DNA, plasmid DNA or cosmid DNA expression vectors.

Certain examples of prokaryotic hosts are *E. coli* strain RR1, *E. coli* LE392, *E. coli* B, *E. coli* X 1776 (ATCC No. 31537) as well as *E. coli* W3110 (F-, lambda-, prototrophic, ATCC No. 273325); bacilli such as *Bacillus subtilis*; and other enterobacteriaceae such as *Salmonella typhimurium, Serratia marcescens*, and various Pseudomonas species.

In general, plasmid vectors containing replicon and control sequences which are derived from species compatible with the host cell are used in connection with these hosts. The vector ordinarily carries- a replication site, as well as marking sequences which are capable of providing phenotypic selection in transformed cells. For example, *E. coli* is often transformed using pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM-11™ may be utilized in making a recombinant phage vector which can be used to transform host cells, such as *E. coli* LE392. Further useful vectors include pIN vectors (Inouye et al., 1985); and pGEX vectors, for use in generating glutathione S-transferase (GST) soluble fusion proteins for later purification and separation or cleavage.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

For expression in Saccharomyces, the plasmid YRp7, for example, is commonly used (Stinchcomb et al., 1979; Kingsman et al., 1979; Tschemper et al., 1980). This plasmid already contains the trpL gene which provides a selection marker for a mutant strain of yeast lacking the ability to grow in tryptophan, for example ATCC No. 44076 or PEP4-1 (Jones, 1977). The presence of the trpL lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more LTBP-2- or LTBP-3- encoding DNA sequences.

In a useful insect system, *Autograph californica* nuclear polyhidrosis virus (AcNPV) is used as a vector to express foreign genes. The virus grows in *Spodoptera frugiperda* cells. The LTBP coding sequences are cloned into non-essential regions (for example the polyhedrin gene) of the virus and placed under control of an AcNPV promoter (for example the polyhedrin promoter). Successful insertion of the coding sequences results in the inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., U.S. Pat. No. 4,215,051 issued to Smith).

Examples of useful mammalian host cell lines are VERO and HeLa cells, Chinese hamster ovary (CHO) cell lines, W138, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein, particularly with respect to the ability of LTBP-2 and LTBP-3 polypeptides to bind to TGFβ proteins.

Different host cells have characteristic and specific mechanisms for the post-translational processing and modification of proteins. Appropriate cells lines or host systems can be chosen to ensure the correct modification and processing of the foreign protein expressed. To this end, eukaryotic host cells may also be used if desired, with a cell that allows for high-level expression of LTBP-2 and LTBP-3 polypeptides being preferred.

Expression vectors for use in mammalian such cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired LTBP-encoding gene sequence, provided such control sequences are compatible with the host cell systems.

A number of viral based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the LTBP polypeptides in infected hosts.

Specific initiation signals may also be required for efficient translation of LTBP-2 and LTBP-3 coding sequences. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators (Bittner et al., 1987).

For long-term, high-yield production of recombinant LTBP-2 or LTBP-3 proteins, stable expression is preferred. For example, cell lines that stably express constructs encoding LTBP-2 or LTBP-3 polypeptides may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited, to the herpes simplex vinis thymidine kinase (Wigler et al., 1977), hypoxanthine-guanine phosphoribosyltransferase (Szybalska et al., 1962) and adenine phosphoribosyltransferase genes (Lowy et al., 1980), in tk-, hgprt- or aprt-cells, respectively. Also, antimetabolite resistance can be used as the basis of selection for dhfr, that confers resistance to methotrexate (Wigler et al., 1980; O'Hare et al., 1981); gpt, that confers resistance to mycophenolic acid (Mulligan et al., 1981); neo, that confers resistance to the aminoglycoside G-418 (Colberre-Garapin et al., 1981); and hygro, that confers resistance to hygromycin (Santerre et al., 1984).

6. Site-specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art.

Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired osteotropic protein. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected LTBP-2 or LTBP-3 gene using site-directed mutagenesis is provided as a means of producing potentially useful species and is not meant to be limiting as there are other ways in which sequence variants of osteotropic genes may be obtained. For example, recombinant vectors encoding the desired osteotropic gene may be treated with mutagenic agents, such as hydroxylamine, to obtain sequence variants.

7. In Situ Hybridization

The following technique describes the detection of mRNA in tissue obtained from the site of bone regeneration. This may be useful for detecting expression of LTBP-2 or LTBP-3.

DNA from a plasmid containing the gene for which mRNA is to be detected is linearized, extracted, and precipitated with ethanol. Sense and antisense trncripts are generated from 1 mg template with T3 and T7 polymerases, e.g., in the presence of [$^{35}$S]UTP at >6 mCi/ml (Amersham Corp., >1200 Ci/mmol) and 1.6 U/ml RNasin (Promega), with the remaining in vitro transcription reagents provided in a kit (SureSite, Novagen Inc.). After transcription at 37° C. for 1 hour, DNA templates are removed by a 15 minute digestion at 37° C. with 0.5 U/ml RNase-free DNase 1, extracted, and precipitated with ethanol. Riboprobes are hydrolyzed to an average final length of 150 bp by incubating in 40 mM NaHCO$_3$, 60 mM Na$_2$CO$_3$, 80 mM DTT at 60° C., according to previously determined formula. Hydrolysis is terminated by addition of sodium acetate, pH 6.0, and glacial acetic acid to 0.09 M and 0.005% (v/v), respectively, and the probes are then ethanol precipitated, dissolved in 0.1 M DTT, counted, and stored at −20° C. until use.

RNase precautions are taken in all stages of slide preparation. Bouins fixed, paraffin embedded tissue sections are heated to 65° C. for 10 minutes, deparaffinized in 3 changes of xylene for 5 minutes, and rehydrated in a descending ethanol series, ending in phosphate-buffered saline (PBS). Slides will be soaked in 0.2 N HCl for 5 min., rinsed in PBS, digested with 0.0002% proteinase K in PBS for 30 minutes at 37° C. and rinsed briefly with DEPC-treated water. After equilibrating for 3 minutes in 0.1 M triethanolamine-HCl (TEA-HCl), pH 8.0, sections are acetylated in 0.25% (v/v) acetic anhydride in 0.1 M TEA-HCl for 10 minutes at room temperature, rinsed in PBS, and dehydrated in an ascending ethanol series. Each section receives 100–200 ml prehybridization solution (0.5 mg/ml denatured RNase-free tRNA (Boehringer-Mannheim), 10 mM DTT, 5 mg/ml denatured, sulfurylated salmon sperm DNA, 50% formamide, 10% dextran sulfate, 300 mM NaCl, 1×RNase-free Denhardt's solution (made with RNase-free bovine serum albumin, Sigma), 10 mM Tris-HCl, pH 7.4, 1 mM EDTA) and then incubate on a 50° C. slide warmer in a humidified enclosure for 2 hours. The sulfurylated salmon-sperm DNA blocking reagent is used in both prehybridization and hybridization solutions to help reduce nonspecific binding to tissue by $^{35}$SH groups on the probe. It is prepared by labeling RNase-free salmon sperm DNA (Sigma) with non-radioactive α-thio-dCTP and α-thio-dATP (Amersham) in a standard random oligonucleotide-primed DNA labeling reaction. Excess prehybridization solution is removed with a brief rinse in 4×SSC before application of probe.

Riboprobes, fresh tRNA and sulilylated salmon sperm DNA will be denatured for 10 minutes at 70° C., and chilled on ice. Hybridization solution, identical to prehybridization solution except with denatured probe added to 5×10$^6$ CPM/ml, is applied and slides incubated at 50° C. overnight in sealed humidified chambers on a slide warmer. Sense and antisense probes are applied to serial sections. Slides are rinsed 3 times in 4×SSC, washed with 2×SSC, 1 mM DTT for 30 min. at 50° C., digested with RNase A (20 mg/ml RNase A, 0.5 M NaCl, 10 mM Tris, pH 8.0, 1 mM EDTA, pH 8.0) for 30 min. at 37° C., and rinsed briefly with 2×SSC, 1 mM DTT. Three additional washes are performed, each at 50° C. for minutes: once in 2×SSC, 50% formamide, 1 mM DTT, and twice in 1×SSC, 0.13% (w/v) sodium pyrophosphate, 1 mM DTT.

Slides are dehydrated in an ascending ethanol series (with supplementation of the dilute ethanols (50% and 70%) with SSC and DTT to 0.1× and 1 mM, respectively). Slides are exposed to X-ray film for 20–60 hours to visualize overall hybridization patterns, dipped in autoradiographic emulsion (Kodak NTB-2, diluted to 50% with 0.3 M ammonium acetate), slowly dried for 2 hours, and exposed (4° C.) for periods ranging from 8 days to 8 weeks. After developing emulsion, sections are counter strained with hematoxylin and eosin, dehydrated, and mounted with xylene-based medium. The hybridization signal is visualized under dark-field microscopy.

The above in situ hybridization protocol may be used, for example, in detecting the temporal and spatial pattern of PTH/PTHrP receptor expression. A suitable rat PTH/PTHrP receptor cDNA probe (R15B) is one that consists of a 1810 bp region encoding the full length rat bone PTH/PTHrP receptor (Abou-Samra et al., 1992). The cDNA fragment is. subcloned into pE-DNA 1 (Invitrogen Corp., San Diego, Calif.) and is cut out using XbaI and BamHI. This probe has provided positive signals for northern blot analysis of rat, murine, and human osteoblastic cell lines, rat primary calvarial cells, and murine bone tissue. The pcDNA I plasmid contains a T7 and SP6 promoter that facilitate the generation of cRNA probes for in situ hybridization. The full length transcript has been used to detect PTH/PTHrP receptor in sections of bone (Lee et al., 1994). The PTHrP cDNA probe (Yasuda et al., 1989) is a 400 bp subcloned fragment in pBluescript (Stratagene). This probe has been used for in situ hybridization, generating an antisense cRNA probe using BamHI cleavage and the T3 primer and a sense cRNA probe using EcoRI cleavage and the T7 primer.

8. Monoclonal Antibody Generation

Means for preparing and characterizing antibodies are well known in the art (See, e.g., Antibodies: A Laboratory Manual, Cold Spring Harbor Laboratory, 1988; incorporated herein by reference).

The methods for generating monoclonal antibodies (MAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine senun albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of boosting and titering is repeated until a suitable titer is achieved. When a desired level of immunogenicity is obtained, the immunized animal can be bled and the serum isolated and stored, and/or the animal can be used to generate MAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified LTBP-2 or LTBP-3 protein, polypeptide or peptide. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986, pp. 60–61), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). For example, where the immunized animal is a mouse, one may use P3-X63/Ag8, X63-Ag8.653, NS1/1.Ag41, Sp210-Ag14, FO, NSO/U, MPC-11, MPC11-X45-GTG1.7 and S194/5XX0 Bul; for rats, one may use R210.RCY3, Y3-Ag1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding pp. 71–74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocls the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

9. LTBP Structure and Function

The LTBPs appear to be modular polypeptides characterized by the presence of multiple cysteine-rich motifs. Molecular cloning of human LTBP-1 (Kanzaki et al., 1990) indicates, for example, that the molecule consists of 16 epidermal growth factor-like repeats with the potential to bind calcium (EGF-CB repeats), 3 copies of a unique motif containing 8 cysteine residues, an RGD motif, and an 8 amino acid motif identical to the cell binding domain of the laminin β2 chain. EGF-CB repeats may be modified to contain hydroxyaspartic acid and hydroxyasparagine (Stenflo et al., 1987). The genes that code for two LTBPs have been isolated previously. In sharp contrast to those of the prior art, the LTBP-3 sequence of the present invention shares only 40% sequence identity with those of the LTBP-1 sequence (Kanak et al., 1990) and the LTBP-2 sequence (Moren et al., 1994.

Unlike the human LTBP genes isolated previously which are localized to human chromosome 2, band p12-q22 (LTBP-1, Sternman et al., 1994) and human chromosome 14, band q24 (LTBP-2, Moren et al., 1994), the LTBP-3 of the present invention is localized to n chromosome 11, band q12.

One aspect of the present invention is the mapping of the murine LTBP-3 to mouse chromosome 19, band B, a region of conserved synteny with human chromosome 11, band While the function of LTBP is unknown (i.e., studies with transfected CHO cells indicate that LTBP does not contribute to TGF-β latency), several ideas have been proposed that, when taken together, suggest that LTBP may function as a extracellular structural protein capable of both regulating and targeting TGF-β activity. First, LTBP may regulate the intracellular biosynthesis of latent TGF-β. Cultured erythroleukemia cells efficiently assemble and secrete large latent TGF-β complexes, but they poorly secrete latent TGF-β complexes that lack LTBP-1 (Miyazono et al., 1991; 1992). The retained complexes contain anomalous disulfide bonds, suggesting that, for erythroleukemia cells at least, LTBP contributes to the normal assembly and secretion of TGF-β latent complexes. Second, LTBP may function to target latent TGF-β to specific types of connective tissue. Recent evidence suggests that the large latent TGF-β complex covalently binds the extracellular matrix via LTBP-1, i.e., LTBP-1 may target the latent TGF-β complex to a site near the cell surface (pericellular matrix) to facilitate the generation of autocrine or paracrine effects (Flaumenhaft et al., 1993; Taipale et al., 1994; Taipale and Keski-Oja, 1992). Third, LTBP may modulate the activation of latent complexes. There is direct evidence that LTBP-1 binds calcium (Colosetti et al., 1993) and that calcium binding induces a structural change that protects LTBP-1 from proteolytic attack. As described above (Lyons et al., 1988; Taipale et al., 1995), latent TGF-β is exposed to protease-rich environments during wound repair and normal development and exposure to these environments leads to the release of mature TGF-β from extracellular storage sites. It is therefore possible that the protease-resistant conformation of LTBP helps ensure TGF-β integrity in vivo.

10. LTBP and Skeletal Tissues

Skeletal tissue represents one of the largest known repositories of latent TGF-β (200 μg/kg bone; Seyedin et al., 1986; Seyedin et al., 1987). Moreover, activated TGF-β may stimulate bone formation in developing tissues and may act as a "coupling factor" that coordinates matrix resorption and formation during bone remodeling (Centrella et al., 1991). Finally, activated TGF-β may exert a powerful osteoinductive stimulus following fracture (Joyce et al., 1990; Beck et al., 1993).

It has not yet been determined if TGF-β normally exists in bone as a small or large latent complex. Previous studies (Pfeilschifter et al., 1990; Bonewald et al., 1991) have shown that the major form of TGF-β in conditioned media from bone organ cultures is a 100 kDa latent complex that lacks LTBP-1. Additionally, Dallas et at. (Dallas et al., 1994) have demonstrated that cultued MG63, ROS 17/2.8, and UMR-106 cells (derived from osteosarcomas of various types) each secrete two major forms of latent TGF-β1, namely, a 290 kDa complex that contains LTBP-1 and a 100 kDa complex lacking LTBP-1. A second high molecular weight complex that contained latent TGF-β2 and LTBP was also identified. The presence and relative amount of low and high molecular weight complexes varied with cell type, and TGF-β1 and LTBP did not appear to be co-expressed in bone cells. These results led the authors to conclude that the 100 kDa latent TGF-β complex is a physiologically important form in bone cells, i.e., LTBP did not appear to be required for the proper and efficient assembly and secretion of small latent complexes.

At the end of their paper, Dallas et al. also acknowledged that the production of small versus large latent TGF-β complexes may be associated with specific stages in the maturation of bone cells—e.g., MG63, ROS 17/2.8, and UMR-106 cells are known to express different subsets of mature osteoblast phenotypic markers, which could explain differences in the size of the latent TGF-β complexes produced by the various osteosarcoma cell lines. Along this line, the inventors' laboratory has recently shown that mouse pre-osteoblast MC3T3-E1 cells express the ltbp-3 gene at the outset of osteoblast differentiation and that the LTBP-3 polypeptide binds TGF-β1 in MC3T3-E1 conditioned media (Yin et al., 1995). Therefore, MC3T3-E1 cells express large latent TGF-β1 complexes bearing LTBP-3 precisely at the time of the pre-osteoblast to osteoblast transition (i.e., at ~day 14 in culture, or at the onset of alkaline phosphatase expression).

Extending the MC3T3-E1 data further, the inventors' laboratory has also found that ltbp-2 and ltbp-3 are co-expressed with TGF-β in developing mouse skeletal tissues (Yin et al., 1995) and that ltbp-3 (at least) is expressed at sites of osteotomy repair in vivo (Yin et al., 1994).

There is little doubt that TGF-β contributes to the normal structure and function of skeletal tissues. Bone is an abundant source of latent TGF-β, and mature TGF-β contributes to the processes of skeletal morphogenesis, bone remodeling, and bone repair. Consequently, bone must regulate the autocrine and paracrine effects of TGF-β with precision. The inventors' laboratory was the first to clone and map the mouse ltbp-2 and ltbp-3 genes, and it has obtained evidence that both genes are expressed during normal murine skeletal morphogenesis and during bone osteotomy repair. In addition, in MC3T3-E1 pre-osteoblasts TGF-β is synthesized as a homodimer known as the small-latent complex that covalently binds LTBP to form large latent complexes. These results suggest for the first time that LTBP facilitates the assembly and secretion of latent TGF-β complexes and targets latent TGF-β to bone matrix. With the availability of the ltbp-2 and ltbp-3 genes, the opportunity exists in the inventors' laboratory to gain further insight into LTBP structure and function and, in turn, the mechanism by which latent TGF-β complexes can be targeted to bone matrix and cells in a controlled manner.

Accordingly, an LTBP protein or polypeptide may be provided to a repair tissue site or bone progenitor tissue site. A nucleic acid segment (DNA or RNA) that expresses an LTBP protein or polypeptide in cells of the tissue site may be provided, as may a nucleic acid segment in association with a structural biocompatible matrix (U.S. Pat. No. 5,942,496 and U.S. Pat. No. 5,763,416).

11. Detection of LTBP-encoding DNA Segments

The amount of an LTBP-2 or LTBP-3-encoding DNA segment present within a biological sample, such as blood, serum or PBMC sample, may be determined by means of a molecular biological assay to determine the level of a nucleic acid that encodes such an LTBP-2 or LTBP-3 polypeptide, or by means of an immunoassay to determine the level of the polypeptide itself.

In a molecular biological method for detecting a cell that produces LTBP-2 or LTBP-3, one would obtain nucleic acids from one or more cells and analyze the nucleic acids to identify a nucleic acid segment that encodes LTBP-2 or LTBP-3. Such nucleic acids may be identified by length, where an appropriate assay would be a PCR™-based assay resulting in the identification of an LTBP-2 or LTBP-3-encoding mRNA transcript. Alternatively, the nucleic acid segment may be identified by sequence, which method generally includes identifying a transcript with a sequence of the present invention e.g., by Northern or Southern blotting using a discriminating probe prepared in accordance with SEQ ID NO:1 or SEQ ID NO:3.

The detection of a cell that produces LTBP-2 or LTBP-3-encoding DNA segment using a method based upon the sequence of an ltbp-2 or ltbp-3 transcript requires an ltbp-2 or ltbp-3 probe with a novel DNA sequence as disclosed herein. This imparts an evident utility to the nucleic acid segments of the present invention, particularly the shorter ones.

The presence of a substantially complementary nucleic acid sequence in a sample, or a significantly increased level of such a sequence in comparison to the levels in a normal or "control" sample, will thus be indicative of a sample that contains a cell that harbors an LTBP-2 or LTBP-3-encoding DNA segment. Here, substantially complementary LTBP-2 or LTBP-3-encoding nucleic acid sequences are those that have relatively little sequence divergence and that are capable of hybridizing under relatively stringent conditions, as discussed above.

A variety of hybridization techniques and systems are known that can be used in connection with the detection aspects of the invention, including diagnostic assays such as those described in Falkow et al., U.S. Pat. No. 4,358,535. Short coding or non-coding nucleic acid segment probes may also be employed as primers in connection with diagnostic PCR™ technology, as well as for use in any of a number of other PCR™ applications, including PCR™-based cloning and engineering protocols.

In general, the "detection" of an LTBP-2 or LTBP-3-encoding DNA segment is accomplished by attaching or incorporating a detectable label into the nucleic acid segment used as a probe and "contacting" a sample with the labeled probe. In such processes, an effective amount of a nucleic acid segment that comprises a detectable label (a probe), is brought into direct juxtaposition with a composition containing target nucleic acids. Hybridized nucleic acid complexes may then be identified by detecting the presence of the label, for example, by detecting a radio, enzymatic, fluorescent, or even chemiluminescent label.

Many suitable variations of hybridization technology are available for use in the detection of nucleic acids, as will be known to those of skill in the art. These include, for example, in situ hybridization, Southern blotting and Northern blotting. In situ hybridization describes the techniques wherein the target nucleic acids contacted with the probe sequences are those located within one or more cells, such as cells within a clinical sample or even cells grown in tissue culture. As is well known in the art, the cells are prepared for hybridization by fixation, e.g., chemical fixation, and placed in conditions that allow for the hybridization of a detectable probe with nucleic acids located within the fixed cell.

Alternatively, target nucleic acids may be separated from a cell or sample prior to contact with a probe. Any of the wide variety of methods for isolating target nucleic acids may be employed, such as cesium chloride gradient centrifugation, chromatography (e.g., ion, affinity, magnetic), phenol extraction and the like. Most often, the isolated nucleic acids will be separated, e.g., by size, using electrophoretic separation, followed by immobilization onto a solid matrix, prior to contact with the labelled probe. These prior separation techniques are frequently employed in the art and are generally encompassed by the terms "Southern blotting" and "Northern blotting". Although the execution of various techniques using labeled probes to detect LTBP-2 or LTBP-3-encoding DNA or RNA sequences in clinical samples are well known to those of skill in the art, a particularly preferred method is described in detail herein, in Examples 1 and 3.

Kits for use in Southern and Northern blotting to identify LTBP-2 or LTBP-3-encoding DNA segments are also contemplated to fall within the scope of the present into invention. Such kits will generally comprise, in suitable container means, ltbp-2 or ltbp-3 nucleic acid probes; unrelated probes for use as controls; and optionally, one or more restriction enzymes.

12. Construction of Chimeric Promoter-reporter Expression Plasmids

Using the 5' upstream flanking sequence of the LTBP-2 and LTBP-3 genes, a series of restriction fragments from available phage genomic inserts may be generated and subcloned into a promoter-reporter expression plasmid. An example of such a vector is pGL3, a luciferase reporter vector (Promega), which has a strong 5' terminator of transcription, a multiple cloning site, the cDNA coding sequence of insect luciferase, a strong translation stop codon, and an intron/polyadenylation signal sequence derived from SV40.

By assembling 9–15 overlapping promoter-reporter expression plasmids that cover an about 5 kb region of interest, the identification of potential cis-acting elements is contemplated. Once the initial constructs have been characterized, regions of 5' upstream flanking sequence that show strong promotion (or repression) of gene expression may be studied in careful detail.

The Northern analysis and tissue in situ hybridization data presented herein suggest that ltbp-3 is highly expressed in developing mouse tissues. Additionally, the ltbp-3 transcript appears to be highly expressed by MC3T3-E1 cells in culture. The structural features of this sequence are consistent with a so-called housekeeping gene, i.e., a TATA-less and CAATT-less promoter sequence that is 70% GC-rich.

To overcome potential problems of low reporter gene expression, the inventors contemplate the use of pEU-CAT, a promoter-less CAT vector especially constructed for the analysis of weak promoters (Harduin-Lepers et al., 1993). Alternatively, modifying the reporter constructs by the addition of an ltbp-3 enhancer element is also contemplated to be useful.

13. Evaluating Promoter Function

Promoter function may be evaluated by in vitro transfection studies using L cells or NIH3T3 cells, since they have been used successfully for this purpose. An interesting alternative is to use Drosophila SL12 cells which: lack the trans-acting factor, Sp1; co-transfection of SL12 cells with a plasmid encoding the Sp1 protein such as $pP_{ac}Sp1$ and a reporter construct containing putative Sp1 binding sites will result in reporter expression if the sites are functional (Courey and Tjian, 1988). L cell transfection is performed using standard protocols (Sambrook et al., 1989). Briefly, subconfluent cells (covering ~20% of a 100 mm plastic tissue culture dish) are washed 2× in DMEM tissue culture medium (GIBCO) and then incubated for 3 hrs. at 37° C. in a sterile mixture of DEAE-dextran (0.25 mg/ml), chloroquine (55 mg/ml), and 15 µg plasmid DNA (Courey and Tjian, 1988). Cells are then shocked by incubation with 10% DMSO in sterile PBS for 2 min. at 37° C., washed 2× with DMEM (Sambrook et al., 1989), and incubated in DMEM plus 10% fetal calf serum and antibiotics for 72 hr. at 37° C. Since DEAE-dextran is quite toxic to NIH3T3 cells, these cells may be transfected by electroporation.]

Using the pGL3 reporter/expression vector, luciferase activity may be measured in cell lysates using Luciferase Assay System kit reagents (Promega) according to protocols provided by the manufacturer. To measure background CPM, 20 µl of cell lysate is added to a clean microcentrifuge tube and light activity is measured in a scintillation counter (System 1400 scintillation counter, Wallac Nuclear; all channels open). The same procedure is used to measure background CPM of 100 µl luciferase substrate stock solution. Once the background CPM have been documented, homogenate and substrate are mixed and light emission is measured immediately. Enzyme activity values are routinely obtained in triplicate, normalized to 1 mg of total protein, and expressed as a mean value ± the standard deviation. Student's t test is used to determine statistical significance of differences among groups (95% confidence level).

In one study, following transfection of COS cells with the pGL3 luciferase expression plasmid, an aliquot of a cell homogenate was assayed for enzyme activity using commercially available kits and according to the manufacturer's recommendations. An equal aliquot of a cell homogenate prepared from untransfected COS served as a negative control. Significant luciferase activity was found only in the homogenate from transfected cells.

14. Biological Functional Equivalents

As mentioned above, modification and changes may be made in the structure of an osteotropic gene and still obtain a functional molecule that encodes a protein or polypeptide with desirable characteristics. The following is a discussion based upon changing the amino acids of a protein to create an equivalent, or even an improved, second-generation molecule. The amino acid changes may be achieved by changing the codons of the DNA sequence, according to the following codon table:

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the DNA sequences of osteotropic genes without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: Isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ii are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Isolation of a Novel Latent TGF-β Binding Protein-like LTBP-3 Gene

The TGF-βs represent a family of structurally related molecules with diverse effects on mammalian cell shape, growth, and differentiation (Roberts and Sporn, 1990). Initially synthesized as a precursor consisting of an amino-terminal propeptide followed by mature TGF-β, two chains of nascent pro-TGF-β associate in most tissues to form a Mr ~106,000 inactive disulfide-bonded dinier. Homodimers are most common, but heterodimers have also been described (Cheifetz et al., 1987; Ogawa et al., 1992). During biosynthesis the mature TGF-β dimer is cleaved from the propeptide dimer. TGF-β latency results in part from the non-covalent association of propeptide and mature TGF-β dimers (Pircher et al., 1984 and 1986; Wakefield et al., 1987; Millan et al., 1992; see also Miyazono and Heldin, 1989). Consequently, the propeptide dimer is often referred to as the latency associated protein (LAP), and LAP plus the disulfide-bonded TGF-β dimer are also known as the small latent complex. In the extracellular space small latent complexes must be dissociated to activate mature TGF-β. The mechanism of activation of the latent complex is thought to be one of the most important steps governing TGF-β effects (Lyons et al., 1988; Antonelli-Orlidge et al., 1989; Twardzik et al., 1990; Sato et al., 1993).

In certain lines of cultured cells small latent growth factor complexes may contain additional high molecular weight proteins. The best characterized of these high molecular weight proteins is the latent TGF-β binding protein, or LTBP (Miyazono et al., 1988; Kanzaki et al., 1990; Tsuji et al., 1990; Olofsson et al., 1992; Taketazu et al., 1994). LTBP produced by different cell types is heterogeneous in size, perhaps because of alternative splicing or because of tissue-specific proteolytic processing (Miyazono et al., 1988; Wakefield et al., 1988; Kanzaki et al., 1990; Tsuji et al., 1990). Latent TGF-β complexes that contain LTBP are known as large latent complexes. LTBP has no known covalent linkage to mature TGF-β, but rather it is linked by a disulfide bond to LAP.

Two LTBPs have been isolated to date. The deduced human LTBP-1 amino acid sequence is comprised of a signal peptide, 16 epidermal growth factor-like repeats with the potential to bind calcium (EGF-CB repeats), 2 copies of a unique motif containing 8 cysteine residues, an RGD cell attachment motif, and an 8 amino acid motif identical to the cell binding domain of the laminin B2 chain (Kanzaki et al., 1990). There is evidence that LTBP-1 binds calcium, which, in turn, induces a structural change that protects LTBP from proteolytic attack (Colosetti et al., 1993). LTBP-2 shows 41% sequence identity to LTBP-1, and its structural domains show a similar overall organization (Moren et al., 1994).

While the functions of LTBP-1 and LTBP-2 presently are unknown, several ideas have been put forward in the literature. First, LTBP may regulate the intracellular biosynthesis of latent TGF-β precursors. Cultured eyythroleukemia cells efficiently assemble and secrete large latent TGF-β complexes, whereas they slowly secrete small latent TGF-β complexes that contain anomalous disulfide bonds (Miyazono et al., 1991; 1992). Therefore, LTBP may facilitate the normal assembly and secretion of latent TGF-β complexes. Second, LTBP may target latent TGF-β to specific types of connective tissue. Recent evidence suggests that the large latent TGF-β complex is covalently bound to the extracellular matrix via LTBP (Taipale et al., 1994). Based on these observations, LTBP has been referred to as a "matrix receptor", i.e. a secreted protein that targets and stores latent growth factors such as TGF-β to the extracellular matrix. Third, LTBP may modulate the activation of latent complexes. This idea is based in part on recent evidence which suggests that mature TGF-β is released from extracellular storage sites by proteases such as plasmin and thrombin and that LTBP may protect small latent complexes from proteolytic attack (Falcone et al., 1993; Benezra et al., 1993; Taipale et al., 1994), i.e. protease activity may govern the effect of TGF-β in tissues, but LTBP may modulate this activity. Fourth, LTBP may plays an important role in targeting the latent TGF-β complex to the cell surface, allowing latent TGF-β to be efficiently activated (Flaumenhaft et al., 1993).

A. Materials and Methods 1. cDNA Cloning

Aliquots (typically 40–50,000 PFU) of phage particles from a cDNA-library in the λZAPII® vector made from NIH3T3 cell mRNA (Stratagene) and fresh overnight XL1-Blue™ cells (grown in biria broth supplemented with 0.4% maltose in 10 mM $MgSO_4$) were mixed, incubated for 15 min. at 37° C., mixed again with 9 ml of liquid (50° C.) top layer agarose (NZY broth plus 0.75% agarose), and then spread evenly onto freshly poured 150 mm NZY-agar plates. Standard methods were used for the preparation of plaque-lifts and filter hybridization (42° C., in buffer containing 50% formamide, 5×SSPE, 1×Denhardt's, 0.1% SDS, 100 mg/ml salmon sperm DNA, 100 mg/ml heparin). Filters were washed progressively to high stringency (0.1×SSC/0.1% SDS, 65° C.). cDNA probes were radiolabeled by the nick translation method using commercially available reagents and protocols (Nick Translation Kit, Boehringer Mannheim). Purified phage clones were converted to pBluescript plasmid clones, which were sequenced using Sequenase (v2.0) as described (Chen et al., 1993; Yin et al., 1995). Sequence alignment and identity was determined using sequence analysis programs from the Genetics Computer Group (MacVector).

2. Tissue In Situ Hybridization

To prepare normal sense and antisense probes, a unique 342 bp fragment from the 3' untranslated region (+3973 to +4314, counting the "A" of the initiator Met codon as +1; see "ish", FIG. 1) was subcloned into the pBSKS +plasmid (Stratagene, Inc.). Template DNA was linearized with either EcoRI or BamHI, extracted, and precipitated with ethanol. Sense and antisense transcripts were generated from 1 mg template with T3 and T7 polymerases in the presence of [$^{35}$S]UTP at >6 mCi/ml (Amersham, >1200 Ci/mmol) and 1.6 U/ml RNasin (Promega), with the remaining in vitro transcription reagents provided in a kit (SureSite, Novagen Inc.). After transcription at 37° C. for 1 h, DNA templates were removed by a 15 min. digest at 37° C. with 0.5 U/ml RNase-free DNase I, extracted, and precipitated with ethanol. Riboprobes were hydrolyzed to an average final length of 150 bp by incubating in 40 mM $NaHCO_3$, 60 mM $N_2CO_3$, 80 mM DTT for ~40 min. at 60° C. Hydrolysis was terminated by addition of sodium acetate, pH 6.0, and glacial acetic acid to 0.09 M and 0.56% (v/v), respectively, and the probes were then ethanol precipitated, dissolved in 0.1 M DTT, counted, and stored at −20° C. until use. Day 8.5–9.0, day 13.5, and day 16.5 mouse embryo tissue sections (Novagen) and the in situ hybridization protocol were exactly as described (Chen et al, 1993; Yin et al., 1995).

3. Northern Analysis

MC3T3-E1 cell poly(A+) RNA (2–10 mg aliquots) was electrophoresed on a 1.25% agarose/2.2 M formaldehyde gel and then transferred to a nylon membrane (Hybond-N, Amersham). The RNA was cross-linked to the membrane by exposure to a UV light source ($1.2 \times 10^6$ mJ/cm$^2$, UV Stratalinker 2400, Stratagene) and then pre-hybridized for >15 min. at 65° C. in Rapid-Hyb buffer (Amersham, Inc.). A specific cDNA probe consisting solely of untranslated sequence from the 3' end of the transcript was $^{32}$P-labeled by random priming and used for hybridization (2 h at 65° C.). Blots were washed progressively to high stringency (0.1× SSC/0.1% SDS, 65° C.), and then placed against x-ray film with intensifying screens (XAR, Kodak) at −86° C.

4. Antibody Preparation

LTBP-3 antibodies were raised against a unique peptide sequence found in domain #2 (amino acids 155–167). Peptide #274 (GESVASKHAIYAVC) (SEQ ID NO:5) was synthesized using an ABI model 431A synthesizer employing FastMoc chemistry. The sequence was confirmed using an ABI473 protein sequencer. A cysteine residue was added to the carboxy-terminus to facilitate crosslinking to carrier proteins. For antibody production, the synthetic peptide was coupled to rabbit serum albumin (RSA) using MBS (m-maleimidobenzoic acid-N-hydroxysuccinimide ester) at a substitution of 7.5 mg peptide per mg of RSA. One mg of the peptide-RSA conjugate in 1 ml of Freund's complete adjuvant was injected subcutaneously at 10 different sites along the backs of rabbits. Beginning at 3 weeks after initial immunization, the rabbits were given bi-weekly booster injections of 1 mg peptide-RSA in 100 ul of Freund's incomplete adjuvant. IgG was prepared by mixing immune serum with caprylic acid (0.7 ml caprylic acid per ml serum), stirring for 30 min., and centrifuging at 5,000×g, for 10 min. The supernatant was decanted and dialyzed against two changes of phosphate buffered saline (PBS) overnight at 4° C. The antibody solution was then affinity purified by passing it over a column containing the immunizing peptide coupled to Affi-gel 10 affinity support. Bound antibodies were eluted with 0.2 M glycine (pH 2.3), immediately dialyzed against PBS, and concentrated to 1 mg/ml. prior to storage at −70° C.

5. Transfection

Transient transfection was performed using standard protocols (Sambrook et al., 1989). Briefly, subconfluent cells (covering ~20% of a 100 mm plastic tissue culture dish) were washed 2× in DMEM tissue culture medium (GIBCO) and then incubated for 3 hrs. at 37° C. in a sterile mixture of DEAE-dextran (0.25 mg/ml), chloroquine (55 mg/ml), and 15 mg plasmid DNA (Courey and Tjian, 1988). Cells then were shocked by incubation with 10% DMSO in sterile PBS for 2 min. at 37° C., washed 2× with DMEM (Sambrook et al., 1989), and incubated in DMEM plus 10% fetal calf serum and antibiotics for 72 hr. at 37° C.

6. Immunoprecipitation

For immunoprecipitation, 1 ml of antibody (1:400 final concentration, in PBS-TDS buffer: 0.38 mM NaCl, 2.7 mM KCl, 8.1 mM $Na_2HPO_4$, 1.5 mM $KH_2PO_4$, 1% Triton X-100, 0.5% Deoxycholic acid, and 0.1% SDS) was added to 1 ml of radiolabeled medium proteins. The mixture was incubated with shaking at 4° C. for 1 hr., protein A-sepharose CL-4B beads were added (200 ml, 10% suspension), and this mixture was incubated with shaking for one additional hour at 4° C. Immunoprecipitated proteins were pelleted by brief centrifugation, the pellet was washed 6× with PBS-TDS buffer, 2×protein loading dye was added, and the samples were boiled for 5 min. and then fractionated on 4–18% gradient SDS-PAGE (Bonadio et al., 1985). Cold molecular weight markers (200 kDa–14.3 kDa, Rainbow mix, Amersham) were used to estimate molecular weight. The gel was dried and exposed to film for the indicated time at room temperature.

7. Western Analysis

Fractionated proteins within SDS-polyacrylamide gels were transferred to a nitrocellulose filter for 2 hours using Tris-glycine-methanol buffer, pH 8.3 at 0.5 mA/cm$^2$. The filter was blocked, incubated with nonfat milk plus antibody (1:1000 dilution) for 2 hr, and washed. Antibody staining was visualized using the ECL Western blotting reagent (Amersham) according to the manufacturer's protocols.

B. Results

In this study, the inventors isolated and characterized a novel murine fibrillin-like cDNA encoding LTBP-3. To clone the murine LTBP-3 gene, cDNA from a 3T3 cell cDNA library was amplified using human fibrillin-1 PCR™ primers under low stringency conditions (i.e., annealing at 37° C. initially for 10 cycles, followed by annealing at 60° C. for cycles). The results indicated that a murine DNA fragment of unexpectedly low homology (~50%) to human fibrillin-1 was obtained. Molecular cloning of the authentic murine fibrillin-1 transcript was also performed, confirming the human and murine fibrillin-1 coding sequences share >95% sequence identity. The murine fibrillin-1 and PCR™ sequences were different, which suggested that the PCR™ product may have been derived from a related, fibrillin-like cDNA. The 3T3 cell cDNA library was screened at high stringency using the murine PCR™ product as the probe in order to test this hypothesis. A cDNA walking strategy eventually yielded seven overlapping cDNA clones (FIG. 1). It provides a unique mRNA of 4,314 nucleotides, with an open reading frame of 3,753 nucleotides (SEQ ID NO:3). The deduced molecule is a unique polypeptide of 1,251 amino acids (SEQ ID NO:4). Excluding the signal peptide (21 amino acids), the novel fibrillin-like molecule consists of five structurally distinct regions (Region 1–Region 5), and although similar to murine fibrillin-1 (FIG. 2A), its domain structure is unique as is evidenced by the schematic representation of LTBP-3 shown in FIG. 2B.

Domain #1 is a 28 amino acid segment with a net basic charge (est pI, 12.36) that may allow for binding acidic molecules in the extracellular matrix (e.g., acidic proteoglycans). Sequences rich in basic amino acids may also function as endoproteolytic processing signals (Barr, 1991; Steiner et al., 1992), which suggests that the $NH_2$-terminus may be proteolytically processed. Domain #2 extends for 390 amino acids, consisting of an EGF-like repeat, a 135 amino acid segment that was proline-rich (20.7%) and glycine-rich (11.8%) but not cysteine-rich, a Fibmotif (ereira et al., 1993), an EGF-CB repeat, and a TGF-bp repeat. Domain #3 is a 113 amino acid segment characterized by its high proline content (21%). Domain #4 extends for 678 amino acids and consists of 14 consecutive cysteine-rich repeats. Based on structural homologies, 12/14 repeats were epidermal growth factor-calcium binding (EGF-CB) motifs (Handford et al., 1991), whereas 2/14 were transforming growth factor-β-binding protein (TGF-bp) motifs (Kanzaki et al., 1990). Finally, domain #5 is a 22 amino acid segment at the carboxy-terminus. The conceptual amino acid sequence encoded by the open reading frame consisted of 1,251 amino acids (FIG. 2B) with an estimated pI of 5.92, a predicted molecular mass of 134,710 Da, and five potential N-linked glycosylation sites. No RGD sequence was present.

Northern blot analysis of murine embryo RNA using a 3' untranslated region probe identified a transcript band of ~4.6 kb. In this regard, 4,310 nt have been isolated by cDNA cloning, including a 3' untranslated region of 401 nt and a 5' upstream sequence of 156 nt. The apparent discrepancy between the Northern analysis result and the cDNA sequence analysis suggested that the 5' upstream sequence may include ~300 nt of additional upstream sequence. This estimate was consistent with preliminary primer extension mapping studies indicating that the 5' upstream sequence is 400–500 nt in length.

A total of 19 cysteine-rich repeats were found in domains #2 and #4 of the murine LTBP-like (LTBP-3) polypeptide. Thirteen were EGF-like and 11/13 contained the calcium binding consensus sequence. This consensus was derived from an analysis of 154 EGF-CB repeats in 23 different proteins and from structural analyses of the EGF-CB repeat, both bound and unbound to calcium ion (Selander-Sunnerhagen et al., 1992). Variations on the consensus have been noted previously and one of these, D-L-N/D-E-$C_1$, was identified in the third EGF-like repeat of domain #4. In addition, a potential calcium binding sequence which has not previously been reported (E-T-N/D-E-$C_1$) was identified in the first EGF-like repeat of domain #4. Ten of thirteen EGF-CB repeats also contained a second consensus sequence which represents a recognition sequence for an Asp/Asn hydroxylase that co- and post-translationally modifies D/N residues (Stenflo et al., 1987; Gronke et al., 1989).

Although about one-half the size, the deduced polypeptide was organized like fibrillin-1 in that it consisted of a signal peptide followed by 5 structurally distinct domains, i.e., two domains with numerous EGF-like, EGF-CB and Fib repeats and a third with a proline-rich sequence (Pereira et al., 1993). However, comparison of each of these domains using the GAP and BESTFIT programs (Genetics Computer Group) has revealed a low level of amino acid homology of only 27% over the five structural domains shared by the deduced murine polypeptide and human fibrillin-2. These values are low for a putative fibrillin family member because fibrillin-1 and fibrillin-2 share ~50% identity (Zhang et al., 1994).

Figure 2A:
FIG. 2A. A schematic showing the structure of the murine fibrillin-1 gene product. Structural domains are shown below the diagram. Symbols designating various structural elements are defined in the legend to FIG. 2B.
Figure 2B:
FIG. 2B. A schematic showing the structure of the murine LTBP-like (LTBP-2 or LTBP-3) molecule. Domains #1–5 are denoted below the diagram. Symbols designate the following structural elements: EGF-CB repeats: open rectangles; TGF-bp repeats: open ovals; Fib motif: open circle; TGF-bp-like repeat: patterned oval; cysteine-rich sequences: patterned rectangles; proline/glycine-rich region: thick curved line, domain #2; proline-rich region, thick curved line, domain #3. Note that symbols designating the signal peptide have been deleted for simplicity. Additionally, the schematic assumes that EGF-like and EGF-CB repeats may extend for several amino acids beyond the $C_6$ position.
Figure 2C:
FIG. 2C. A schematic showing the structure of human LTBP-1. Domains #1–5 are denoted below the diagram. The symbols designating the structural elements are defined in the legend to FIG. 2B.

A search of available databases revealed that the deduced murine polypeptide was most similar to the human and rat latent TGF-β binding proteins (Kanzaki et al., 1990; Tsuji et al., 1990). In this regard LTBP-3 was found to be similar to fibrillin in that it could also be divided into five structurally distinct domains (FIG. 2A, FIG. 2B, and FIG. 2C). These include a relatively short domain downstream of the signal peptide with a net basic charge (amino acids 21–33, est. pI, 11.14); a domain consisting of EGF-like, EGF-CB, TGF-bp, and Fib motifs plus a proline-rich and glycine-rich sequence (amino acids 34–407); a proline-rich domain (amino acids 408–545); a large, domain consisting of EGF-CB, TGF-bp, and TGF-bp-like repeat motifs (amino acids 546–1379); and a relatively short domain at the carboxy terminus (amino acids 1380–1394). Amino acid sequence comparison of the deduced murine and human polypeptides shows 60% identity for domain #1, 52% identity for domain #2, 30% identity for domain #3, 43% identity for domain #4, and 7% identity for domain #5. The average identity over the five domains shared by the murine polypeptide and human LTBP was 38.4%. Significantly, cysteine residues in both polypeptide sequences were highly conserved.

The fibrillins are exclusively expressed by connective cells in developing tissues (Zhang et al., 1994), whereas LTBP should be expressed along with TGF-β by both epithelial and connective cells (Tsuji et al., 1990). The structural homology data therefore predict that the murine LTBP-3 gene shown in FIG. 2B should be expressed by both epithelial and connective tissue cells. Tissue in situ hybridization was used to test this hypothesis.

An overview of the expression pattern as determined by tissue in situ hybridization is presented in FIG. 3A, FIG. 3B, FIG. 3C, FIG. 3D, FIG. 3E and FIG. 3F.

Approximate mid-sagittal sections of normal murine embryos at days 8.5–9.0, 13.5 and 16.5 p.c. of development were hybridized with a $^{35}$S-labeled single stranded normal sense riboprobe from the same cDNA construct was used. At day 8.5–9.0 of development, intense gene expression was observed in the mesometrial and anti-mesometrial uterine tissues, ectoplacental cone, placenta, placental membranes. The transcript appeared to be widely expressed in murine embryo mesenchymal/connective tissue compartments, including the facial mesenchyme, at days 8.5–9.0, 13.5 and 16.5 of development. Particularly intense expression of the transcript was noted in the liver.

Microscopy of day 8.5–9.0 embryos confirmed the widespread expression of the murine gene by mesenchymal cells. Significant expression of the transcript by cells of the developing central nervous system, somites and cardiovascular tissue (myocardium plus endocardium) was also observed.

Microscopy of day 13.5 and day 16.5 embryos demonstrated expression of the murine gene by skeletal muscle cells and by cells involved in intramembranous and endochondral bone formation. The transcript was expressed by osteoblasts and by periosteal cells of the calvarium, mandible and maxilla. The transcript was also identified in both cartilage and bone of the lower extremity. A positive signal was detected in perichondrial cells and chondrocytes (proliferating>mature>hypertrophic) of articular cartilage, the presumptive growth plate, and the cartilage model within the central canal. The positive signal was also expressed by blood vessel endothelial cells within the mid-diaphysis, and the surrounding muscle cells.

Respiratory epithelial cells lining developing small airways and connective tissue cells in the pulmonary interstitium expressed the murine transcript, as did myocardial cells (atria and ventricles) and endocardial cushion tissue. Cells within the walls of large arteries also expressed the transcript. Expression of the murine gene was identified in several organs of the alimentary system, including the tongue, esophagus, stomach, small and large intestine, pancreas and liver. Mucosal epithelial cells lining the upper and lower digestive tract plus the smooth muscle and connective tissue cells found in the submucosa expressed the transcript, as did acinar cells of the exocrine pancreas. Despite the high level of transcript expression in the liver, these results suggest both cell populations express the LTBP-3 transcript.

In the kidney, expression above the basal level was observed in cells of developing nephrons, the ureteric bud, kidney blastema and the kidney interstitium. In the skin, epidermal and adnexal keratinocytes, dermal connective tissue cells, and brown fat cells within the dorsal subcutis expressed the murine transcript. In the central and peripheral nervous systems, ganglion cells within the cerebrum, brainstem, spinal cord, and peripheral nerves expressed the murine transcript. The transcript was also intensely expressed by cells of the developing murine retina.

Thus, the murine gene is widely expressed by both epithelial and connective tissue cells, a pattern that would be expected for a latent TGF-β binding protein. Three final observations argue that the LTBP-like (LTBP-3) sequence presented herein is not simply the murine homologue of human LTBP. First, domain #4 of the murine LTBP-like (LTBP-3) sequence has a smaller number of EGF-Like repeat motifs than human and rat LTBP (8 versus 11). Second, portions of the human and rat LTBP-like coding sequence were characterized and found to share ~90% identity with human and rat LTBP but only 65% identity with the murine LTBP-like gene. Third, the human LTBP and LTBP-like genes are localized to separate chromosomes. Human LTBP was assigned to human chromosome 2 based on the analysis of human x rodent somatic cell hybrid lines (Stenman et al., 1994). The present invention represents the first mapping of an LTBP gene in the murine. The human LTBP-like genes was recently localized to chromosome 11 band q12, while the murine gene was mapped to murine chromosome 19, band B (a region of conserved synteny), using several independent approaches, including fluorescent in situ hybridization.

The first indication of alternative splicing came from molecular cloning studies in the murine, in which independent cDNA clones were isolated with a deletion of 51 bp from the coding sequence. PCR™/Southern blot analysis provided additional evidence that the homologous 51 bp sequence was alternatively spliced in normal murine embryo tissues.

Northern blot analysis also demonstrated that the novel fibrillin gene was also expressed in rat callus three weeks after osteotomy, after mineralization has begun. Gene expression in normal adult rat bone tissue was insignificant, which suggests that microfibrils are an important part of the bone fracture healing response. The novel fibrillin-like gene was expressed in callus as a pair of alternatively spliced transcripts. This result has been independently reproduced on three occasions. Molecular cloning of the novel fibrillin gene in both murine and rat has identified potential splice junction sites for the alternative splicing event.

MC3T3-E1 murine pre-osteoblasts were used to demonstrate that the murine gene product was capable of binding TGF-β. MC3T3-E1 cells were utilized because they synthesize and secrete TGF-β, which may act as an autocrine regulator of osteoblast proliferation (Amarnani et al., 1993; Van Vlasselaer et al., 1994; Lopez-Casillas et al., 1994).

Figure 4:
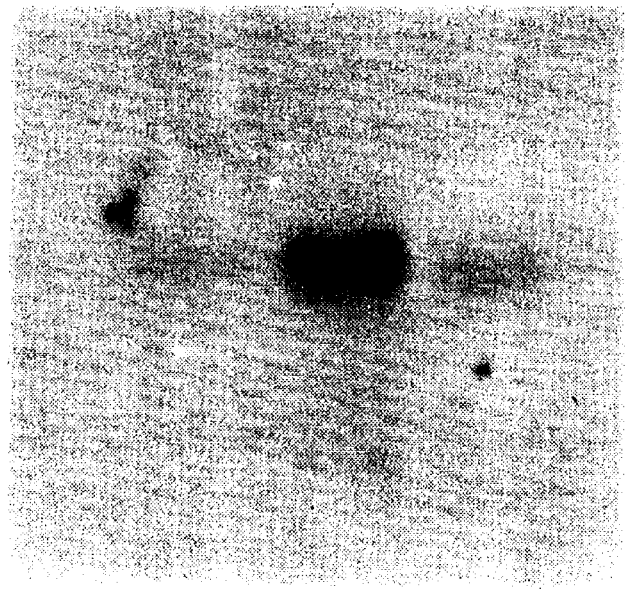
FIG. 4. Time-dependent expression of the LTBP-3 gene by MC3T3-E1 cells. mRNA preparation and Northern blotting were preformed as described in Example XIV. Equal aliquots of total RNA as determined by UV spectroscopy were loaded in each lane of the Northern gel. As demonstrated by UV spectroscopy were loaded in each lane of the Northern gel. As demonstrated by methylene blue staining (Sambrook et al., 1989), equal amounts of RNA were transferred to the nylon membrane. The results demonstrate a clear, strong peak in LTBP-3 gene expression by 14 days in culture. Weaker signals denoting LTBP-3 gene expression also can be observed after 5 days and 28 days in culture.

To determine whether or not MC3T3-E1 cells co-expressed the murine gene product of TGF-β, cells were plated on 100-mm dishes under differentiating conditions (Quarles et al., 1992) and the medium was replaced twice weekly. Parallel dishes were plated and assayed for cell number and alkaline phosphatase activity, which confirmed that osteoblast differentiation was indeed taking place. Equal aliquots of total cellular RNA was prepared from these MC3T3-E1 cells after 5, 14 and 28 days in culture for Northern blot analysis. As shown in FIG. 4, expression of the new murine gene peaked on day 14 of culture. Since MC3T3-E1 cells also show a peak in alkaline phosphatase activity on day 14 of culture (Quarles et al., 1992), the results suggest for the first time that LTBP-3 gene expression is an early marker of osteoblast differentiation.

C. Discussion

This study reports the molecular cloning of a novel LTBP-3 gene that contains numerous EGF-like repeats. Northern analysis indicates that the gene encodes a single transcript of ~4.6 kb in murine embryo tissues. The deduced amino acid sequence of the murine gene product appears to be a secreted polypeptide of 1,251 amino acids. Although it is similar to fibrillin, the overall structural organization and expression pattern of this gene product most resembles LTBP, a latent TGF-β binding protein that was originally isolated and characterized by Heldin and co-workers (Kanzaki et al., 1990). Several observations strongly suggest that LTBP and the murine LTBP-like gene product are therefore derived from related but distinct genetic loci. First, LTBP and the LTBP-like coding sequence share ~40% identity and differences exist in the number of EGF-CB repeats in the deduced polypeptide sequence of the two molecules. Second, a portion of the murine LTBP gene has been cloned and shown to share ~90% identity with human and rat LTBP. Conversely, portions of the human and rat LTBP-like genes have been cloned and shown to share ~90% identity with the murine LTBP-like gene. Third, LTBP and the LTBP-like gene reside on different human chromosomes (Stenman et al., 1994). Taken together, these data suggest that a family of at least two LTBP genes exists.

Similarities in the structural organization of LTBP-1 and the fibrillin-1 and fibrillin-2 polypeptides have been noted previously (Pereira et al., 1993; Thang et al., 1994; Taipale et al., 1994). For example, LTBP-1 and the fibrillins are all secreted extracellular matrix constituents. Moreover, each polypeptide can be organized into five domains, two of which consists predominantly of EGF-CB and TGF-bp repeat motifs. LTBP-1 and fibrillin-1 also share a domain that is proline-rich, and LTBP possesses an 8-cysteine repeat previously referred to as the "Fib motif" because it was assumed to be unique to fibrillin (Pereira et al., 1993). These similarities likely explain the initial isolation and cloning of the LTBP-3 PCR™ product, especially since the human oligonucleotide primers used to initially amplify murine cDNA were designed to direct the synthesis of an EGF-CB repeat in domain #4.

Another point of distinction between LTBP-3 and fibrillin concerns the spacing of conserved cysteines C4 and C5 in EGF-like repeats. Fibrillin-1 and fibrillin-2 each contain >50 such repeats, and in every one the spacing is $C_4$-X-$C_5$. While this pattern is repeated in a majority of the EGF-like repeats in LTBP-1 and LTBP-2, both genes also contain repeats with the spacing $C_4$-X-X-$C_5$. Although the significance of this observation is unclear, variation in the number of amino acids between $C_4$ and $C_5$ would not be expected to alter the function of the EGF-like repeat. Mature EGF is a 48 amino acid secreted polypeptide consisting of two subdomains that have few interdomain contacts (Engel, 1989; Davis, 1990). The larger $NH_2$-terminal subdomain consists of residues 1–32 and is stabilized by a pair of disulfide bonds ($C_1$–$C_3$ and $C_2$–$C_4$), whereas the smaller COOH-terminal subdomain (amino acids 33–48) is stabilized by a single disulfide bond ($C_5$–$C_6$). The COOH-terminal subdomain has a highly conserved conformation that only is possible if certain residues and the distances between them are well conserved, while conformation-sequence requirements for the NH2-terminal subdomain are relatively relaxed. Variation in $C_4$–$C_5$ spacing would not be expected to alter conformation because these residues do not normally form a disulfide bond and the spacing variation occurs at the interface of subdomains that would not be predicted to interact. The loning of additional genes will decide whether variation in $C_4$–$C_5$ spacing is a reliable discriminator between members of the LTBP and fibrillin gene families.

The LTBP-3 gene is expressed more widely during development than fibrillin-1 or fibrillin-2. Studies in developing murine tissues have shown that the Fbn-1 gene is expressed by mesenchymal cells of developing connective tissue, whereas the murine LTBP-like gene is intensely expressed by epithelial, parenchymal and stromal cells. Earlier reports have suggested that TGF-β plays a role in differentiation and morphogenesis during murine development (Lyons and Moses, 1990), when TGF-β is produced by epithelial, parenchymal and stromal cells. Tsuji et al., (1990) and others have suggested that the expression of TGF-β binding proteins should mirror that of TGF-β itself; the expression pattern of the LTBP-3 gene over the course of murine development is consistent with this expectation. However, the LTBP-3 gene may not be completely co-regulated with TGF-β. TGF-β gene and protein expression during murine development has been surveyed extensively (Heine et al., 1987; Lehnert and Akhurst, 1988; Pelton et al., 1989; Pelton et al., 1990a, b; Milian et al., 1991); these studies have not identified expression by skeletal muscle cells, chondrocytes, hepatocytes, ganglion cells, mucosal cells lining the gut, and epithelial cells of developing nephrons. It is conceivable that the LTBP-3 molecule has an additional function in certain connective tissues besides targeting TGF-β.

The binding properties of the LTBP-3 gene product are under investigation. Formally, the LTBP-3 polypeptide may bind a specific TGF-β isoform, another member of the TGF-β superfamily (e.g., a bone morphogenetic protein, inhibin, activin, or Mullerian inhibiting factor), or a growth factor unrelated to TGF-β. Anti-peptide antibodies to the murine LTBP-3 polypeptide have been generated and osteoblast cell lines that express the molecule at relatively high levels have been identified. Studies with these reagents suggest that LTBP-3 assembles intracellularly into large latent complexes with a growth factor that is being characterized by immunological methods.

The presence of dibasic amino acids in the LTBP-3 sequence suggests that it may undergo cell- and tissue-specific proteolysis. TGF-β regulates extracellular matrix production by suppressing matrix degradation (through a decrease in the expression of proteases such as collagenase, plasminogen activator, and stromelysin plus an increase in the expression of proteiaase inhibitors such as plasminogen activator inhibitor-1 and tissue inhibitor of metalloproteinase-1) and by stimulating matrix macromolecule synthesis (for recent review, see Lyons and Moses, 1990; Massague, 1990; Laiho and Keski-Oja, 1992; Miyazono et al., 1992). Conversely, production of extracellular matrix has been shown to down regulate TGF-β gene expression (Streuli et al., 1993). TGF-β may therefore regulate extracellular matrix production through a sophisticated feedback loop that influences the expression of a relatively large number of genes. LTBP-1 and LTBP-2 may contribute to this regulation by facilitating the assembly and secretion of large latent growth factor complexes and then targeting the complex to specific connective tissues (Taipale et al., 1994).

If LTBP-3 is like LTBP-1, it has the potential to function as a secreted, extracellular structural protein. As demonstrated here, domain #1 of LTBP-3 appears to be a unique sequence that likely has a globular conformation. Domain #1 also is highly basic and may facilitate LTBP-3 binding to acidic molecules (e.g., acidic proteoglycans) within the extracellular space. Sequences rich in basic amino acids have also been shown to function as endoproteolytic processing signals for several peptide hormones (Barr, 1991; Steiner et al., 1992). It is possible, therefore, that the $NH_2$-terminus of LTPP-3 is proteolytically processed in a tissue-specific manner.

Domains #2 and #4 consist of consecutive cysteine-rich repeats, the majority of which are of the EGF-CB type. Besides binding calcium (Corson et al., 1993), these repeats may provide LTBP-3 with regions conformation capable of interacting with other matrix macromolecules (Engel, 1989). Domain #3 is proline rich and may be capable of bending (or functioning like a hinge) in three-dimensional space (MacArthur and Thornton, 1991). (In this regard, domain #2 is of interest because it has a similar stretch of 135 amino acids that is both prolie- and glycine-rich. Since glycine-rich sequences are also thought to be capable of bending or functioning like a hinge in three-dimensional space, this amino acid sequence may interrupt the extended conformation of domain #2, thereby providing it with a certain degree of flexibility in three-dimensional space.)

Domain #5 also appears to be a unique sequence having a globular conformation. The absence of a known cell attachment motif may indicate that, in contrast to LTBP-1, the LTBP-3 molecule may have a more limited role in the extracellular matrix (i.e., that of a structural protein) in addition to its ability to target latent TGF-β complexes to specific connective tissues.

MC3T3-E1 pre-osteoblasts co-express LTBP-3 and TGF-β1 and these proteins form a complex in the culture medium. These results are particularly interesting because bone represents one of the largest known repositories of latent TGF-β

(200 μg/kg bone; Seyedin et al., 1986 and 1987), and because this growth factor plays a critical role in the determination of bone structure and function. For example, TGF-β is thought to (i) provide a powerful stimulus to bone formation in developing tissues, (ii) function as a possible "coupling factor" during bone remodeling (a process that coordinates bone resorption and formation), and (iii) exert a powerful bone inductive stimulus following fracture. Activation of the latent complex may be an important step governing TGF-β effects, and LTBP may modulate the activation process (e.g., it may "protect" small latent complexes from proteolytic attack).

Expression of large latent TGF-β complexes bearing LTBP may be physiologically relevant to, i.e., may be part of the mechanism of, the pre-osteoblast osteoblast differentiation cascade. This is based on the evidence that MC3T3-E1 cells express large latent TGF-β1 complexes bearing LTBP-2 precisely at the time of transition from the pre-osteoblast to osteoblast phenotype (~day 14 in culture, or, at the onset of alkaline phosphatase expression; see Quarles et al., 1992). The organ culture model, for example, likely is comprised of differentiated osteoblasts but few bond progenitors, making it a difficult model best in which to study the differentiation cascade (Dallas et al., 1984). It is also well known that MG63, ROS17/2.8 and UMR 106 cells are rapidly dividing and they express the osteoblast phenotype. Thus, these osteoblast-like cell lines do not show the uncoupling of cell proliferation and cell differentiation that characterizes the normal (physiologically relevant) pre-osteoblast—osteoblast transition (Gerstenfeld et al., 1984; Stein and Lian, 1993). Therefore, the production of small versus large latent TGF-β complexes may be associated with specific stages in the maturation of bone cells.

LTBP-3 may bind calcium, since EGF-CB repeats have been shown to mediate high affinity calcium binding in LTBP-1 and other proteins (Colosetti et al., 1993). Calcium binding, in turn, may contribute to molecular conformation and the regulation of its interactions with other molecules. The presence of dibasic amino acids suggests that LTBP-3 may also undergo cell- and tissue-specific proteolysis. TGF-β regulates extracellular matrix production by suppressing matrix degradation (through a decrease in the expression of proteases such as collagenase, plasminogen activator, and stromelysin plus an increase in the expression of proteinase inhibitors such as plasminogen activator inhibitor-1 and tissue inhibitor of metalloproteinase-1) and by stimulating matrix macromolecule synthesis (for recent reviews, see Lyons and Moses, 1990; Massague, 1990; Laiho and Keski-Oja, 1992; and Miyanzono et al., 1993). Conversely, production of extracellular matrix has been shown to down regulate TGF-β gene expression (Streuli et al., 1993). TGF-β may therefore regulate extracellular matrix production through a sophisticated feedback loop that influences the expression of a relatively large number of genes. LTBP-1, LTBP-2, and LTBP-3 may contribute to this regulation by facilitating the assembly and secretion of large latent growth factor complexes and then targeting the complex to specific connective tissues (Taipale et al., 1994).

EXAMPLE II

Preparation of LTBP-3 Antibodies

Figure 5:
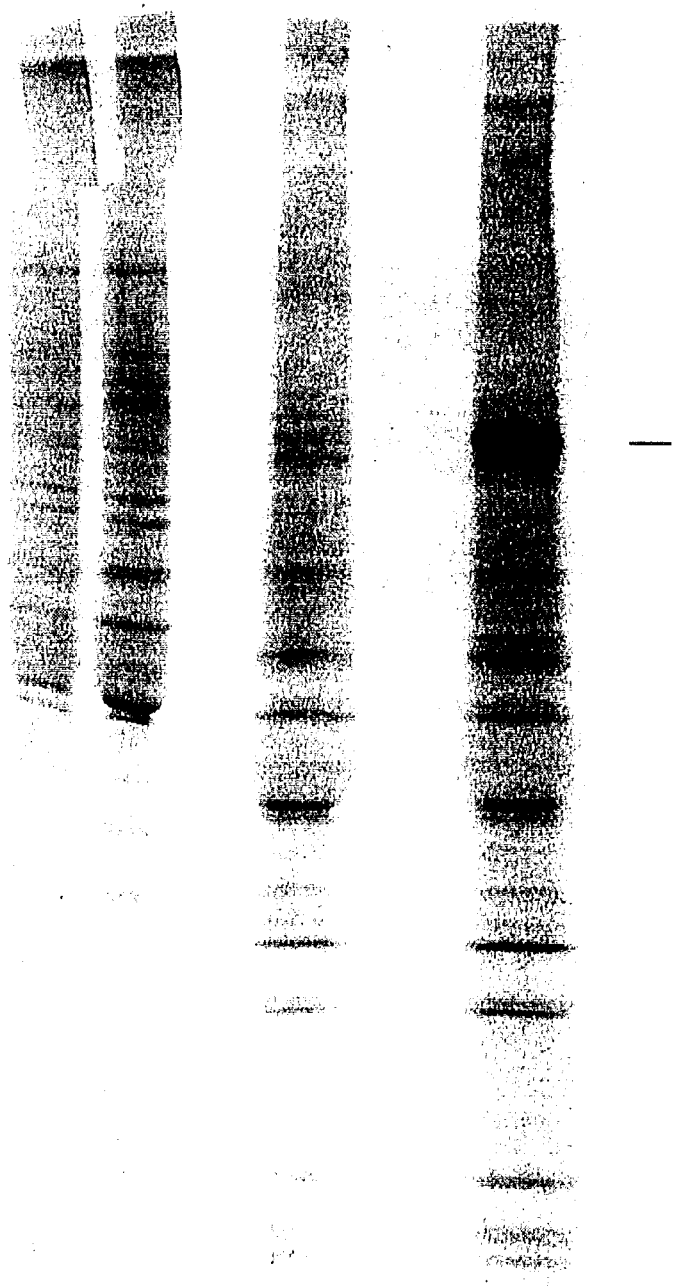
FIG. 5. Antisera #274 specifically binds LTBP-3 epitopes. Transfection of 293T cells with a full length mouse LTBP-3 expression plasmid followed by radiolabeling, preparation of medium sample, immunoprecipitation, and 4–18% gradient SDS-PAGE were performed as described in Example XIV. The figure presents a SDS-PAGE autoradiogram of medium samples following a 2 day exposure to film. Lane assignments are as follows: Lane 1, radiolabeled 293T medium (prior to transfection) immunoprecipitated with preimmune serum; Land 2, radiolabeled 293T medium (prior to transfection) immunoprecipitated with antibody #274; Lane 3, radiolabeled 393T medium (following transfection and preincubation with 10 µg of LTBP-3 synthetic peptide cocktail) immunoprecipitated with antibody #274; and Lane 4, radiolabeled 293T medium (following transfection) immunoprecipitated with antibody #274. As indicated by the bar, the full length LTBP-3 molecule migrated at 180–190 kDa.

An affinity-purified antibody (#274) capable of immuno-precipitating was prepared against the murine LTBP-3 gene product. Full-length murine cDNAs were assembled into the pcDNA3 mammalian expression vector (Invitrogen) and expressed following transient transfection of 293T cells. Nascent polypeptides, radiolabeled by addition of $^{35}S$ Cys to the medium of transfected cells, were immunoprecipitated using affinity-purified antibody #274. As shown in FIG. 5, the new murine polypeptide was estimated to be 180–190 kDa. To ensure the specificity of #274 binding, preincubation with 10 μg of synthetic peptide was shown to block immunoprecipitation of the 180–190 kDa band.

Figure 6:
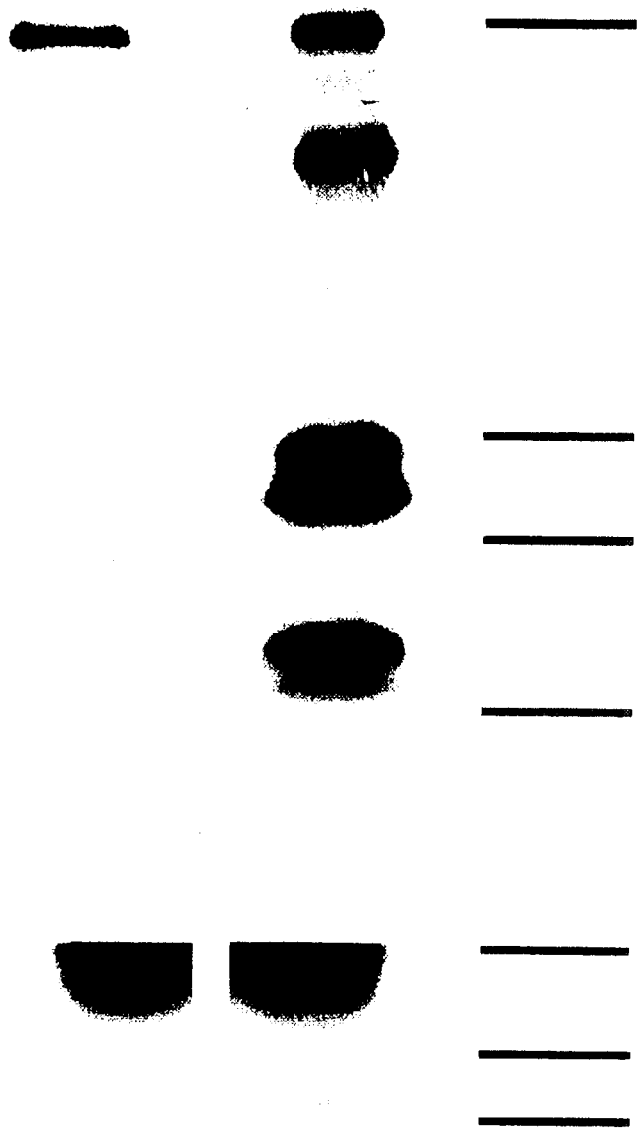
FIG. 6. Co-immunoprecipitation of LTBP-3 and TGR-β1 produced by MC3T3-E1 cells. Aliquots (~$10^6$ incorporated CPM) of radiolabeled media produced by MC3T3-E1 cells after 7 days in culture were immunoprecipitated as described in Example XIV. Bars indicate the position of cold molecular weight standards used to estimate molecular weight (Rainbow mix, Amersham). Immunoprecipitates were separated using 4%–18% gradient SDS-PAGE and reducing conditions. The figure shows a negative control lane 1 consisting of MC3T3-E1 medium immunoprecipitated with anti-LTBP-3 antibody #274. Western blotting was performed using the lower portion of the gradient gel and a commercially available antibody to TGF-β1 (Santa Cruz Biotechnology, Inc.). Antibody staining was detected using commercially available reagents and protocols (ECL Western Blotting Reagent, Amersham). MC3T3-E1 medium was immunoprecipitated with anti-LTBP-2 antibody #274.

Finally, MC3T3-E1 cells were cultured for 7 days under differentiating conditions and m double-labeled with 30 μCi/ml $^{35}S$ cysteine and $^{35}S$ methionine in deficient media. Radiolabeled media was dialyzed into cold PBS with protease inhibitors. Aliquots of the dialyzed medium sample ($10^6$ incorporated CPM) were analyzed by a combined immunoprecipitation/Western analysis protocol. The murine polypeptide was clearly and reproducibly secreted by MC3T3-E1 cells, migrating under reducing conditions as a single band of 180–190 kDa (FIG. 6). Consistent with the results of previous studies (e.g., Miyazono et al., 1988; Dallas et al., 1994; Moren et al., 1994), bands of 70 and 50 kDa corresponding to the TGF-β1 precursor were co-immunoprecipitated with the 180 kDa LTBP-3 protein. Weak bands of 40 and 12 kDa were also identified in experiments in which only immunoprecipitation was performed. The latter were not included in FIG. 6 because they migrated within that portion of the gel included in the Western analysis. Protein bands of 70–12.5 kDa are not variant forms of LTBP-3; FIG. 5 demonstrates that LTBP-3 migrates as a single band of 180–190 kDa following transient transfection of 293T cells, which fail to make TGF-β1. By immunoprecipitation, a unique band consistent with monomeric mature TGF-β1 was found in the LTBP-2 immunoprecipitate. Antibody #274 is incapable of binding TGF-β1 as determined by radioimmunoassay using commercially available reagents (R&D Systems) and the manufacturer's suggested protocols. These results have been reproduced in 6 independent experiments which utilized 3 separate lots of MC3T3-E1 medium. Thus the new murine LTBP-3 polypeptide binds TGF-β in vitro.

In co-transfection studies of 293T Cells using pLTBP-3fl and pTGF-β1, immunoprecipitation of LTBP-3 and TGF-β1 was demonstrated by 293T cells following transient transfection and radiolabeling. Aliquots (~$10^6$ incorporated CPM) of radiolabeled media were immunoprecipitated and separated using 4%–18% gradient SDS-PAGE and either reducing or nonreducing conditions as described (Yin et al., 1995).

Co-transfection of 293T cells with pLTBP-3fl and pTGF-β1 was followed by immunoprecipitation of LTBP-β1 produced by 293T cells following transient transfection and radiolabeling. Aliquots (~$10^6$ incoporagted CPM) of radiolabeled media were immunoprecipitated and separated using 4%–18% gradient SDS-PAGE and either reducing or nonreducing conditions as described (Yin et al., 1995). Cold standards were used to estimate molecular weights (200, 97.4, 69, 46,30, 21.5 and 14.3 kDa; Rainbow mix, Amersham). The immunoprecipitation was followed by: 1,293T cell medium proteins immunoprecipitated with 274 antibody (separated under reducing conditions) after co-transfection with pLTBP-3fl and pTGF-β1; 2, 293T cell medium proteins immunoprecipitated with 274 antibody (separated under nonreducing conditions) after co-transfection with pLTBP-3fl and pTGF-β1; 3, untransfected 293T cell medium proteins immunoprecipitated with 274 antibody (separated under reducing conditions); 4,293T cell medium proteins immunoprecipitated with 274 antibody (separated under reducing conditions) after transfection with pLTBP-3fl; 5,293T cell medium proteins immunoprecipitated with 40091 antibody (separated under reducing conditions) after transfection with pTGF-β1; 6,293T cell medium proteins immunoprecipitated with 40091 antibody (separated under nonreducing conditions) after transfection with pTGF-β1; and Lane 7, 293T cell medium proteins immunoprecipitated with 40091 antibody (separated under reducing conditions) after co-transfection with pLTBP-3fl and pTGF-β1. The signal was weakest in lanes in which proteins ere immunoprecipitated using the 40091 antibody, reflecting the weaker affinity of the 40091 antiserum.

EXAMPLE III

Isolation of a Gene Encoding Murine LTBP-2

In addition to determining the DNA and corresponding polypeptide sequence of the murine LTBP-3 gene, the murine LTBP-2 gene was also cloned and sequenced.

1. Cloning and DNA sequencing of LTBP-2

Figure 7:
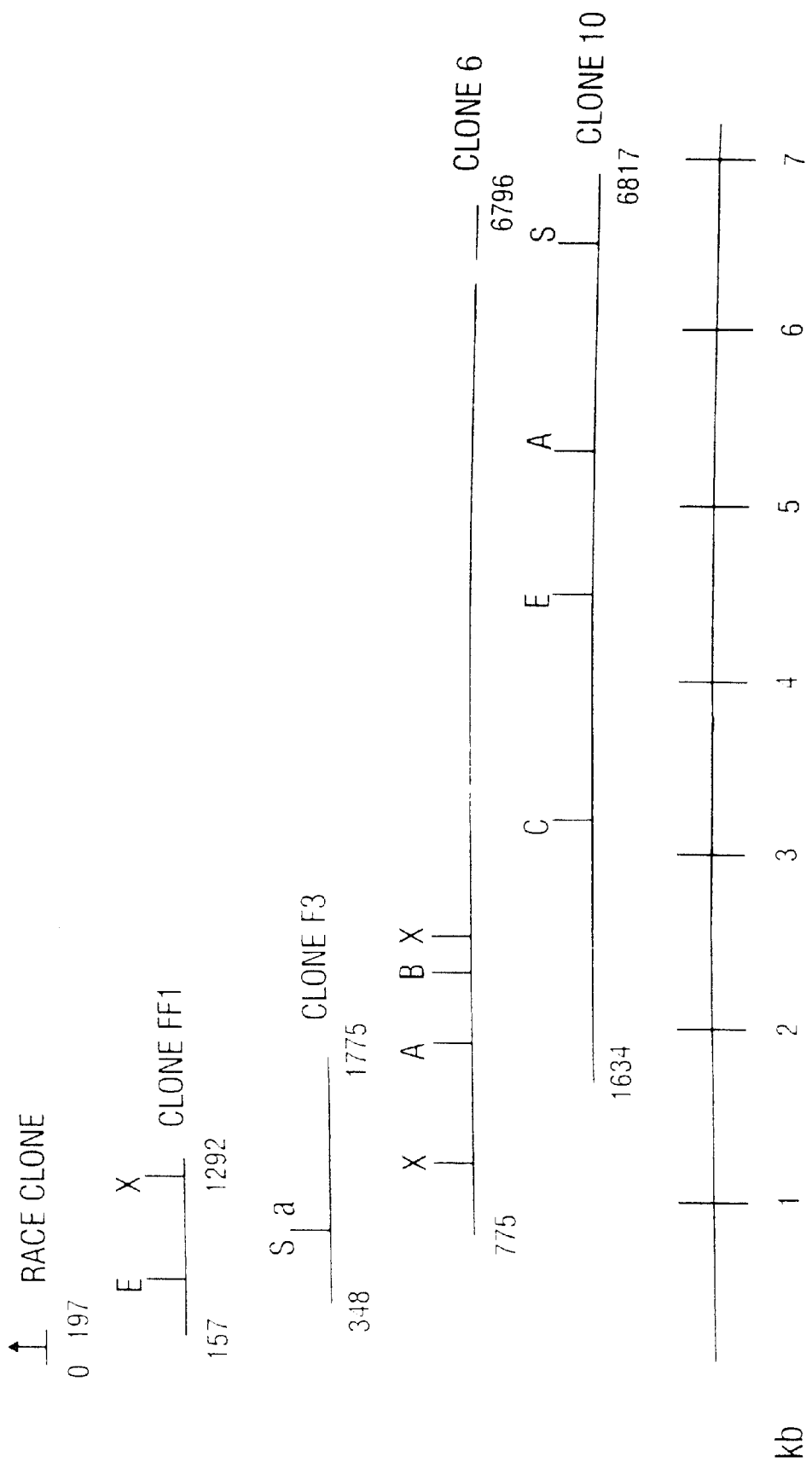
FIG. 7. Mouse ltbp-2 cDNA Clones. The schematic figure presents overlapping muse cDNA clones representing the mouse ltbp-2 coding sequence. A partial representation of the restriction sites is shown. A, AvrII; N, NaeI; Sa, ScaII; X, XhoI; B, BamHI; C, ClaI; and E, EcoRI.

To identify new murine LTBP family members, independently designed degenerate oligonucleotide primers were synthesized based on a structural homology shared by human LTBP-1 and mouse LTBP-3 coding sequences: forward primer, 5'-AAACGTCACACGTGAIAC GTGAACGTTGCTTGCTGG-3' (SEQ ID NO:12); reverse primer, 5'-TTACGTCCACGTACACGTCTAGCAAG CAAGCA-3' (SEQ ID NO:13), and then used PCR™ to amplify single-stranded mouse embryo cDNA prepared from normal CD-1 mouse embryo mRNA. A band of approximately 400 basepairs (bp) was isolated and purified by agarose gel electrophoresis, the DNA was ligated into the TA cloning vector (InVitrogen), and the ligation mixture was used to transform competent bacteria. Plasmid DNA (from 28 colony forming units) was prepared and evaluated by DNA sequence analysis. As determined by sequence identity comparison, 16/28 plasmid DNAs coded for mouse LTBP-1, 11/28 coded for mouse LTBP-3, and 1/28 coded for an apparently unique sequence. The insert DNA from the unique plasmid was then used as a probe to screen a cDNA library prepared from 3T3 cells (Stratagene, Inc.). A walking strategy eventually yielded the overlapping cDNA clones shown in FIG. 7. Analysis of these clones identified an open reading frame of 5,430 base pairs. Comparison of sequence identity using the GAP and BESTFIT programs (Genetics Computer Group) revealed 79.7% identity between the mouse open reading frame and human LTBP-2 (Centrella et al., 1991), but ≦47.1% identity between the mouse open reading frame and human LTBP-1 and mouse LTBP-3. The sequence comparison data agreed with chromosomal localization data, which collectively established that the sequence was the mouse homolog of human LTBP-2.

The level of amino acid sequence identity (approximately 40%) among the LTBP-1, -2, and -3 polypeptides is in the range observed for other protein isoforms that contain multiple EGF-like repeats, like the fibrillins (Yin et al. 1995) and the diverse laminin chains (Engel, 1989).

An LTBP-2 methionine codon in a favorable context for translation initiation was provisionally designated the translation start site (see Kozak, 1991). The deduced initiator methionine was followed by a signal sequence of approximately 35 amino acids. Consistent a with the structure and length of the human LTBP-2 signal peptide (Centrella et al., 1991), the 15 residues immediately downstream of the mouse LTBP-2 initiator methionine were largely hydrophilic in nature, whereas amino acids 16–35 represented a typical hydrophobic signal peptide sequence. The small neutral amino acid residues Ser (−3) and Ala (−1) and the large polar residue Gln (+1) appeared to define the signal peptide cleavage site (von Heijne, 1983).

In contrast to LTBP-1 and -3, which appear to be organized into 5 structurally distinct domains downstream of the signal peptide (Yin er al., 1995), the deduced mouse LTBP-2 polypepide consists of ten alternating structural domains that are composed of either proline- and glycine-rich sequences or cysteine-rich repeat motifs. Thus, domain 1 (amino acids 36–160) was composed of 19.4% glycine and proline residues. Domain 2 (amino acids 161–213) consisted of 2 EGF-like repeats. Domain 3 (amino acids 214344) was composed of 22.3% glycine and proline residues. Domain 4 (amino acids 345–413) consisted of 2 cysteine-rich repeats. Domain 5 (amino acids 414–536) was composed of 19.5% glycine and proline residues. Domain 6 (amino acids 537–708) consisted of 3 cysteine-rich repeats; based on structural homologies, the first repeat was a Fib motif (Pereira et al., 1993; a copy of this reference has been included in the Appendix), the second was an epidermal growth factor-calcium binding (EGF-CB) motif (Handford et al., 1990), and the third was a transforming growth factor-β1-binding protein (TGF-bp) motif (Kanzaki et al., 1990). Domain 7 (amino acids 709–831) was composed of 20.3% proline and glycine residues. Domain 8 (amino acids 832–1626) consisted of 15 EGF-like repeats and 2 TGF-bp repeats. Domain 9 (amino acids 1627–1721) was composed of 29.5% glycine and proline residues. Domain 10 (amino acids 1722–1810) consisted of 2 EGF-like repeat motifs.

The conceptual mouse LTBP-2 amino acid sequence consists of 1,810 amino acids, with an estimated pI of 5.02, a predicted molecular mass of 197,917 Da., and eight potential N-linked glycosylation sites. Similar to the mouse LTBP-3 polypeptide, RGD and laminin B2 chain cell adhesion sequences were not identified. Altogether, 26 cysteine-rich repeats were found in the mouse LTBP-2 polypeptide. As described above, 20/26 were characterized by the presence of 6 cysteine residues and therefore were EGF-like. 12/20 showed the general consensus $D/N-I/V-D/N-E/D-C_1$, derived from an analysis of 154 EGF-like repeats in 23 different proteins and from structural analysis of the coagulation factor X EGF-CB repeat, both bound and unbound to calcium ion (Selander-Sunnerhagen et al., 1992). Variations on the consensus have been noted previously (for examples see Yin et al., 1995; Yin et al., 1995), and two of these, were identified in mouse LTBP-2. Two potential variants which have not previously been reported were also identified ($D-A-D-E-C_1$ and $D-H-N-E-C_1$), giving a total of 16 putative EGF-CB repeats. All 16 repeats also contained a proposed recognition sequence ($C_3$-X-D/N-X-X-X-X-Y/F-X-$C_4$) for an Asp/Asn hydroxylase that co-and posttranslationally modifies D/N residues (Stenflo et al., 1987; Gronke et al., 1989). Previous NMR studies of the isolated first EGF-like domain of human factor IX indicate that 3 residues derived from the general consensus and from the recognition sequence are direct ligands for calcium (Handford et al., 1990; 1995; 1991). This has led to a proposed calcium-binding consensus D/N, D/N, D*/N* (where * denotes a_β-hydroxylated residue). A fourth residue in the consensus as originally proposed, F/Y, is now known not to be a direct ligand for calcium (Hughes et al., 1993). The three amino acids that are direct ligands for calcium in factor IX are conserved in each of the 16 putative EGF-CB repeats identified in mouse LTBP-2.

Four of five of the putative domains rich in proline and glycine were also rich in basic amino acid residues (domain 1, 15.5%; domain 3, 13.1%; domain 5, 11%; domain 7, 8.1%; and domain 9, 3.2%). Co-existence of proline and basic amino acids suggests the possibility that LTBP-2 undergoes 'proline-directed' endoproteolytic processing (Devi, 1991). Indeed, both monobasic and dibasic cleavage motifs—e.g., R-R and R-X-X-R, respectively (Barr, 1991)—were identified in all five postulated proline- and glycine-rich structural domains. In several instances, monobasic cleavage motifs occurred near or within potential dibasic cleavage motifs (e.g., Arg 108, Arg 286, Arg 429, and Lys 727). One potential monobasic cleavage motif was identified in each of the 5 proline- and glycine-rich domains. Dibasic cleavage motifs in general were more prevalent near the deduced LTBP-2 amino terminus. Endoproteolytic cleavage of LTBP is of potential interest because it may help explain the smaller than expected size of platelet LTBP-1.

The complete cDNA nucleotide sequence for murine LTBP-2 is shown in SEQ ID NO:1. The deduced amino acid sequence is shown in SEQ ID NO:2.

Figure 8C:
FIG. 8C. ltbp-2 Gene Expression in the Developing Mouse Skeleton. Shown is a selected darkfield microscopic view of mouse ltbp-2 gene expression in cartilage of day 16.5 p.c. mouse embryos. Photograph was taken from tissue sections following a two week exposure to photographic emulsion. In all darkfield photographs red blood cell and other plasma membranes give a faint white signal that contributes to the background of the study. 1 cm=20 mm.
Figure 8B:
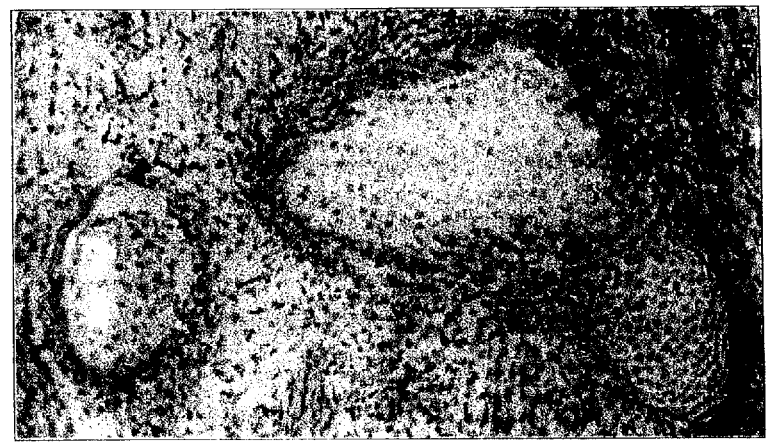
FIG. 8B. ltbp-2 Gene Expression in the Developing Mouse Skeleton. Shown is a selected brightfield microscopic view of mouse ltbp-2 gene expression in cartilage of day 16.5 p.c. mouse embryos. Photograph was taken from tissue sections following a two week exposure to photographic emulsion. 1 cm=20 mm.
Figure 8A:
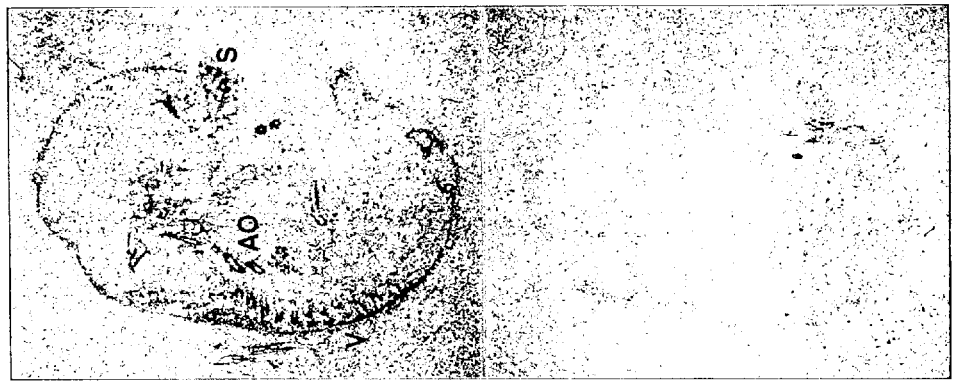
FIG. 8A. ltbp-2 Gene Expression in the Developing Mouse Skeleton. Shown is an overview of the of the ltbp-2 gene during mouse development, as determine by tissue in situ hybridization. The figure presents an autoradiogram made by direct exposure of tissue sections to film after hybridization with radiolabeled probes, but before dipping slides in radiographic emulsion. Day 16.5 p.c. sections contain whole embryos sectioned in the mid-sagittal plane. Identical conditions were maintained throughout autoradiography and photography, making it possible to compare the overall strength of hybridization with antisense (top) and sense (bottom) probes. 1 cm=20 mm.

The inventors have demonstated that ltbp-3 is widely and intensely expressed in both developing maternal tissues (e.g., uterine decidua) and mouse embryo tissues (e.g., mesenchyme, connective tissue, epithelia, and parenchyma). Tissue in situ hybridization was used to compare and contrast the developmental expression of ltbp-2 and ltbp-3. FIG. 8A, FIG. 8B and FIG. 8C present an overview of ltbp-2 expression in a mid-sagittal section of a mouse embryo at day 16.5 p.c. of development, when expression is strongest. The section was hybridized with a $^{35}$S-labeled single stranded antisense riboprobe synthesized from a 580 base pair cDNA coding for the mouse LTBP-2 3' untranslated region. The probe showed <30% sequence identity with the 3' untranslated sequences of human ltbp-1 and ltbp-2, which is too low to give spurious hybridization signals under our conditions. A $^{35}$S-labeled single stranded normal sense riboprobe from the same cDNA construct was used as a negative control. ltbp-2 expression above background was observed in the snout, base of the skull, tail, paw, lung, vertebrae, and large vessels of mouse embryos. Microscopy of day 16.5 p.c. embryo tissue sections, taken from the same slide used to prepare whole mount sections shown in FIG. 8A, demonstrated that the pattern of hybridization was due to significant ltbp-2 gene expression by perichondrial and vascular wall cells. Positive signals were detected, for example, in perichondrial cells of cartilage aggregates located in the vertebral column (v), forelimb and tail, and at the base of the skull (FIG. 8B). Indeed, the perichondrium (pc) of all cartilage aggregates observed in these mouse embryo tissue sections was positively hybridized. ltbp-2 was also expressed by vascular wall cells of the aorta (ao), and in blood vessels within lung parenchyma and within the connective tissue supporting hair follicle structures associated with the snout (s). In contrast, ltbp-2 was expressed at insignificant levels (i.e., below the experimental background) in the generalized mesenchyme/connective tissue, brain, peripheral nerve, tooth rudiment, lung epithelium, cardiac and skeletal muscle, gut epithelium, liver parenchyma, pancreas epithelium and islets of Langerhans, brown fat cells, and kidney parenchyma. These in situ hybridization results, which were reproduced using independent tissue sections, demonstrate for the first time that ltbp-2 expression in developing mouse tissues is more restricted than that of ltbp-3.

3. Chromosomal Localization of Mouse ltbp-2 Gene

The murine ltbp-2 gene was assigned to a mouse chromosome by PCR™ analysis of genomic DNA from a mapping panel consisting of 19 mouse x Chinese hamster and 1 mouse x rat somatic cell hybrid lines as described (Li et al., 1995). A PCR™ product of the expected size (600 bp) was obtained from hybrid cells that had retained mouse chromosome 12. All other mouse chromosomes (except chromosome 12) were excluded by at least four discordant hybrids. Fluorescent in situ hybridization using murine ltbp-2 genomic and cDNA probes generates identical results that localized the ltbp-2 gene to mouse chromosome 12, band D. 14/20 metaphase spreads analyzed exhibited a fluorescent signal on both chromatics of chromosome 12 at the band D site, and 10/12 had signals on both chromosome 12 homologs. No specific signals were seen on other chromosomes. This region in the mouse is a conserved syntenic region with human chromosome 14, band 14q24, the site of the human LTBP-2 genetic locus (Moren et al., 1994), thereby providing strong support for the notion that the murine ltbp-2 gene is the true homolog of human LTBP-2.

EXAMPLE IV

Expression of Recombinant LTBP Protein

The Pichia Expression Kit (Invitrogen, Inc.) may be used to prepare recombinant LTBP protein. This kit, based on the methylotrophic yeast, *Pichia pastoris*, allows high-level expression of recombinant protein in an easy-to-use relatively inexpensive system. In the absence of the preferred carbon source, glucose, *P. pastoris* utilizes methanol as a carbon source. The AOX1 promoter controls the gene that codes for the expression of the enzyme alcohol oxidase, which catalyzes the first step in the metabolism of methanol. This promoter, which is induced by methanol, has been characterized and incorporated into a series of Pichia expression vectors. This feature of Pichia has been exploited to express high levels of recombinant proteins often in the range of grams per liter. Because it is eukaryotic, *P. pastoris* utilizes posttranslational modification pathways that are similar to those used by mammalian cells. This implies that the recombinant LTBP-2 or LTBP-3 protein will be glydosylated and will contain disulfide bonds.

For preparation of a recombinant LTBP-2 or LTBP-3 protein, the native LTBP-2 or LTBP-3 cDNA is modified by the addition of a commercially available epitope tag (the HA epitope, Pharmacia, LKB Biotechnology, Inc.). Such fragments may be readily prepared by, for example, directly synthesizing the fragment by chemical means, by application of nucleic acid reproduction technology, such as the PCR™ technology of U.S. Pat. No. 4,683,202 (herein incorporated by reference) or by introducing selected sequences into recombinant vectors for recombinant production. (PCR™ is a registered trademark of Hoffmann-LaRoche, Inc.). This is followed by cloning into the Pichia expression vector. The resulting plasmid is characterized by DNA sequence analysis, linearized by digestion with NotI, and spheroplasts will be prepared and transformed with the linearized construct according to the manufacturer's recommendations.

Transformation facilitates a recombination event in vivo between the 5' and 3' AOX1 sequences in the Pichia vector and those in the Pichia genome. The result is the replacement of AOX1 with the gene of interest.

Transformants are then plated on histidine-deficient media, which will select for successfully transformed cells. Transformants are further selected against slow growth on growth media containing methanol. Positive transformants are grown for 2 days in liquid culture and then for 2–6 days in broth that uses methanol as the sole carbon source. Protein expression is evaluated by sodium dodecyl sulfate-polyacrylamide gel electrophoresis (SDS-PAGE) and Western hybridization using a commercially available polyclonal antisera to the HA epitope (Pharmacia). Recombinant LTBP-2 or LTBP-3 protein may be purified according to the manufacturer's recommendations, dialyzed against double distilled, deionized water and lyophilized in 10 mg aliquots.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of-the invention as defined by the appended claims.

REFERENCES

The following literature citations as well as those cited above are incorporated in pertinent part by reference herein for the reasons cited in the above text.

U.S. Pat. No. 4,554,101
U.S. Pat. No. 4,683,202
U.S. Pat. No. 4,603,102
U.S. Pat. No. 4,877,864
U.S. Pat. No. 5,108,753
U.S. Pat. No. 5,125,978
Abou-Samra et al., "Expression cloning of a common receptor for parathyroid hormone and parathyroid hormone-related peptide from rat osteoblast-like cells: a single receptor stimulates intracellular accumulation of both cAMP and inositol triphosphates and increases intracellular free Calcium," *Proc. Natl. Acad. Sci. U.S.A.*, 89:2732–2736, 1992.
Alper, "Boning up: newly isolated proteins heal bad breaks," *Science*, 263:324–325, 1994.
Amarnani et al., *J. Bone Min. Res.*, 8:157–164, 1993.
Antibodies: A Laboratory Manual, Cold
Antonelli-Olridge et al., *Proc. Natl. Acad. Sci. USA*, 86:4544–4548, 1989.
Assoian et al., "Transforming growth factor-beta in human platelets," *J. Biol. Chem.*, 258:7155–7160, 1983.
Barr, *Cell*, 66:1–3, 1991.
Beck et al., "TGF-beta 1 induces bone closure of skull defects," *J. Bone Miner. Res.*, 11:1257–65, 1991.
Beck et al., "TGF-β1 induces bone closure of skull defects: temporal dynamics of bone formation in defects exposed to rh TGF-β1," *J. Bone Min. Res.*, 8:753–761, 1993.
Benezra et al., *Blood*, 81:3324–3331, 1993.
Bittner et al., *Methods in Enzymol.*, 153:516–544, 1987.
Boden et al., "Estrogen receptor mRNA expression in callus during fracture healing in the rat," *Calcif. Tissue Int.*, 45:34–325, 1989.
Bonadio et al., *J. Biol. Chem.*, 260:1734–1742, 1985.
Bondaio and Goldstein, "Our understanding of inherited skeletal fragility and what this has taught us about bone structure and function, In: *Molecular and Cellular Biology of Bone*," Noda, M., ed., Academic Press, Inc., San Diego, Calif. pp. 169–189, 1993.
Bonewald et al., "Latent forms of transforming growth factor-beta (TGF-beta) derived from bone cultures: identification of a naturally occurring 100-kDa complex with similarity to recombinant latent TGF beta," *Mol. Endocrinol.*, 5:741–751, 1991.
Byers and Steiner, "Osteogenesis imperfecta," *Annu. Rev. Med.*, 43:269–289, 1992.
Carrington et al., "Accumulation, localization, and compartmentation of transforming growth factor b during endochondral bone development," *J. Cell Biol.*, 107:1969–1975, 1988.
Centrella et al., "Skeletal tissue and transforming growth factor-b," *FASEB J.*, 22:23066–3073, 1988.
Centrella et al., "Transforming growth factor-beta and remodeling of bone," *J. Bone Jt. Surg.*, 73-A:1418428, 1991.
Cheifetz et al., *Cell*, 48:409–415, 1987.
Chen et al., "Bone morphogenetic protein-2b stimulation of growth and osteogenic phenotypes in rat osteoblast-like cells: comparison with TGF-beta 1," *J. Bone Miner. Res.*, 6:1387–93, 1991.
Chen et al., "Structure, chromosomal localization, and expression pattern of the murine Magp gene," *J. Biol. Chem.*, 268:27381–27389, 1993.
Colberre-Garapin et al., *J. Mol. Biol.*, 150:1, 1981.
Colsoetti et al., *FEBS Letters*, 320:140–144, 1993.
Corson et al., 1993.
Courey and Tjian, *Cell*, 55:887–898, 1988.
Cunningham et al., "Osteogenic and recombinant bone morphogenetic protein 2B are chemotactic for human monocytes and stimulate transforming growth factor b1 mRNA expression," *Proc. Natl. Acad. Sci. U.S.A.*, 89:11740–11744, 1992.
Dallas et al., *J. Biol. Chem.*, 269:6815–6822, 1994.
Davis, *New Biologist*, 2:410419, 1990.
Devi, "Consensus sequence for processing of peptide precursors at monobasic sites," *FEBS Lett*, 280:189–194, 1991.
Engel, *FEBS Letters*, 251:1–7, 1989.
Falcone et al., *J. Biol. Chem.*, 268:11951–11958, 1993.
Flaumenhaft et al., *J. Cell Biol.*, 120:995–1002, 1993.
Frolik et al., "Purification and initial characterization of a type beta transforming growth factor from human placenta," *Proc. Natl. Acad. Sci. U.S.A.*, 80:3676–3680, 1983.
Gefter et al., *Somatic Cell Genet*, 3:231–236, 1977.
Gentry et al., "Type 1 transforming growth factor beta: amplified expression and secretion of mature and precursor polypeptides in Chinese hamster ovary cells," *Molec. Cell Biol.*, 7:3418–3427, 1987.
Gentry et al., "Molecular events in the processing of recombinant type 1 pre-pro-transforming growth factor beta to the mature polypeptide," *Molec. Cell Biol.*, 8:4162–4168, 1988.
Gerstenfeld et al., *Dev. Biol.*, 122:49–60, 1987.
Goding, In: Monoclonal Antibodies: Principles and Practice, 2d ed., Orlando, Fla., Academic Press, pp. 60–61, 65–66, 71–74, 1986.
Gronke et al., *Proc. Natl. Acad. Sci. USA*, 86:3609–3613, 1989.
Handford et al., "Key residues involved in calcium-binding motifs in EGF-like domains," *Nature*, 351:164–167, 1991.
Handford et al., *EMBO J.*, 9:475480, 1990.
Handford et al., "The calcium binding properties and molecular organization of epidermal growth factor-like domains in human fibrillin-1," *J. Biol. Chem.*, 270:6751–6756, 1995.

Harlow, E. and Lane, D. "Antibodies: A Laboratory Manual," Cold Spring Harbor Laboratory, Cold Spring Harbor, N.Y., 1988.

Heine et al., *J. Cell Biol.*, 105:2861–2876, 1987.

Hess et al., *J. Adv. Enzyme Reg.*, 7:149, 1968.

Hitzeman et al., *J. Biol. Chem.*, 255:2073, 1980.

Holland et al., *Biochemistry*, 17:4900, 1978.

Horowitz et al., "Functional and molecular changes in colony stimulating factor secretion by osteoblasts," *Connective Tissue Res.*, 20:159–168, 1989.

Huggins et al., "Experiments on the theory of osteogenesis. The influence of local calcium deposits on ossification; the osteogenic stimulus of epithelium," *Arch. Surg.*, 32:915, 1936.

Hughes et al., "Tyrosine 69 of the first epidermal growth factor-like domain of human factor IX is essential for clotting activity," *J. Biol. Chem.*, 268:17727–17733, 1993.

Inouye et al., *Nucleic Acids Res.*, 13:3101–3109, 1985.

Izumi et al., "Transforming growth factor b1 stimulates type II collagen expression in cultured periosteal-derived cells," *J. Bone Min. Res.*, 7:115–11, 1992.

Jingushi et al., "Acidic fibroblast growth factor injection stimulates cartilage enlargement and inhibits cartilage gene expression in rat fracture healing," *J. Orthop. Res.*, 8:364–371, 1990.

Jingushi et al., "Genetic expression of extracellular matrix proteins correlates with histologic changes during fracture repair," *J. Bone Min. Res.*, 7:1045–1055, 1992.

Jones, *Genetics*, 85:12, 1977.

Joyce et al., "Transforming growth factor-β and the initiation of chondrogenesis and osteogenesis in the rat femur," *J. Cell Biol.*, 110:195–2007, 1990.

Kanzaki et al., *Cell*, 61:1051–1061, 1990.

Kingsley, D. M., "The TGF-β superfamily:new members, new receptors, and new genetic tests of function in different organisms," *Genes and Development* 8:133–146, 1994.

Kingsman et al., *Gene*, 7:141, 1979.

Kozak, "Structural features in eukaryotic mRNAs that modulate the initiation of translation," *J. Biol. Chem.*, 266:19867–19870, 1991.

Kyte and Doolittle, *J. Mol. Biol.*, 157:105–132, 1982.

Laiho and Keski-Oja, 1992.

Lee et al., "Identification of the molecular defect in a family with spondyloepiphyseal dysplasia," *Science*, 244:978–980, 1989.

Lee et al., "Parathyroid hormone induces sequential c-fos expression in bone cells in vivo: in situ localization of its receptor and c-fos mRNAs," *Endocrinology*, 1994.

Lehnert and Akhurst, *Development*, 104:263–273, 1988.

Li et al., "Mapping of human and murine genes for latent TGF-β binding protein-2 (LTBP-2)," *Mammalian Genome*, 6:42–45, 1995.

Lopez-Casillas et al., *J. Cell Biol.*, 124:557–568, 1994.

Lowy et al., *Cell*, 22:817, 1980.

Lyons and Moses, *Eur. J. Biochem.*, 187:467–473, 1990.

Lyons et al., *J. Cell Biol.*, 106:1549–1665, 1988.

Lyons et al., *Proc. Natl. Acad. Sci. U.S.A.*, 86:4554–4558, 1989.

MacArthur and Thornton, *J. Mol. Biol.*, 218:397–412, 1991.

Majmudar et al., "Bone cell culture in a three-dimensional polymer bead stabilizes the differentiated phenotype and provides evidence that osteoblastic cells synthesize type III collagen and fibronectin," *J. Bone and Min. Res.*, 6:869–881, 1991.

Massague, *Annu. Rev. Cell Biol.*, 6:597–641, 1990.

McDonald, N. Q., and Hendrickson, W. A., "A structural superfamily of growth factors containing a cystine knot motif," *Cell.*, 73:421424, 1993.

Millan et al., *Development*, 111:131–144, 1991.

Miyazono and Heldin, *Nature*, 338:158–160, 1989.

Miyazono et al., *EMBO J.*, 10:1091–1101, 1991.

Miyazono et al., *J. Biol. Chem.*, 267:5668–5675, 1992.

Miyazono et al., *J. Biol. Chem.*, 263:6407–6415, 1988.

Miyazono et al., *Adv. Immunol.*, 55:181–220, 1994.

Miyazono et al., "Latent forms of TGF-beta: structure and biology," *Ann. N.Y. Acad. Sci.*, 593:51–58, 1990.

Moren et al., 1994.

Moses et al., "TGF-β stimulation and inhibition of cell proliferation: new mechanistic insights," *Cell* 63:245–247, 1990.

Mulligan et al., *Proc. Natl. Acad. Sci. USA*, 78:2072, 1981.

Ogawa et al., *J. Biol. Chem.*, 267:2325–2328, 1992.

O'Hare et al., *Proc. Natl. Acad. Sci. USA*, 78:1527, 1981.

Olofsson et al., *J. Biol. Chem.*, 267:19482–19488, 1992.

Oreffo et al., "Activation of the bone-derived latent TGF beta complex by isolated osteoclasts," *Biochem. Biophys. Res. Commun.*, 158:817–823, 1989.

Pelton et al., *Development*, 106:759–767, 1989.

Pelton et al., *Dev. Biol.*, 141:456–460, 1990a.

Pelton et al., *Development*, 110:609–620, 1990b.

Pereira et al., *Human Mol. Genet.*, 2:961–968, 1993.

Pfeilschifter et al., "Characterization of the latent transforming growth factorβ complex in bone," *J. Bone Min. Res.*, 5:49–57, 1990.

Pilatte et al., "Lysosomal and cytosolic sialidases in rabbit alveolar macrophages: demonstration of increased lysosomal activity after in vivo activation with bacillus Calmette-Guerin," *Biochim Biophys Acta*, 923:150–155, 1987.

Pircher et al., *Biochem. Biophys. Res. Commun.*, 136:30–37, 1986.

Pircher et al., *Cancer Res.*, 44:5538–5543, 1984.

Prockop, "Mutations that alter the primary structure of type I collagen. The perils of a system for generating large structures by the principle of nucleated growth," *J. Biol. Chem.*, 265:15349–15352, 1990.

Quarles et al., *J. Bone Min. Res.*, 7:683–692, 1992.

Roberts et al., "Purification and properties of a type beta transforming growth factor from bovine kidney," *Biochemistry*, 22:5692–5698, 1983.

Roberts et al., "Type beta transforming growth factor: a bifunctional regulator of cellular growth," *Proc. Natl. Acad. Sci. U.S.A.*, 82:119–123, 1985.

Roberts and Sporn, "The transforming growth factor-betas. In: Handbook of Experimental to Pharmacology: Peptide Growth Factors and Their Receptors," M. B. Sporn and A. B. Roberts, Eds., Springer-Verlag, Heidelberg, 95(Part 1):419–472, 1990.

Rosen et al., "Purification and molecular cloning of a novel group of BMPs and localization of BMP mRNA in developing bone," *Connect. Tissue Res.*, 20:313–319, 1989.

Sambrook et al., *Molecular Cloning, A Laboratory Manual.* Cold Spring Harbor Laboratory Press, pp. 18.60, 1989.

Sampath and Reddi, "Dissociative extraction and reconstitution of extracellular matrix components involved in local bone differentiation," *Proc. Natl. Acad. Sci. U.S.A.*, 78:7599–7603, 1981.

Sampath et al., "In vitro transformation of mesenchymal cells derived from embryonic muscle into cartilage in response to extracellular matrix components of bone," *Proc. Natl. Acad. Sci. U.S.A.* 81:3419–3423, 1984.

Santerre et al., *Gene*, 30:147, 1984.

Sato et al., *J. Cell Biol.*, 123:1249–1254, 1993.

Seitz et al., "Effect of transforming growth factor b on parathyroid hormone receptor binding and cAMP formation in rat osteosarcoma cells," *J. Bone Min. Res.*, 7:541–546, 1992.

Selander-Sunnerhagen et al., *J. Biol. Chem.*, 267:19642–19649, 1992.

Seyedin et al., *J. Biol. Chem.*, 261:5693–5695, 1986.

Seyedin et al., *J. Biol. Chem.*, 262:1946–1949, 1987.

Silver et al., "Microelectrode studies on the acid environment beneath adherent macrophages and osteoclasts," *Expt. Cell Res.*, 175:266–276, 1988.

Sporn et al., "Transforming growth factor-β: biological function and chemical structure," *Science*, 233:532–534, 1986.

Stenflo et al., 1987.

Stein and Lian, *Enddocr. Rev.*, 14:424–442, 1993.

Steiner et al., *J. Biol. Chem.*, 267:23435–23438, 1992.

Stenflo et al., *Proc. Natl. Acad. Sci. USA*, 84:368–372, 1987.

Stenman et al., *Cytogenet. Cell Genet.*, 66:117–119, 1994.

Stinchcomb et al., *Nature*, 282:39, 1979.

Streuli et al., *J. Cell Biol.*, 120:253–260, 1993.

Szybalska et al., *Proc. Natl. Acad. Sci. USA*, 48:2026, 1962.

Taipale et al., *J. Cell Biol.*, 124:171–181, 1994.

Taipale et al., "Human mast cell chymase and leukocyte elastase release latent transforming growth factor-beta 1 from the extracellular matrix of cultured human epithelial and endothelial cells," *J. Biol. Chem.*, 270:4689–4696, 1995.

Taipale et al., "Human mast cell chymase and leukocyte elastase release latent transforming growth factor-beta 1 from the extracellular matrix of cultured human epithelial and endothelial cells," *J. Biol. Chem.*, 270:4689–4696, 1995.

Taketazu et al., *Lab. Invest.*, 70:620–630, 1994.

Toriumi et al., "Mandibular reconstruction with a recombinant bone-inducing factor, *Arch. Otolaryngol. Head Neck Surg.*, 117:1101–1112, 1991.

Tschemper et al., *Gene*, 10:157, 1980.

Tsuji et al., *Proc. Natl. Acad. Sci. U.S.A.*, 87:8835–8839, 1990.

Twardzik et al., *Ann. N.Y. Acad. Sci.*, 593:276–284, 1990.

Urist, "Bone formation by auto induction," *Science*, 150:893–899, 1965.

Urist et al., "Bone cell differentiation and growth factors," *Science*, 220:680–686, 1983.

Van Vlasselaer et al., *J. Cell Biol.*, 124:579–577, 1994.

von Heijne, "Patterns of amino acids near signal-sequence cleavage sites." *FEBS Lett.*, 17–21, 1983.

Wakefield et al., *J. Cell Biol.*, 105:965–975, 1987.

Wakefield et al., *J. Biol. Chem.*, 263:7646–7654, 1988.

Wakefield et al., "Recombinant TGF-β1 is synthesized as a two component latent complex that shares some structural features with the native platelet latent TGF-β1 complex," *Growth Factors*, 1:203–218, 1989.

Wang et al., "Recombinant human bone morphogenetic protein induces bone formation," *Proc. Natl. Acad. Sci. U.S.A.*, 87:2220–2224, 1990.

Wigler et al., *Cell*, 11:223, 1977.

Wigler et al., *Proc. Natl. Acad. Sci. USA*, 77:3567, 1980.

Wozney et al., "Novel regulators of bone formation: molecular clones and activities," *Science*, 242:1528–1534, 1988.

Yasko et al., "The healing of segmental bone defects, induced by recombinant human bone morphogenetic protein (rhBMP-2). A radiographic, histological, and biomechanical study in rats," *J. Bone Joint Surg.*, 5:659–70, 1992.

Yasuda et al., "Rat parathyroid hormonelike peptide: Comparison with the human homologue and expression malignant and normal tissue," *Mol. Endocrinol.*, 3:518–525, 1989.

Yin et al., "Molecular cloning of a novel fibrillin-like cDNA: expression in callus tissue as alternatively spliced transcripts," (40th annual meeting, Orthopaedic Research Society, Feb. 21–24, 1994, New Orleans, La.), *Trans. Orthop. Res. Soc.*, 19:509, 1994.

Zhang et al., *J. Cell Biol.*, 124:855–863, 1994.

What is claimed is:

1. A method for binding a latent transforming growth factor β (TGF-β) protein in a sample, comprising contacting said sample with a purified mammalian LTBP-3 protein or polypeptide under conditions effective to allow binding of said LTBP-3 protein or polypeptide to said latent TGF-β protein; wherein said LTBP-3 protein or polypeptide specifically binds to latent TGF-β1 and exhibits at least 90% identity to the amino acid sequence of SEQ ID NO:4.

2. The method of claim 1, wherein said sample is located within an animal and said LTBP-3 protein or polypeptide is administered to said animal in an amount effective to bind latent TGF-β in said animal.

3. A method of binding latent TGF-β, comprising contacting a composition comprising latent TGF-β with a composition comprising a purified mammalian LTBP-3 protein or polypeptide in an amount effective to bind latent TGF-β; wherein said LTBP-3 protein or polypeptide specifically binds to latent TGF-β1 and exhibits at least 90% identity to the amino acid sequence of SEQ ID NO:4.

4. The method of claim 3, wherein said composition comprising latent TGF-β is located within an animal and said composition comprising said LTBP-3 protein or polypeptide is administered to said animal in an amount effective to bind latent TGF-β in said animal.

5. A method of binding latent TGF-β, comprising providing to an animal a composition comprising a purified mammalian LTBP-3 protein or polypeptide in an amount effective to bind latent TGF-β in said animal; wherein said LTBP-3 protein or polypeptide specifically binds to latent TGF-β1 and exhibits at least 90% identity to the amino acid sequence of SEQ ID NO:4.

6. The method of claim 5, wherein LTBP-3 binding to latent TGF-β regulates TGF-β activity in said animal.

7. The method of claim 5, wherein LTBP-3 binding to latent TGF-β modulates the activation of TGF-β in said animal.

8. The method of claim 5, wherein LTBP-3 binding to latent TGF-β modulates the activation of latent complexes that comprise TGF-β, thereby regulating TGF-β activity.

9. The method of claim 5, wherein LTBP-3 binding to latent TGF-β targets TGF-β to the extracellular matrix in said animal.

10. The method of claim 5, wherein LTBP-3 binding to latent TGF-β targets TGF-β to the bone matrix in said animal.

11. The method of claim 5, wherein LTBP-3 binding to latent TGF-β targets TGF-β to connective tissues in said animal.

12. The method of claim 5, wherein LTBP-3 binding to latent TGF-β targets TGF-β to the cell surface of cells in said animal.

13. The method of claim 5, wherein LTBP-3 binding to latent TGF-β protect latent TGF-β from proteolytic attack and activation in said animal.

14. The method of claim 5, wherein LTBP-3 binding to latent TGF-β protects latent TGF-β from proteolytic attack and activation during wound repair or tissue healing in said animal.

15. The method of claim 5, wherein said LTBP-3 protein or polypeptide is a recombinant protein or polypeptide prepared by expressing an LTBP-3-encoding DNA segment in a recombinant host cell and purifying the expressed LTBP-3 protein or polypeptide away from total recombinant host cell components.

16. The method of claim 5, wherein said latent TGF-β is located within a tissue healing, wound repair tissue site or bone progenitor tissue site of said animal and wherein said LTBP-3 protein or polypeptide is provided to said tissue site.

17. The method of claim 16, wherein said latent TGF-β is located within a tissue healing or wound repair tissue site of said animal.

18. The method of claim 16, wherein said latent TGF-β is located within a bone progenitor tissue site of said animal.

19. The method of claim 5, wherein said LTBP-3 protein or polypeptide comprises at least about thirty contiguous amino acids present in SEQ ID NO:4.

20. The method of claim 5, wherein said LTBP-3 protein or polypeptide comprises at least about fifty contiguous amino acids present in SEQ ID NO:4.

21. The method of claim 5, wherein said LTBP-3 protein or polypeptide exhibits between 91% and about 99% identity to the amino acid sequence set forth in SEQ ID NO:4.

22. The method of claim 5, wherein said LTBP-3 protein or polypeptide comprises the amino acid sequence of SEQ ID NO:4.

23. A method of binding latent TGF-β within an extracellular matrix or connective tissue site of an animal, comprising contacting said tissue site with a purified mammalian LTBP-3 protein or polypeptide in an amount effective to bind latent TGF-β in said animal; wherein said LTBP-3 protein or polypeptide specifically binds to latent TGF-β1 and exhibits at least 90% identity to the amino acid sequence of SEQ ID NO:4.

24. A method of binding latent TGF-β within a repair or bone progenitor tissue site of an animal, comprising contacting said tissue site with a purified mammalian LTBP-3 protein or polypeptide in an amount effective to bind latent TGF-β in said animal; wherein said LTBP-3 protein or polypeptide specifically binds to latent TGF-β1 and exhibits at least 90% identity to the amino acid sequence of SEQ ID NO:4.

25. A method of binding latent TGF-β, comprising administering to an animal a composition comprising a purified mammalian LTBP-3 protein or polypeptide in an amount effective to bind latent TGF-β in said animal; wherein said LTBP-3 protein or polypeptide binds latent TGF-β and comprises at least fifteen contiguous amino acids present in SEQ ID NO:4 and exhibits at least 90% identity to the amino acid sequence set forth in SEQ ID NO:4.

26. A method of binding a latent complex of TGF-β that comprises mature TGF-β and latency associated peptide (LAP), said method comprising contacting a composition comprising said latent complex of TGF-β with a composition comprising a purified mammalian LTBP-3 protein or polypeptide in an amount effective to bind to said latent complex of TGF-β; wherein said LTBP-3 protein or polypeptide specifically binds to latent TGF-β1 and exhibits at least 90% identity to the amino acid sequence of SEQ ID NO:4.

27. The method of claim 26, wherein said composition comprising said latent complex of TGF-β is located within an animal and said composition comprising said LTBP-3 protein or polypeptide is administered to said animal in an amount effective to bind to said latent complex of TGF-β in said animal.

28. A method of binding a latent complex of TGF-β that comprises mature TGF-β and latency associated peptide (LAP), said method comprising providing to an animal a composition comprising a purified mammalian LTBP-3 protein or polypeptide in an amount effective to bind to LAP in a latent complex of TGF-β in said animal; wherein said LTBP-3 protein or polypeptide binds to LAP in said latent complex of TGF-β and exhibits at least 90% identity to the amino acid sequence of SEQ ID NO:4.

* * * * *

UNITED STATES PATENT AND TRADEMARK OFFICE
CERTIFICATE OF CORRECTION

PATENT NO. : 6,774,105 B1  Page 1 of 1
DATED : August 10, 2004
INVENTOR(S) : Bonadio et al.

It is certified that error appears in the above-identified patent and that said Letters Patent is hereby corrected as shown below:

Title page,
Item [*] Notice, delete "by 0 days" and insert -- by 29 days -- therefor.

Column 92,
Line 56, delete "protect" and insert -- protects -- therefor.

Signed and Sealed this

Fifteenth Day of February, 2005

JON W. DUDAS
*Director of the United States Patent and Trademark Office*

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
    (A) LENGTH: 5499 base pairs
    (B) TYPE: nucleic acid
    (C) STRANDEDNESS: single
    (D) TOPOLOGY: linear (ii) MOLECULE TYPE: <Unknown>
    (A) DESCRIPTION: /desc = "DNA"

(ix) FEATURE:
    (A) NAME/KEY: CDS
    (B) LOCATION: 1..5499

(xi) SEQUENCE DESCRIPTION: SEQ ID NO: 1:

```
ATG GAG AGC ACC TCC CCG CGA GGT CTC CGG TGC CCA CAG CTC TGC AGC      48
Met Glu Ser Thr Ser Pro Arg Gly Leu Arg Cys Pro Gln Leu Cys Ser
 1               5                  10                  15

CAC TCT GGC GCC ATG AGA GCG CCG ACC ACC GCT CGC TGC TCC GGA TGC      96
His Ser Gly Ala Met Arg Ala Pro Thr Thr Ala Arg Cys Ser Gly Cys
                 20                  25                  30

ATC CAA CGG GTG CGT TGG AGG GGC TTC CTG CCA CTT GTC CTG GCT GTC     144
Ile Gln Arg Val Arg Trp Arg Gly Phe Leu Pro Leu Val Leu Ala Val
             35                  40                  45

TTG ATG GGG ACA AGT CAT GCC CAA CGG GAT TCC ATA GGG AGA TAC GAA     192
Leu Met Gly Thr Ser His Ala Gln Arg Asp Ser Ile Gly Arg Tyr Glu
         50                  55                  60

CCA GCT AGC AGG GAT GCG AAT CGG TTG TGG CAC CCC GTG GGC AGC CAC     240
Pro Ala Ser Arg Asp Ala Asn Arg Leu Trp His Pro Val Gly Ser His
 65                  70                  75                  80

CCC GCA GCG GCT GCA GCC AAG GTG TAC AGT CTG TTC CGA GAG CCT GAC     288
Pro Ala Ala Ala Ala Ala Lys Val Tyr Ser Leu Phe Arg Glu Pro Asp
                 85                  90                  95

GCG CCG GTC CCC GGC TTG TCG CCC TCT GAG TGG AAC CAG CCG GCC CAG     336
Ala Pro Val Pro Gly Leu Ser Pro Ser Glu Trp Asn Gln Pro Ala Gln
            100                 105                 110

GGG AAC CCG GGA TGG CTC GCA GAG GCC GAG GCC AGG AGG CCA CCT CGA     384
Gly Asn Pro Gly Trp Leu Ala Glu Ala Glu Ala Arg Arg Pro Pro Arg
        115                 120                 125

ACC CAG CAG CTG CGT CGA GTC CAG CCA CCT GTC CAG ACT CGG AGA AGC     432
Thr Gln Gln Leu Arg Arg Val Gln Pro Pro Val Gln Thr Arg Arg Ser
130                 135                 140

CAT CCC CGG GGC CAG CAG CAG ATA GCA GCC CGG GCT GCA CCT TCT GTC     480
His Pro Arg Gly Gln Gln Gln Ile Ala Ala Arg Ala Ala Pro Ser Val
145                 150                 155                 160

GCG CGC CTG GAA ACC CCT CAG CGA CCC GCG GCT GCA CGG CGA GGG CGG     528
Ala Arg Leu Glu Thr Pro Gln Arg Pro Ala Ala Ala Arg Arg Gly Arg
                165                 170                 175

CTC ACT GGG AGA AAT GTC TGC GGG GGA CAG TGC TGC CCA GGA TGG ACA     576
Leu Thr Gly Arg Asn Val Cys Gly Gly Gln Cys Cys Pro Gly Trp Thr
            180                 185                 190

ACA TCA AAC AGC ACC AAC CAC TGT ATC AAA CCT GTG TGT CAG CCT CCC     624
Thr Ser Asn Ser Thr Asn His Cys Ile Lys Pro Val Cys Gln Pro Pro
        195                 200                 205

TGT CAG AAC CGA GGC TCC TGC AGC AGG CCC CAG GTC TGC ATC TGC CGT     672
Cys Gln Asn Arg Gly Ser Cys Ser Arg Pro Gln Val Cys Ile Cys Arg
    210                 215                 220

TCT GGC TTC CGT GGG GCG CGC TGT GAG GAG GTC ATC CCT GAG GAG GAA     720
Ser Gly Phe Arg Gly Ala Arg Cys Glu Glu Val Ile Pro Glu Glu Glu
225                 230                 235                 240

TTT GAC CCT CAG AAT GCC AGG CCT GTG CCC AGA CGC TCA GTG GAG AGA     768
Phe Asp Pro Gln Asn Ala Arg Pro Val Pro Arg Arg Ser Val Glu Arg
                245                 250                 255

GCA CCC GGT CCT CAC AGA AGC AGT GAG GCC AGA GGA AGT CTA GTG ACC     816
Ala Pro Gly Pro His Arg Ser Ser Glu Ala Arg Gly Ser Leu Val Thr
            260                 265                 270

AGA ATA CAG CCG CTG GTA CCA CCA CCA TCA CCA CCT CCA TCT CGG CGC     864
Arg Ile Gln Pro Leu Val Pro Pro Pro Ser Pro Pro Pro Ser Arg Arg
        275                 280                 285

CTC AGC CAG CCC TGG CCC CTG CAG CAG CAC TCA GGG CCG TCC AGG ACA     912
```

```
Leu Ser Gln Pro Trp Pro Leu Gln Gln His Ser Gly Pro Ser Arg Thr
    290                 295                 300

GTT CGT CGG TAT CCG GCC ACT GGT GCC AAT GGC CAG CTG ATG TCC AAC      960
Val Arg Arg Tyr Pro Ala Thr Gly Ala Asn Gly Gln Leu Met Ser Asn
305                 310                 315                 320

GCT TTG CCT TCA GGA CTC GAG CTG AGA GAC AGC AGC CCA CAG GCA GCA     1008
Ala Leu Pro Ser Gly Leu Glu Leu Arg Asp Ser Ser Pro Gln Ala Ala
                325                 330                 335

CAT GTG AAC CAT CTC TCA CCC CCC TGG GGG CTG AAC CTC ACC GAG AAA     1056
His Val Asn His Leu Ser Pro Pro Trp Gly Leu Asn Leu Thr Glu Lys
            340                 345                 350

ATC AAG AAA ATC AAA GTC GTC TTC ACC CCC ACC ATC TGC AAG CAG ACC     1104
Ile Lys Lys Ile Lys Val Val Phe Thr Pro Thr Ile Cys Lys Gln Thr
        355                 360                 365

TGT GCC CGG GGA CGC TGT GCC AAC AGC TGT GAG AAG GGT GAC ACC ACC     1152
Cys Ala Arg Gly Arg Cys Ala Asn Ser Cys Glu Lys Gly Asp Thr Thr
    370                 375                 380

ACC TTG TAC AGT CAG GGT GGC CAT GGG CAT GAC CCC AAG TCT GGC TTC     1200
Thr Leu Tyr Ser Gln Gly Gly His Gly His Asp Pro Lys Ser Gly Phe
385                 390                 395                 400

CGT ATC TAT TTC TGC CAA ATC CCC TGC CTG AAT GGT GGC CGC TGC ATC     1248
Arg Ile Tyr Phe Cys Gln Ile Pro Cys Leu Asn Gly Gly Arg Cys Ile
                405                 410                 415

GGC CGG GAC GAG TGC TGG TGT CCA GCC AAC TCC ACA GGA AAG TTC TGC     1296
Gly Arg Asp Glu Cys Trp Cys Pro Ala Asn Ser Thr Gly Lys Phe Cys
            420                 425                 430

CAT CTG CCT GTC CCG CAG CCA GAC AGG GAA CCT GCA GGG CGA GGT TCC     1344
His Leu Pro Val Pro Gln Pro Asp Arg Glu Pro Ala Gly Arg Gly Ser
        435                 440                 445

CGG CAC AGA ACC CTG CTG GAA GGT CCC CTG AAG CAA TCC ACC TTC ACG     1392
Arg His Arg Thr Leu Leu Glu Gly Pro Leu Lys Gln Ser Thr Phe Thr
    450                 455                 460

CTG CCT CTC TCT AAC CAG CTC GCC TCT GTG AAC CCC TCG CTG GTG AAG     1440
Leu Pro Leu Ser Asn Gln Leu Ala Ser Val Asn Pro Ser Leu Val Lys
465                 470                 475                 480

GTG CAA ATT CAT CAC CCG CCT GAG GCC TCT GTG CAG ATT CAC CAG GTG     1488
Val Gln Ile His His Pro Pro Glu Ala Ser Val Gln Ile His Gln Val
                485                 490                 495

GCC CGG GTC CGG GGT GAG CTG GAC CCC GTG CTG GAG GAC AAC AGT GTG     1536
Ala Arg Val Arg Gly Glu Leu Asp Pro Val Leu Glu Asp Asn Ser Val
            500                 505                 510

GAG ACC AGA GCC TCT CAT CGC CCC CAC GGC AAC CTA GGC CAC AGC CCC     1584
Glu Thr Arg Ala Ser His Arg Pro His Gly Asn Leu Gly His Ser Pro
        515                 520                 525

TGG GCC AGC AAC AGC ATA CCC GCT CGG GCC GGA GAG GCC CCT CGG CCA     1632
Trp Ala Ser Asn Ser Ile Pro Ala Arg Ala Gly Glu Ala Pro Arg Pro
    530                 535                 540

CCA CCA GTG CTG TCT AGG CAT TAT GGA CTT CTG GGC CAG TGT TAC CTG     1680
Pro Pro Val Leu Ser Arg His Tyr Gly Leu Leu Gly Gln Cys Tyr Leu
545                 550                 555                 560

AGC ACG GTG AAT GGA CAG TGT GCT AAC CCC CTA GGT AGT CTG ACT TCT     1728
Ser Thr Val Asn Gly Gln Cys Ala Asn Pro Leu Gly Ser Leu Thr Ser
                565                 570                 575

CAG GAG GAC TGC TGT GGC AGT GTG GGG ACC TTC TGG GGG GTG ACC TCC     1776
Gln Glu Asp Cys Cys Gly Ser Val Gly Thr Phe Trp Gly Val Thr Ser
            580                 585                 590

TGT GCT CCC TGC CCA CCC AGA CAA GAG GGT CCA GCC TTC CCA GTG ATT     1824
Cys Ala Pro Cys Pro Pro Arg Gln Glu Gly Pro Ala Phe Pro Val Ile
        595                 600                 605
```

```
GAA AAT GGC CAG CTG GAG TGT CCC CAA GGA TAC AAG AGA CTG AAC CTC       1872
Glu Asn Gly Gln Leu Glu Cys Pro Gln Gly Tyr Lys Arg Leu Asn Leu
    610                 615                 620

AGC CAC TGC CAA GAT ATC AAT GAG TGC CTG ACC CTG GGC CTC TGC AAG       1920
Ser His Cys Gln Asp Ile Asn Glu Cys Leu Thr Leu Gly Leu Cys Lys
625                 630                 635                 640

GAC TCG GAG TGC GTG AAC ACC AGG GGC AGC TAC CTG TGC ACC TGC AGG       1968
Asp Ser Glu Cys Val Asn Thr Arg Gly Ser Tyr Leu Cys Thr Cys Arg
                645                 650                 655

CCT GGC CTC ATG CTG GAT CCG TCA AGG AGC CGC TGC GTA TCG GAC AAG       2016
Pro Gly Leu Met Leu Asp Pro Ser Arg Ser Arg Cys Val Ser Asp Lys
            660                 665                 670

GCT GTC TCC ATG CAG CAG GGA CTA TGC TAC CGG TCA CTG GGG TCT GGT       2064
Ala Val Ser Met Gln Gln Gly Leu Cys Tyr Arg Ser Leu Gly Ser Gly
        675                 680                 685

ACC TGC ACC CTG CCT TTG GTT CAT CGG ATC ACC AAG CAG ATA TGC TGC       2112
Thr Cys Thr Leu Pro Leu Val His Arg Ile Thr Lys Gln Ile Cys Cys
690                 695                 700

TGC AGC CGT GTG GGC AAA GCC TGG GGT AGC ACA TGT GAA CAG TGT CCC       2160
Cys Ser Arg Val Gly Lys Ala Trp Gly Ser Thr Cys Glu Gln Cys Pro
705                 710                 715                 720

CTG CCT GGC ACA GAA GCC TTC AGG GAG ATC TGC CCT GCT GGC CAT GGC       2208
Leu Pro Gly Thr Glu Ala Phe Arg Glu Ile Cys Pro Ala Gly His Gly
                725                 730                 735

TAC ACC TAC TCG AGC TCA GAC ATC CGC CTG TCT ATG AGG AAA GCC GAA       2256
Tyr Thr Tyr Ser Ser Ser Asp Ile Arg Leu Ser Met Arg Lys Ala Glu
            740                 745                 750

GAA GAG GAA CTG GCT AGC CCC TTA AGG GAG CAG ACA GAG CAG AGC ACT       2304
Glu Glu Glu Leu Ala Ser Pro Leu Arg Glu Gln Thr Glu Gln Ser Thr
        755                 760                 765

GCA CCC CCA CCT GGG CAA GCA GAG AGG CAA CCA CTC CGG GCA GCC ACC       2352
Ala Pro Pro Pro Gly Gln Ala Glu Arg Gln Pro Leu Arg Ala Ala Thr
770                 775                 780

GCC ACC TGG ATT GAG GCT GAG ACC CTC CCT GAC AAA GGT GAC TCT CGG       2400
Ala Thr Trp Ile Glu Ala Glu Thr Leu Pro Asp Lys Gly Asp Ser Arg
785                 790                 795                 800

GCT GTT CAG ATC ACA ACC AGT GCT CCC CAC CTA CCT GCC CGG GTA CCA       2448
Ala Val Gln Ile Thr Thr Ser Ala Pro His Leu Pro Ala Arg Val Pro
                805                 810                 815

GGG GAT GCC ACT GGA AGA CCA GCA CCA TCC TTG CCT GGA CAG GGC ATT       2496
Gly Asp Ala Thr Gly Arg Pro Ala Pro Ser Leu Pro Gly Gln Gly Ile
            820                 825                 830

CCA GAG AGT CCA GCA GAA GAG CAA GTG ATT CCC TCC AGT GAT GTC TTG       2544
Pro Glu Ser Pro Ala Glu Glu Gln Val Ile Pro Ser Ser Asp Val Leu
        835                 840                 845

GTG ACA CAC AGC CCC CCA GAC TTT GAT CCA TGT TTT GCT GGA GCC TCC       2592
Val Thr His Ser Pro Pro Asp Phe Asp Pro Cys Phe Ala Gly Ala Ser
850                 855                 860

AAC ATC TGT GGC CCT GGG ACC TGT GTG AGC CTC CCA AAT GGA TAC AGA       2640
Asn Ile Cys Gly Pro Gly Thr Cys Val Ser Leu Pro Asn Gly Tyr Arg
865                 870                 875                 880

TGT GTC TGC AGC CCT GGC TAC CAG CTA CAC CCC AGC CAA GAC TAC TGT       2688
Cys Val Cys Ser Pro Gly Tyr Gln Leu His Pro Ser Gln Asp Tyr Cys
                885                 890                 895

ACT GAT GAC AAC GAG TGT ATG AGG AAC CCC TGT GAA GGA AGA GGG CGC       2736
Thr Asp Asp Asn Glu Cys Met Arg Asn Pro Cys Glu Gly Arg Gly Arg
            900                 905                 910

TGT GTC AAC AGT GTG GGC TCC TAC TCC TGC CTC TGC TAT CCT GGC TAC       2784
Cys Val Asn Ser Val Gly Ser Tyr Ser Cys Leu Cys Tyr Pro Gly Tyr
        915                 920                 925
```

```
ACA CTA GTC ACC CTC GGA GAC ACA CAG GAG TGC CAA GAT ATC GAT GAG      2832
Thr Leu Val Thr Leu Gly Asp Thr Gln Glu Cys Gln Asp Ile Asp Glu
    930                 935                 940

TGT GAG CAG CCC GGG GTG TGC AGT GGT GGG CGA TGC AGC AAC ACG GAG      2880
Cys Glu Gln Pro Gly Val Cys Ser Gly Gly Arg Cys Ser Asn Thr Glu
945                 950                 955                 960

GGC TCG TAC CAC TGC GAG TGT GAT CGG GGC TAC ATC ATG GTC AGG AAA      2928
Gly Ser Tyr His Cys Glu Cys Asp Arg Gly Tyr Ile Met Val Arg Lys
                965                 970                 975

GGA CAC TGT CAA GAT ATC AAC GAA TGC CGT CAC CCT GGT ACC TGC CCT      2976
Gly His Cys Gln Asp Ile Asn Glu Cys Arg His Pro Gly Thr Cys Pro
            980                 985                 990

GAT GGG AGA TGC GTC AAC TCC CCT GGC TCC TAC ACT TGT CTG GCC TGT      3024
Asp Gly Arg Cys Val Asn Ser Pro Gly Ser Tyr Thr Cys Leu Ala Cys
        995                 1000                1005

GAG GAG GGC TAT GTA GGC CAG AGT GGG AGC TGT GTA GAT GTC AAT GAG      3072
Glu Glu Gly Tyr Val Gly Gln Ser Gly Ser Cys Val Asp Val Asn Glu
    1010                1015                1020

TGT CTG ACC CCT GGG ATA TGT ACC CAT GGA AGG TGC ATC AAC ATG GAA      3120
Cys Leu Thr Pro Gly Ile Cys Thr His Gly Arg Cys Ile Asn Met Glu
1025                1030                1035                1040

GGC TCC TTT AGA TGC TCC TGT GAG CCG GGC TAT GAG GTC ACC CCA GAC      3168
Gly Ser Phe Arg Cys Ser Cys Glu Pro Gly Tyr Glu Val Thr Pro Asp
                1045                1050                1055

AAG AAG GGC TGC CGA GAT GTG GAC GAG TGT GCC AGC CGA GCC TCG TGC      3216
Lys Lys Gly Cys Arg Asp Val Asp Glu Cys Ala Ser Arg Ala Ser Cys
            1060                1065                1070

CCC ACG GGC CTC TGC CTC AAC ACG GAG GGC TCC TTC ACC TGC TCA GCC      3264
Pro Thr Gly Leu Cys Leu Asn Thr Glu Gly Ser Phe Thr Cys Ser Ala
        1075                1080                1085

TGT CAG AGC GGG TAC TGG GTG AAC GAA GAT GGC ACT GCC TGT GAA GAC      3312
Cys Gln Ser Gly Tyr Trp Val Asn Glu Asp Gly Thr Ala Cys Glu Asp
    1090                1095                1100

TTG GAT GAA TGT GCC TTC CCT GGA GTC TGC CCC ACA GGC GTC TGC ACC      3360
Leu Asp Glu Cys Ala Phe Pro Gly Val Cys Pro Thr Gly Val Cys Thr
1105                1110                1115                1120

AAT ACT GTA GGC TCC TTC TCC TGC AAG GAC TGT GAC CAG GGC TAC CGG      3408
Asn Thr Val Gly Ser Phe Ser Cys Lys Asp Cys Asp Gln Gly Tyr Arg
                1125                1130                1135

CCC AAC CCC CTG GGC AAC AGA TGC GAA GAT GTG GAT GAG TGT GAA GGT      3456
Pro Asn Pro Leu Gly Asn Arg Cys Glu Asp Val Asp Glu Cys Glu Gly
            1140                1145                1150

CCC CAA AGC AGC TGC CGG GGA GGC GAA TGC AAG AAC ACA GAA GGT TCC      3504
Pro Gln Ser Ser Cys Arg Gly Gly Glu Cys Lys Asn Thr Glu Gly Ser
        1155                1160                1165

TAC CAA TGC CTC TGT CAC CAG GGC TTC CAG CTG GTC AAT GGC ACC ATG      3552
Tyr Gln Cys Leu Cys His Gln Gly Phe Gln Leu Val Asn Gly Thr Met
    1170                1175                1180

TGT GAG GAC GTG AAT GAG TGT GTT GGG GAA GAG CAT TGT GCT CCT CAC      3600
Cys Glu Asp Val Asn Glu Cys Val Gly Glu Glu His Cys Ala Pro His
1185                1190                1195                1200

GGC GAG TGC CTC AAC AGC CTG GGC TCC TTC TTC TGC CTC TGT GCA CCC      3648
Gly Glu Cys Leu Asn Ser Leu Gly Ser Phe Phe Cys Leu Cys Ala Pro
                1205                1210                1215

GGC TTT GCT AGT GCT GAG GGG GGC ACC AGA TGC CAG GAT GTT GAT GAA      3696
Gly Phe Ala Ser Ala Glu Gly Gly Thr Arg Cys Gln Asp Val Asp Glu
            1220                1225                1230

TGT GCA GCC ACA GAC CCG TGT CCG GGA GGA CAC TGT GTC AAC ACA GAG      3744
Cys Ala Ala Thr Asp Pro Cys Pro Gly Gly His Cys Val Asn Thr Glu
```

-continued

```
       1235                1240                1245
GGC TCC TTC AGC TGT CTG TGT GAG ACT GCT TCC TTC CAG CCC TCC CCA       3792
Gly Ser Phe Ser Cys Leu Cys Glu Thr Ala Ser Phe Gln Pro Ser Pro
    1250                1255                1260

GAC AGC GGA GAA TGT TTG GAT ATT GAT GAG TGT GAG GAC CGT GAA GAC       3840
Asp Ser Gly Glu Cys Leu Asp Ile Asp Glu Cys Glu Asp Arg Glu Asp
1265                1270                1275                1280

CCG GTG TGC GGA GCC TGG AGG TGT GAG AAC AGT CCT GGT TCC TAC CGC       3888
Pro Val Cys Gly Ala Trp Arg Cys Glu Asn Ser Pro Gly Ser Tyr Arg
                1285                1290                1295

TGC ATC CTG GAC TGC CAG CCT GGA TTC TAT GTG GCG CCA AAT GGA GAC       3936
Cys Ile Leu Asp Cys Gln Pro Gly Phe Tyr Val Ala Pro Asn Gly Asp
            1300                1305                1310

TGC ATT GAC ATA GAT GAA TGT GCC AAT GAC ACT GTG TGT GGG AAC CAT       3984
Cys Ile Asp Ile Asp Glu Cys Ala Asn Asp Thr Val Cys Gly Asn His
            1315                1320                1325

GGC TTC TGT GAC AAC ACG GAC GGC TCC TTC CGC TGC CTG TGT GAC CAG       4032
Gly Phe Cys Asp Asn Thr Asp Gly Ser Phe Arg Cys Leu Cys Asp Gln
        1330                1335                1340

GGC TTC GAG ACC TCA CCA TCA GGC TGG GAG TGT GTT GAT GTG AAC GAG       4080
Gly Phe Glu Thr Ser Pro Ser Gly Trp Glu Cys Val Asp Val Asn Glu
1345                1350                1355                1360

TGT GAG CTC ATG ATG GCA GTG TGT GGG GAT GCG CTC TGT GAG AAC GTG       4128
Cys Glu Leu Met Met Ala Val Cys Gly Asp Ala Leu Cys Glu Asn Val
                1365                1370                1375

GAA GGC TCC TTC CTG TGC CTT TGC GCC AGT GAC CTT GAG GAG TAC GAC       4176
Glu Gly Ser Phe Leu Cys Leu Cys Ala Ser Asp Leu Glu Glu Tyr Asp
            1380                1385                1390

GCA GAA GAA GGA CAC TGC CGT CCT CGG GTG GCT GGA GCT CAG AGA ATC       4224
Ala Glu Glu Gly His Cys Arg Pro Arg Val Ala Gly Ala Gln Arg Ile
            1395                1400                1405

CCA GAG GTC CGG ACA GAG GAC CAG GCT CCA AGC CTT ATC CGC ATG GAA       4272
Pro Glu Val Arg Thr Glu Asp Gln Ala Pro Ser Leu Ile Arg Met Glu
        1410                1415                1420

TGC TAC TCT GAA CAC AAT GGT GGT CCT CCC TGC TCT CAA ATC CTG GGC       4320
Cys Tyr Ser Glu His Asn Gly Gly Pro Pro Cys Ser Gln Ile Leu Gly
1425                1430                1435                1440

CAG AAC TCC ACA CAG GCC GAG TGC TGC TGC ACT CAG GGT GCC AGA TGG       4368
Gln Asn Ser Thr Gln Ala Glu Cys Cys Cys Thr Gln Gly Ala Arg Trp
                1445                1450                1455

GGA AAG GCC TGT GCG CCC TGC CCA TCT GAG GAC TCA GTT GAA TTC AGT       4416
Gly Lys Ala Cys Ala Pro Cys Pro Ser Glu Asp Ser Val Glu Phe Ser
            1460                1465                1470

CAG CTC TGC CCC AGT GGT CAA GGT TAC ATC CCA GTG GAA GGA GCC TGG       4464
Gln Leu Cys Pro Ser Gly Gln Gly Tyr Ile Pro Val Glu Gly Ala Trp
            1475                1480                1485

ACA TTT GGA CAA ACC ATG TAT ACA GAT GCC GAT GAA TGT GTA CTG TTT       4512
Thr Phe Gly Gln Thr Met Tyr Thr Asp Ala Asp Glu Cys Val Leu Phe
        1490                1495                1500

GGG CCT GCT CTC TGC CAG AAT GGC CGA TGC TCA AAC ATA GTG CCT GGC       4560
Gly Pro Ala Leu Cys Gln Asn Gly Arg Cys Ser Asn Ile Val Pro Gly
1505                1510                1515                1520

TAC ATT TGC CTG TGC AAC CCT GGC TAC CAC TAT GAT GCC TCC AGC AGG       4608
Tyr Ile Cys Leu Cys Asn Pro Gly Tyr His Tyr Asp Ala Ser Ser Arg
                1525                1530                1535

AAG TGC CAG GAT CAC AAC GAA TGC CAG GAC TTG GCC TGT GAG AAC GGT       4656
Lys Cys Gln Asp His Asn Glu Cys Gln Asp Leu Ala Cys Glu Asn Gly
            1540                1545                1550

GAG TGT GTG AAC CAA GAA GGC TCC TTC CAT TGC CTC TGC AAT CCC CCC       4704
```

-continued

```
Glu Cys Val Asn Gln Glu Gly Ser Phe His Cys Leu Cys Asn Pro Pro
            1555                1560                1565

CTC ACC CTA GAC CTC AGT GGG CAG CGC TGT GTG AAC ACG ACC AGC AGC      4752
Leu Thr Leu Asp Leu Ser Gly Gln Arg Cys Val Asn Thr Thr Ser Ser
    1570                1575                1580

ACG GAG GAC TTC CCT GAC CAT GAC ATC CAC ATG GAC ATC TGC TGG AAA      4800
Thr Glu Asp Phe Pro Asp His Asp Ile His Met Asp Ile Cys Trp Lys
1585                1590                1595                1600

AAA GTC ACC AAT GAT GTG TGC AGC CAG CCC TTG CGT GGG CAC CAT ACC      4848
Lys Val Thr Asn Asp Val Cys Ser Gln Pro Leu Arg Gly His His Thr
                1605                1610                1615

ACC TAT ACA GAA TGC TGC TGC CAA GAT GGG GAG GCC TGG AGC CAG CAA      4896
Thr Tyr Thr Glu Cys Cys Cys Gln Asp Gly Glu Ala Trp Ser Gln Gln
            1620                1625                1630

TGC GCT CTG TGC CCG CCC AGG AGC TCT GAG GTC TAC GCT CAG CTG TGC      4944
Cys Ala Leu Cys Pro Pro Arg Ser Ser Glu Val Tyr Ala Gln Leu Cys
        1635                1640                1645

AAC GTG GCT CGG ATT GAG GCA GAG CGC GGA GCA GGG ATC CAC TTC CGG      4992
Asn Val Ala Arg Ile Glu Ala Glu Arg Gly Ala Gly Ile His Phe Arg
    1650                1655                1660

CCA GGC TAT GAG TAT GGC CCT GGC CTG GAC GAT CTG CCT GAA AAC CTC      5040
Pro Gly Tyr Glu Tyr Gly Pro Gly Leu Asp Asp Leu Pro Glu Asn Leu
1665                1670                1675                1680

TAC GGC CCA GAT GGG GCT CCC TTC TAT AAC TAC CTA GGC CCC GAG GAC      5088
Tyr Gly Pro Asp Gly Ala Pro Phe Tyr Asn Tyr Leu Gly Pro Glu Asp
                1685                1690                1695

ACT GCC CCT GAG CCT CCC TTC TCC AAC CCA GCC AGC CAG CCG GGA GAC      5136
Thr Ala Pro Glu Pro Pro Phe Ser Asn Pro Ala Ser Gln Pro Gly Asp
            1700                1705                1710

AAC ACA CCT GTC CTT GAG CCT CCT CTG CAG CCC TCT GAA CTT CAG CCT      5184
Asn Thr Pro Val Leu Glu Pro Pro Leu Gln Pro Ser Glu Leu Gln Pro
        1715                1720                1725

CAC TAT CTA GCC AGC CAC TCA GAA CCC CCT GCC TCC TTC GAA GGC CTT      5232
His Tyr Leu Ala Ser His Ser Glu Pro Pro Ala Ser Phe Glu Gly Leu
    1730                1735                1740

CAG GCT GAG GAA TGT GGC ATC CTG AAT GGC TGT GAG AAT GGC CGC TGC      5280
Gln Ala Glu Glu Cys Gly Ile Leu Asn Gly Cys Glu Asn Gly Arg Cys
1745                1750                1755                1760

GTG CGT GTG CGG GAG GGC TAC ACT TGC GAC TGC TTT GAG GGC TTC CAG      5328
Val Arg Val Arg Glu Gly Tyr Thr Cys Asp Cys Phe Glu Gly Phe Gln
                1765                1770                1775

CTG GAT GCG CCC ACA TTG GCC TGT GTG GAT GTG AAC GAG TGT GAA GAC      5376
Leu Asp Ala Pro Thr Leu Ala Cys Val Asp Val Asn Glu Cys Glu Asp
            1780                1785                1790

TTG AAC GGG CCT GCA CGA CTC TGT GCA CAC GGT CAC TGT GAG AAC ACA      5424
Leu Asn Gly Pro Ala Arg Leu Cys Ala His Gly His Cys Glu Asn Thr
        1795                1800                1805

GAG GGT TCC TAT CGC TGC CAC TGT TCG CCA GGT TAC GTG GCA GAG CCA      5472
Glu Gly Ser Tyr Arg Cys His Cys Ser Pro Gly Tyr Val Ala Glu Pro
    1810                1815                1820

GGC CCC CCA CAC TGT GCG GCC AAG GAG                                  5499
Gly Pro Pro His Cys Ala Ala Lys Glu
1825                1830
```

(2) INFORMATION FOR SEQ ID NO: 2:

(i) SEQUENCE CHARACTERISTICS:
        (A) LENGTH: 1833 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Glu Ser Thr Ser Pro Arg Gly Leu Arg Cys Pro Gln Leu Cys Ser
 1               5                  10                  15

His Ser Gly Ala Met Arg Ala Pro Thr Thr Ala Arg Cys Ser Gly Cys
            20                  25                  30

Ile Gln Arg Val Arg Trp Arg Gly Phe Leu Pro Leu Val Leu Ala Val
         35                  40                  45

Leu Met Gly Thr Ser His Ala Gln Arg Asp Ser Ile Gly Arg Tyr Glu
     50                  55                  60

Pro Ala Ser Arg Asp Ala Asn Arg Leu Trp His Pro Val Gly Ser His
 65                  70                  75                  80

Pro Ala Ala Ala Ala Lys Val Tyr Ser Leu Phe Arg Glu Pro Asp
                85                  90                  95

Ala Pro Val Pro Gly Leu Ser Pro Ser Glu Trp Asn Gln Pro Ala Gln
            100                 105                 110

Gly Asn Pro Gly Trp Leu Ala Glu Ala Glu Ala Arg Arg Pro Pro Arg
        115                 120                 125

Thr Gln Gln Leu Arg Arg Val Gln Pro Pro Val Gln Thr Arg Arg Ser
130                 135                 140

His Pro Arg Gly Gln Gln Gln Ile Ala Ala Arg Ala Ala Pro Ser Val
145                 150                 155                 160

Ala Arg Leu Glu Thr Pro Gln Arg Pro Ala Ala Arg Arg Gly Arg
            165                 170                 175

Leu Thr Gly Arg Asn Val Cys Gly Gln Cys Cys Pro Gly Trp Thr
            180                 185                 190

Thr Ser Asn Ser Thr Asn His Cys Ile Lys Pro Val Cys Gln Pro Pro
        195                 200                 205

Cys Gln Asn Arg Gly Ser Cys Ser Arg Pro Gln Val Cys Ile Cys Arg
    210                 215                 220

Ser Gly Phe Arg Gly Ala Arg Cys Glu Glu Val Ile Pro Glu Glu Glu
225                 230                 235                 240

Phe Asp Pro Gln Asn Ala Arg Pro Val Pro Arg Arg Ser Val Glu Arg
                245                 250                 255

Ala Pro Gly Pro His Arg Ser Ser Glu Ala Arg Gly Ser Leu Val Thr
            260                 265                 270

Arg Ile Gln Pro Leu Val Pro Pro Ser Pro Pro Ser Arg Arg
        275                 280                 285

Leu Ser Gln Pro Trp Pro Leu Gln Gln His Ser Gly Pro Ser Arg Thr
290                 295                 300

Val Arg Arg Tyr Pro Ala Thr Gly Ala Asn Gly Gln Leu Met Ser Asn
305                 310                 315                 320

Ala Leu Pro Ser Gly Leu Glu Leu Arg Asp Ser Ser Pro Gln Ala Ala
                325                 330                 335

His Val Asn His Leu Ser Pro Pro Trp Gly Leu Asn Leu Thr Glu Lys
            340                 345                 350

Ile Lys Lys Ile Lys Val Val Phe Thr Pro Thr Ile Cys Lys Gln Thr
        355                 360                 365

Cys Ala Arg Gly Arg Cys Ala Asn Ser Cys Glu Lys Gly Asp Thr Thr
    370                 375                 380

Thr Leu Tyr Ser Gln Gly Gly His Gly His Asp Pro Lys Ser Gly Phe
385                 390                 395                 400
```

-continued

```
Arg Ile Tyr Phe Cys Gln Ile Pro Cys Leu Asn Gly Arg Cys Ile
                405                 410                 415

Gly Arg Asp Glu Cys Trp Cys Pro Ala Asn Ser Thr Gly Lys Phe Cys
            420                 425                 430

His Leu Pro Val Pro Gln Pro Asp Arg Glu Pro Ala Gly Arg Gly Ser
        435                 440                 445

Arg His Arg Thr Leu Leu Glu Gly Pro Leu Lys Gln Ser Thr Phe Thr
    450                 455                 460

Leu Pro Leu Ser Asn Gln Leu Ala Ser Val Asn Pro Ser Leu Val Lys
465                 470                 475                 480

Val Gln Ile His His Pro Pro Glu Ala Ser Val Gln Ile His Gln Val
                485                 490                 495

Ala Arg Val Arg Gly Glu Leu Asp Pro Val Leu Glu Asp Asn Ser Val
            500                 505                 510

Glu Thr Arg Ala Ser His Arg Pro His Gly Asn Leu Gly His Ser Pro
        515                 520                 525

Trp Ala Ser Asn Ser Ile Pro Ala Arg Ala Gly Glu Ala Pro Arg Pro
    530                 535                 540

Pro Pro Val Leu Ser Arg His Tyr Gly Leu Leu Gly Gln Cys Tyr Leu
545                 550                 555                 560

Ser Thr Val Asn Gly Gln Cys Ala Asn Pro Leu Gly Ser Leu Thr Ser
                565                 570                 575

Gln Glu Asp Cys Cys Gly Ser Val Gly Thr Phe Trp Gly Val Thr Ser
            580                 585                 590

Cys Ala Pro Cys Pro Pro Arg Gln Glu Gly Pro Ala Phe Pro Val Ile
        595                 600                 605

Glu Asn Gly Gln Leu Glu Cys Pro Gln Gly Tyr Lys Arg Leu Asn Leu
    610                 615                 620

Ser His Cys Gln Asp Ile Asn Glu Cys Leu Thr Leu Gly Leu Cys Lys
625                 630                 635                 640

Asp Ser Glu Cys Val Asn Thr Arg Gly Ser Tyr Leu Cys Thr Cys Arg
                645                 650                 655

Pro Gly Leu Met Leu Asp Pro Ser Arg Ser Arg Cys Val Ser Asp Lys
            660                 665                 670

Ala Val Ser Met Gln Gln Gly Leu Cys Tyr Arg Ser Leu Gly Ser Gly
        675                 680                 685

Thr Cys Thr Leu Pro Leu Val His Arg Ile Thr Lys Gln Ile Cys Cys
    690                 695                 700

Cys Ser Arg Val Gly Lys Ala Trp Gly Ser Thr Cys Glu Gln Cys Pro
705                 710                 715                 720

Leu Pro Gly Thr Glu Ala Phe Arg Glu Ile Cys Pro Ala Gly His Gly
                725                 730                 735

Tyr Thr Tyr Ser Ser Ser Asp Ile Arg Leu Ser Met Arg Lys Ala Glu
            740                 745                 750

Glu Glu Glu Leu Ala Ser Pro Leu Arg Glu Gln Thr Glu Gln Ser Thr
        755                 760                 765

Ala Pro Pro Gly Gln Ala Glu Arg Gln Pro Leu Arg Ala Ala Thr
    770                 775                 780

Ala Thr Trp Ile Glu Ala Glu Thr Leu Pro Asp Lys Gly Asp Ser Arg
785                 790                 795                 800

Ala Val Gln Ile Thr Thr Ser Ala Pro His Leu Pro Ala Arg Val Pro
                805                 810                 815

Gly Asp Ala Thr Gly Arg Pro Ala Pro Ser Leu Pro Gly Gln Gly Ile
```

-continued

```
                820                 825                 830
Pro Glu Ser Pro Ala Glu Gln Val Ile Pro Ser Ser Asp Val Leu
            835                 840                 845
Val Thr His Ser Pro Pro Asp Phe Asp Pro Cys Phe Ala Gly Ala Ser
850                 855                 860
Asn Ile Cys Gly Pro Gly Thr Cys Val Ser Leu Pro Asn Gly Tyr Arg
865                 870                 875                 880
Cys Val Cys Ser Pro Gly Tyr Gln Leu His Pro Ser Gln Asp Tyr Cys
                885                 890                 895
Thr Asp Asp Asn Glu Cys Met Arg Asn Pro Cys Glu Gly Arg Gly Arg
            900                 905                 910
Cys Val Asn Ser Val Gly Ser Tyr Ser Cys Leu Cys Tyr Pro Gly Tyr
            915                 920                 925
Thr Leu Val Thr Leu Gly Asp Thr Gln Glu Cys Gln Asp Ile Asp Glu
            930                 935                 940
Cys Glu Gln Pro Gly Val Cys Ser Gly Gly Arg Cys Ser Asn Thr Glu
945                 950                 955                 960
Gly Ser Tyr His Cys Glu Cys Asp Arg Gly Tyr Ile Met Val Arg Lys
                965                 970                 975
Gly His Cys Gln Asp Ile Asn Glu Cys Arg His Pro Gly Thr Cys Pro
            980                 985                 990
Asp Gly Arg Cys Val Asn Ser Pro Gly Ser Tyr Thr Cys Leu Ala Cys
            995                 1000                1005
Glu Glu Gly Tyr Val Gly Gln Ser Gly Ser Cys Val Asp Val Asn Glu
        1010                1015                1020
Cys Leu Thr Pro Gly Ile Cys Thr His Gly Arg Cys Ile Asn Met Glu
1025                1030                1035                1040
Gly Ser Phe Arg Cys Ser Cys Glu Pro Gly Tyr Glu Val Thr Pro Asp
                1045                1050                1055
Lys Lys Gly Cys Arg Asp Val Asp Glu Cys Ala Ser Arg Ala Ser Cys
            1060                1065                1070
Pro Thr Gly Leu Cys Leu Asn Thr Glu Gly Ser Phe Thr Cys Ser Ala
            1075                1080                1085
Cys Gln Ser Gly Tyr Trp Val Asn Glu Asp Gly Thr Ala Cys Glu Asp
        1090                1095                1100
Leu Asp Glu Cys Ala Phe Pro Gly Val Cys Pro Thr Gly Val Cys Thr
1105                1110                1115                1120
Asn Thr Val Gly Ser Phe Ser Cys Lys Asp Cys Asp Gln Gly Tyr Arg
                1125                1130                1135
Pro Asn Pro Leu Gly Asn Arg Cys Glu Asp Val Asp Glu Cys Glu Gly
            1140                1145                1150
Pro Gln Ser Ser Cys Arg Gly Gly Glu Cys Lys Asn Thr Glu Gly Ser
            1155                1160                1165
Tyr Gln Cys Leu Cys His Gln Gly Phe Gln Leu Val Asn Gly Thr Met
        1170                1175                1180
Cys Glu Asp Val Asn Glu Cys Val Gly Glu Glu His Cys Ala Pro His
1185                1190                1195                1200
Gly Glu Cys Leu Asn Ser Leu Gly Ser Phe Phe Cys Leu Cys Ala Pro
                1205                1210                1215
Gly Phe Ala Ser Ala Glu Gly Gly Thr Arg Cys Gln Asp Val Asp Glu
            1220                1225                1230
Cys Ala Ala Thr Asp Pro Cys Pro Gly Gly His Cys Val Asn Thr Glu
            1235                1240                1245
```

```
Gly Ser Phe Ser Cys Leu Cys Glu Thr Ala Ser Phe Gln Pro Ser Pro
    1250                1255                1260

Asp Ser Gly Glu Cys Leu Asp Ile Asp Glu Cys Glu Asp Arg Glu Asp
1265            1270                1275                1280

Pro Val Cys Gly Ala Trp Arg Cys Glu Asn Ser Pro Gly Ser Tyr Arg
            1285                1290                1295

Cys Ile Leu Asp Cys Gln Pro Gly Phe Tyr Val Ala Pro Asn Gly Asp
        1300                1305                1310

Cys Ile Asp Ile Asp Glu Cys Ala Asn Asp Thr Val Cys Gly Asn His
    1315                1320                1325

Gly Phe Cys Asp Asn Thr Asp Gly Ser Phe Arg Cys Leu Cys Asp Gln
    1330                1335                1340

Gly Phe Glu Thr Ser Pro Ser Gly Trp Glu Cys Val Asp Val Asn Glu
1345            1350                1355                1360

Cys Glu Leu Met Met Ala Val Cys Gly Asp Ala Leu Cys Glu Asn Val
            1365                1370                1375

Glu Gly Ser Phe Leu Cys Leu Cys Ala Ser Asp Leu Glu Glu Tyr Asp
        1380                1385                1390

Ala Glu Glu Gly His Cys Arg Pro Arg Val Ala Gly Ala Gln Arg Ile
        1395                1400                1405

Pro Glu Val Arg Thr Glu Asp Gln Ala Pro Ser Leu Ile Arg Met Glu
    1410                1415                1420

Cys Tyr Ser Glu His Asn Gly Gly Pro Pro Cys Ser Gln Ile Leu Gly
1425            1430                1435                1440

Gln Asn Ser Thr Gln Ala Glu Cys Cys Thr Gln Gly Ala Arg Trp
            1445                1450                1455

Gly Lys Ala Cys Ala Pro Cys Pro Ser Glu Asp Ser Val Glu Phe Ser
            1460                1465                1470

Gln Leu Cys Pro Ser Gly Gln Gly Tyr Ile Pro Val Glu Gly Ala Trp
        1475                1480                1485

Thr Phe Gly Gln Thr Met Tyr Thr Asp Ala Asp Glu Cys Val Leu Phe
    1490                1495                1500

Gly Pro Ala Leu Cys Gln Asn Gly Arg Cys Ser Asn Ile Val Pro Gly
1505            1510                1515                1520

Tyr Ile Cys Leu Cys Asn Pro Gly Tyr His Tyr Asp Ala Ser Ser Arg
            1525                1530                1535

Lys Cys Gln Asp His Asn Glu Cys Gln Asp Leu Ala Cys Glu Asn Gly
            1540                1545                1550

Glu Cys Val Asn Gln Glu Gly Ser Phe His Cys Leu Cys Asn Pro Pro
        1555                1560                1565

Leu Thr Leu Asp Leu Ser Gly Gln Arg Cys Val Asn Thr Thr Ser Ser
    1570                1575                1580

Thr Glu Asp Phe Pro Asp His Asp Ile His Met Asp Ile Cys Trp Lys
1585            1590                1595                1600

Lys Val Thr Asn Asp Val Cys Ser Gln Pro Leu Arg Gly His His Thr
            1605                1610                1615

Thr Tyr Thr Glu Cys Cys Cys Gln Asp Gly Glu Ala Trp Ser Gln Gln
            1620                1625                1630

Cys Ala Leu Cys Pro Pro Arg Ser Ser Glu Val Tyr Ala Gln Leu Cys
        1635                1640                1645

Asn Val Ala Arg Ile Glu Ala Glu Arg Gly Ala Gly Ile His Phe Arg
    1650                1655                1660
```

-continued

```
Pro Gly Tyr Glu Tyr Gly Pro Gly Leu Asp Asp Leu Pro Glu Asn Leu
1665                1670                1675                1680

Tyr Gly Pro Asp Gly Ala Pro Phe Tyr Asn Tyr Leu Gly Pro Glu Asp
                1685                1690                1695

Thr Ala Pro Glu Pro Pro Phe Ser Asn Pro Ala Ser Gln Pro Gly Asp
                1700                1705                1710

Asn Thr Pro Val Leu Glu Pro Pro Leu Gln Pro Ser Glu Leu Gln Pro
            1715                1720                1725

His Tyr Leu Ala Ser His Ser Glu Pro Pro Ala Ser Phe Glu Gly Leu
            1730                1735                1740

Gln Ala Glu Glu Cys Gly Ile Leu Asn Gly Cys Glu Asn Gly Arg Cys
1745                1750                1755                1760

Val Arg Val Arg Glu Gly Tyr Thr Cys Asp Cys Phe Glu Gly Phe Gln
                1765                1770                1775

Leu Asp Ala Pro Thr Leu Ala Cys Val Asp Val Asn Glu Cys Glu Asp
                1780                1785                1790

Leu Asn Gly Pro Ala Arg Leu Cys Ala His Gly His Cys Glu Asn Thr
            1795                1800                1805

Glu Gly Ser Tyr Arg Cys His Cys Ser Pro Gly Tyr Val Ala Glu Pro
        1810                1815                1820

Gly Pro Pro His Cys Ala Ala Lys Glu
1825                1830

(2) INFORMATION FOR SEQ ID NO: 3:

(i) SEQUENCE CHARACTERISTICS:
        (A) LENGTH: 3759 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..3759

(xi) SEQUENCE DESCRIPTION: SEQ ID NO: 3:

ATG CGC CAG GCC GGC GGA TTG GGG CTG CTG GCA CTA CTC CTG CTG GCG      48
Met Arg Gln Ala Gly Gly Leu Gly Leu Leu Ala Leu Leu Leu Leu Ala
1               5                   10                  15

CTG CTG GGC CCC GGC GGC CGA GGG GTG GGC CGG CCG GGC AGC GGG GCA      96
Leu Leu Gly Pro Gly Gly Arg Gly Val Gly Arg Pro Gly Ser Gly Ala
                20                  25                  30

CAG GCG GGG GCG GGG CGC TGG GCC CAA CGC TTC AAG GTG GTC TTT GCG     144
Gln Ala Gly Ala Gly Arg Trp Ala Gln Arg Phe Lys Val Val Phe Ala
            35                  40                  45

CCT GTG ATC TGC AAG CGG ACC TGT CTG AAG GGC CAG TGT CGG GAC AGC     192
Pro Val Ile Cys Lys Arg Thr Cys Leu Lys Gly Gln Cys Arg Asp Ser
50                  55                  60

TGT CAG CAG GGC TCC AAC ATG ACG CTC ATC GGA GAG AAC GGC CAC AGC     240
Cys Gln Gln Gly Ser Asn Met Thr Leu Ile Gly Glu Asn Gly His Ser
65                  70                  75                  80

ACC GAC ACG CTC ACC GGT TCT GCC TTC CGC GTG GTG GTG TGC CCT CTA     288
Thr Asp Thr Leu Thr Gly Ser Ala Phe Arg Val Val Val Cys Pro Leu
                85                  90                  95

CCC TGC ATG AAC GGT GGC CAG TGC TCT TCC CGA AAC CAG TGC CTG TGT     336
Pro Cys Met Asn Gly Gly Gln Cys Ser Ser Arg Asn Gln Cys Leu Cys
                100                 105                 110

CCC CCG GAT TTC ACG GGC GCC TTC TGC CAG GTG CCT GCT GCA GGA ACC     384
Pro Pro Asp Phe Thr Gly Arg Phe Cys Gln Val Pro Ala Ala Gly Thr
            115                 120                 125
```

```
GGA GCT GGC ACC GGG AGT TCA GGC CCC GGC TGG CCC GAC CGG GCC ATG        432
Gly Ala Gly Thr Gly Ser Ser Gly Pro Gly Trp Pro Asp Arg Ala Met
        130                 135                 140

TCC ACA GGC CCG CTG CCG CCC CTT GCC CCA GAA GGA GAG TCT GTG GCT        480
Ser Thr Gly Pro Leu Pro Pro Leu Ala Pro Glu Gly Glu Ser Val Ala
145                 150                 155                 160

AGC AAA CAC GCC ATT TAC GCG GTG CAG GTG ATC GCA GAT CCT CCC GGG        528
Ser Lys His Ala Ile Tyr Ala Val Gln Val Ile Ala Asp Pro Pro Gly
                165                 170                 175

CCG GGG GAG GGT CCT CCT GCA CAA CAT GCA GCC TTC TTG GTG CCC CTG        576
Pro Gly Glu Gly Pro Pro Ala Gln His Ala Ala Phe Leu Val Pro Leu
        180                 185                 190

GGG CCA GGA CAA ATC TCG GCA GAA GTG CAG GCT CCG CCC CCC GTG GTG        624
Gly Pro Gly Gln Ile Ser Ala Glu Val Gln Ala Pro Pro Pro Val Val
            195                 200                 205

AAC GTG CGT GTC CAT CAC CCT CCT GAA GCT TCC GTT CAG GTG CAC CGC        672
Asn Val Arg Val His His Pro Pro Glu Ala Ser Val Gln Val His Arg
        210                 215                 220

ATC GAG GGG CCG AAC GCT GAA GGC CCA GCC TCT TCC CAG CAC TTG CTG        720
Ile Glu Gly Pro Asn Ala Glu Gly Pro Ala Ser Ser Gln His Leu Leu
225                 230                 235                 240

CCG CAT CCC AAG CCC CCG CAC CCG AGG CCA CCC ACT CAA AAG CCA CTG        768
Pro His Pro Lys Pro Pro His Pro Arg Pro Pro Thr Gln Lys Pro Leu
                245                 250                 255

GGC CGC TGC TTC CAG GAC ACA TTG CCC AAG CAG CCT TGT GGC AGC AAC        816
Gly Arg Cys Phe Gln Asp Thr Leu Pro Lys Gln Pro Cys Gly Ser Asn
        260                 265                 270

CCT TTG CCT GGC CTT ACC AAG CAG GAA GAT TGC TGC GGT AGC ATC GGT        864
Pro Leu Pro Gly Leu Thr Lys Gln Glu Asp Cys Cys Gly Ser Ile Gly
            275                 280                 285

ACT GCC TGG GGA CAA AGC AAG TGT CAC AAG TGC CCA CAG CTT CAG TAT        912
Thr Ala Trp Gly Gln Ser Lys Cys His Lys Cys Pro Gln Leu Gln Tyr
        290                 295                 300

ACA GGG GTG CAG AAG CCT GTA CCT GTA CGT GGG GAG GTG GGT GCT GAC        960
Thr Gly Val Gln Lys Pro Val Pro Val Arg Gly Glu Val Gly Ala Asp
305                 310                 315                 320

TGC CCC CAG GGC TAC AAG AGG CTC AAC AGC ACC CAC TGC CAG GAT ATC       1008
Cys Pro Gln Gly Tyr Lys Arg Leu Asn Ser Thr His Cys Gln Asp Ile
                325                 330                 335

AAC GAA TGT GCG ATG CCC GGG AAT GTG TGC CAT GGT GAC TGC CTC AAC       1056
Asn Glu Cys Ala Met Pro Gly Asn Val Cys His Gly Asp Cys Leu Asn
        340                 345                 350

AAC CCT GGC TCT TAT CGC TGT GTC TGC CCG CCC GGT CAT AGC TTG GGT       1104
Asn Pro Gly Ser Tyr Arg Cys Val Cys Pro Pro Gly His Ser Leu Gly
            355                 360                 365

CCC CTC GCA GCA CAG TGC ATT GCC GAC AAA CCA GAG GAG AAG AGC CTG       1152
Pro Leu Ala Ala Gln Cys Ile Ala Asp Lys Pro Glu Glu Lys Ser Leu
        370                 375                 380

TGT TTC CGC CTT GTG AGC ACC GAA CAC CAG TGC CAG CAC CCT CTG ACC       1200
Cys Phe Arg Leu Val Ser Thr Glu His Gln Cys Gln His Pro Leu Thr
385                 390                 395                 400

ACA CGC CTA ACC CGC CAG CTC TGC TGC TGT AGT GTG GGT AAA GCC TGG       1248
Thr Arg Leu Thr Arg Gln Leu Cys Cys Cys Ser Val Gly Lys Ala Trp
                405                 410                 415

GGT GCC CGG TGC CAG CGC TGC CCG GCA GAT GGT ACA GCA GCC TTC AAG       1296
Gly Ala Arg Cys Gln Arg Cys Pro Ala Asp Gly Thr Ala Ala Phe Lys
        420                 425                 430

GAG ATC TGC CCC GGC TGG GAA AGG GTA CCA TAT CCT CAC CTC CCA CCA       1344
Glu Ile Cys Pro Gly Trp Glu Arg Val Pro Tyr Pro His Leu Pro Pro
```

```
                435                 440                 445
GAC GCT CAC CAT CCA GGG GGA AAG CGA CTT CTC CCT CTT CCT GCA CCC      1392
Asp Ala His His Pro Gly Gly Lys Arg Leu Leu Pro Leu Pro Ala Pro
            450                 455                 460

GAC GGG CCA CCC AAA CCC CAG CAG CTT CCT GAA AGC CCC AGC CGA GCA      1440
Asp Gly Pro Pro Lys Pro Gln Gln Leu Pro Glu Ser Pro Ser Arg Ala
465                 470                 475                 480

CCA CCC CTC GAG GAC ACA GAG GAA GAG AGA GGA GTG ACC ATG GAT CCA      1488
Pro Pro Leu Glu Asp Thr Glu Glu Glu Arg Gly Val Thr Met Asp Pro
                485                 490                 495

CCA GTG AGT GAG GAG CGA TCG GTG CAG CAG AGC CAC CCC ACT ACC ACC      1536
Pro Val Ser Glu Glu Arg Ser Val Gln Gln Ser His Pro Thr Thr Thr
            500                 505                 510

ACC TCA CCC CCC CGG CCT TAC CCA GAG CTC ATC TCT CGC CCC TCC CCA      1584
Thr Ser Pro Pro Arg Pro Tyr Pro Glu Leu Ile Ser Arg Pro Ser Pro
            515                 520                 525

CCT ACC TTC CAC CGG TTC CTG CCA GAC TTG CCC CCA TCC CGA AGT GCA      1632
Pro Thr Phe His Arg Phe Leu Pro Asp Leu Pro Pro Ser Arg Ser Ala
530                 535                 540

GTG GAG ATC GCC CCC ACT CAG GTC ACA GAG ACC GAT GAG TGC CGA TTG      1680
Val Glu Ile Ala Pro Thr Gln Val Thr Glu Thr Asp Glu Cys Arg Leu
545                 550                 555                 560

AAC CAG AAT ATC TGT GGC CAT GGA CAG TGT GTG CCT GGC CCC TCG GAT      1728
Asn Gln Asn Ile Cys Gly His Gly Gln Cys Val Pro Gly Pro Ser Asp
                565                 570                 575

TAC TCC TGC CAC TGC AAC GCT GGC TAC CGG TCA CAC CCG CAG CAC CGC      1776
Tyr Ser Cys His Cys Asn Ala Gly Tyr Arg Ser His Pro Gln His Arg
                580                 585                 590

TAC TGT GTT GAT GTG AAC GAG TGC GAG GCA GAG CCC TGC GGC CCC GGG      1824
Tyr Cys Val Asp Val Asn Glu Cys Glu Ala Glu Pro Cys Gly Pro Gly
            595                 600                 605

AAA GGC ATC TGT ATG AAC ACT GGT GGC TCC TAC AAT TGT CAC TGC AAC      1872
Lys Gly Ile Cys Met Asn Thr Gly Gly Ser Tyr Asn Cys His Cys Asn
            610                 615                 620

CGA GGC TAC CGC CTC CAC GTG GGT GCA GGG GGC CGC TCG TGC GTG GAC      1920
Arg Gly Tyr Arg Leu His Val Gly Ala Gly Gly Arg Ser Cys Val Asp
625                 630                 635                 640

CTG AAC GAG TGC GCC AAG CCT CAC CTG TGT GGG GAC GGT GGC TTC TGC      1968
Leu Asn Glu Cys Ala Lys Pro His Leu Cys Gly Asp Gly Gly Phe Cys
                645                 650                 655

ATC AAC TTC CCT GGT CAC TAC AAA TGC AAC TGC TAT CCT GGC TAC CGG      2016
Ile Asn Phe Pro Gly His Tyr Lys Cys Asn Cys Tyr Pro Gly Tyr Arg
            660                 665                 670

CTC AAG GCC TCC CGA CCG CCC ATT TGC GAA GAC ATC GAC GAG TGT CGC      2064
Leu Lys Ala Ser Arg Pro Pro Ile Cys Glu Asp Ile Asp Glu Cys Arg
            675                 680                 685

GAC CCT AGC ACC TGC CCT GAT GGC AAA TGT GAA AAC AAA CCT GGC AGC      2112
Asp Pro Ser Thr Cys Pro Asp Gly Lys Cys Glu Asn Lys Pro Gly Ser
            690                 695                 700

TTC AAG TGC ATC GCC TGC CAG CCT GGC TAC CGT AGC CAG GGG GGC GGG      2160
Phe Lys Cys Ile Ala Cys Gln Pro Gly Tyr Arg Ser Gln Gly Gly Gly
705                 710                 715                 720

GCC TGT CGT GAT GTC AAC GAA TGC TCC GAG GGT ACC CCC TGC TCT CCT      2208
Ala Cys Arg Asp Val Asn Glu Cys Ser Glu Gly Thr Pro Cys Ser Pro
                725                 730                 735

GGA TGG TGT GAG AAC CTT CCG GGT TCT TAC CGT TGC ACG TGT GCC CAG      2256
Gly Trp Cys Glu Asn Leu Pro Gly Ser Tyr Arg Cys Thr Cys Ala Gln
                740                 745                 750

GGG ATA CGA ACC CGC ACA GGA CGC CTC AGT TGC ATA GAC GTG GAT GAG      2304
```

```
                                                         -continued

Gly Ile Arg Thr Arg Thr Gly Arg Leu Ser Cys Ile Asp Val Asp Glu
            755                 760                 765
TGT GAG GCT GGG AAA GTG TGC CAA GAT GGC ATC TGC ACG AAC ACA CCA    2352
Cys Glu Ala Gly Lys Val Cys Gln Asp Gly Ile Cys Thr Asn Thr Pro
        770                 775                 780
GGC TCT TTC CAG TGT CAG TGC CTC TCC GGC TAT CAT CTG TCA AGG GAT    2400
Gly Ser Phe Gln Cys Gln Cys Leu Ser Gly Tyr His Leu Ser Arg Asp
785                 790                 795                 800
CGG AGC CGC TGT GAG GAC ATT GAT GAA TGT GAC TTC CCT GCG GCC TGC    2448
Arg Ser Arg Cys Glu Asp Ile Asp Glu Cys Asp Phe Pro Ala Ala Cys
                805                 810                 815
ATC GGG GGT GAC TGC ATC AAT ACC AAT GGT TCC TAC AGA TGT CTC TGT    2496
Ile Gly Gly Asp Cys Ile Asn Thr Asn Gly Ser Tyr Arg Cys Leu Cys
            820                 825                 830
CCC CTG GGT CAT CGG TTG GTG GGC GGC AGG AAG TGC AAG AAA GAT ATA    2544
Pro Leu Gly His Arg Leu Val Gly Gly Arg Lys Cys Lys Lys Asp Ile
        835                 840                 845
GAT GAG TGC AGC CAG GAC CCA GGC CTG TGC CTG CCC CAT GCC TGC GAG    2592
Asp Glu Cys Ser Gln Asp Pro Gly Leu Cys Leu Pro His Ala Cys Glu
850                 855                 860
AAC CTC CAG GGC TCC TAT GTC TGT GTC TGT GAT GAG GGT TTC ACA CTC    2640
Asn Leu Gln Gly Ser Tyr Val Cys Val Cys Asp Glu Gly Phe Thr Leu
865                 870                 875                 880
ACC CAG GAC CAG CAT GGG TGT GAG GAG GTG GAG CAG CCC CAC CAC AAG    2688
Thr Gln Asp Gln His Gly Cys Glu Glu Val Glu Gln Pro His His Lys
                885                 890                 895
AAG GAG TGC TAC CTT AAC TTC GAT GAC ACA GTG TTC TGT GAC AGC GTA    2736
Lys Glu Cys Tyr Leu Asn Phe Asp Asp Thr Val Phe Cys Asp Ser Val
            900                 905                 910
TTG GCT ACC AAT GTC ACT CAG CAG GAA TGC TGT TGC TCT CTG GGA GCT    2784
Leu Ala Thr Asn Val Thr Gln Gln Glu Cys Cys Cys Ser Leu Gly Ala
        915                 920                 925
GGC TGG GGA GAC CAC TGC GAA ATC TAT CCC TGT CCA GTC TAC AGC TCA    2832
Gly Trp Gly Asp His Cys Glu Ile Tyr Pro Cys Pro Val Tyr Ser Ser
930                 935                 940
GCC GAA TTT CAC AGC CTG GTG CCT GAT GGG AAA AGG CTA CAC TCA GGA    2880
Ala Glu Phe His Ser Leu Val Pro Asp Gly Lys Arg Leu His Ser Gly
945                 950                 955                 960
CAA CAA CAT TGT GAA CTA TGC ATT CCT GCC CAC CGT GAC ATC GAC GAA    2928
Gln Gln His Cys Glu Leu Cys Ile Pro Ala His Arg Asp Ile Asp Glu
                965                 970                 975
TGC ATA TTG TTT GGG GCA GAG ATC TGC AAG GAG GGC AAG TGT GTG AAC    2976
Cys Ile Leu Phe Gly Ala Glu Ile Cys Lys Glu Gly Lys Cys Val Asn
            980                 985                 990
ACG CAG CCC GGC TAC GAG TGC TAC TGC AAG CAG GGC TTC TAC TAC GAT    3024
Thr Gln Pro Gly Tyr Glu Cys Tyr Cys Lys Gln Gly Phe Tyr Tyr Asp
        995                 1000                1005
GGC AAC CTG CTG GAG TGC GTG GAC GTG GAT GAG TGC TTG GAT GAG TCT    3072
Gly Asn Leu Leu Glu Cys Val Asp Val Asp Glu Cys Leu Asp Glu Ser
        1010                1015                1020
AAC TGC AGG AAC GGA GTG TGT GAG AAC ACA CGT GGC GGC TAC CGC TGT    3120
Asn Cys Arg Asn Gly Val Cys Glu Asn Thr Arg Gly Gly Tyr Arg Cys
1025                1030                1035                1040
GCC TGC ACT CCG CCG GCA GAG TAC AGT CCC GCA CAG GCC CAG TGT CTG    3168
Ala Cys Thr Pro Pro Ala Glu Tyr Ser Pro Ala Gln Ala Gln Cys Leu
        1045                1050                1055
ATC CCG GAG AGA TGG AGC ACG CCC CAG AGA GAC GTG AAG TGT GCT GGG    3216
Ile Pro Glu Arg Trp Ser Thr Pro Gln Arg Asp Val Lys Cys Ala Gly
        1060                1065                1070
```

```
GCC AGC GAG GAG AGG ACG GCA TGT GTA TGG GGC CCC TGG GCG GGA CCT       3264
Ala Ser Glu Glu Arg Thr Ala Cys Val Trp Gly Pro Trp Ala Gly Pro
        1075                1080                1085

GCC CTC ACT TTT GAT GAC TGC TGC TGC CGC CAG CCG GGC TGG GGT ACC       3312
Ala Leu Thr Phe Asp Asp Cys Cys Cys Arg Gln Pro Arg Leu Gly Thr
    1090                1095                1100

CAG TGC AGA CCG TGC CCG CCA CGT GGC ACC GGG TCC CAG TGC CCG ACT       3360
Gln Cys Arg Pro Cys Pro Pro Arg Gly Thr Gly Ser Gln Cys Pro Thr
1105                1110                1115                1120

TCA CAG AGT GAG AGC AAT TCT TTC TGG GAC ACA AGC CCC CTG CTA CTG       3408
Ser Gln Ser Glu Ser Asn Ser Phe Trp Asp Thr Ser Pro Leu Leu Leu
            1125                1130                1135

GGG AAG TCT CCG CGA GAC GAA GAC AGC TCA GAG GAG GAT TCA GAT GAG       3456
Gly Lys Ser Pro Arg Asp Glu Asp Ser Ser Glu Glu Asp Ser Asp Glu
        1140                1145                1150

TGC CGT TGT GTG AGC GGA CGC TGT GTG CCA CGG CCA GGC GGG GCG GTA       3504
Cys Arg Cys Val Ser Gly Arg Cys Val Pro Arg Pro Gly Gly Ala Val
    1155                1160                1165

TGC GAG TGT CCT GGA GGC TTT CAG CTG GAC GCC TCC CGT GCC CGC TGC       3552
Cys Glu Cys Pro Gly Gly Phe Gln Leu Asp Ala Ser Arg Ala Arg Cys
1170                1175                1180

GTG GAC ATT GAT GAG TGC CGA GAA CTG AAC CAG CGG GGA CTG CTG TGT       3600
Val Asp Ile Asp Glu Cys Arg Glu Leu Asn Gln Arg Gly Leu Leu Cys
1185                1190                1195                1200

AAG AGC GAG CGG TGC GTG AAC ACC AGT GGA TCC TTC CGC TGT GTC TGC       3648
Lys Ser Glu Arg Cys Val Asn Thr Ser Gly Ser Phe Arg Cys Val Cys
            1205                1210                1215

AAA GCT GGC TTC ACG CGC AGC CGC CCT CAC GGG CCT GCG TGC CTC AGC       3696
Lys Ala Gly Phe Thr Arg Ser Arg Pro His Gly Pro Ala Cys Leu Ser
        1220                1225                1230

GCC GCC GCT GAT GAT GCA GCC ATA GCC CAC ACC TCA GTG ATC GAT CAT       3744
Ala Ala Ala Asp Asp Ala Ala Ile Ala His Thr Ser Val Ile Asp His
    1235                1240                1245

CGA GGG TAT TTT CAC                                                   3759
Arg Gly Tyr Phe His
    1250

(2) INFORMATION FOR SEQ ID NO: 4:

(i) SEQUENCE CHARACTERISTICS:
        (A) LENGTH: 1253 amino acids
        (B) TYPE: amino acid
        (D) TOPOLOGY: linear (ii) MOLECULE TYPE: protein (xi) SEQUENCE DESCRIPTION: SEQ ID NO: 4:

Met Arg Gln Ala Gly Gly Leu Gly Leu Leu Ala Leu Leu Leu Ala
  1               5                  10                  15

Leu Leu Gly Pro Gly Gly Arg Gly Val Gly Arg Pro Gly Ser Gly Ala
                20                  25                  30

Gln Ala Gly Ala Gly Arg Trp Ala Gln Arg Phe Lys Val Val Phe Ala
            35                  40                  45

Pro Val Ile Cys Lys Arg Thr Cys Leu Lys Gly Gln Cys Arg Asp Ser
    50                  55                  60

Cys Gln Gln Gly Ser Asn Met Thr Leu Ile Gly Glu Asn Gly His Ser
65                  70                  75                  80

Thr Asp Thr Leu Thr Gly Ser Ala Phe Arg Val Val Cys Pro Leu
                85                  90                  95

Pro Cys Met Asn Gly Gly Gln Cys Ser Ser Arg Asn Gln Cys Leu Cys
```

-continued

```
            100                 105                 110
Pro Pro Asp Phe Thr Gly Arg Phe Cys Gln Val Pro Ala Ala Gly Thr
            115                 120                 125
Gly Ala Gly Thr Gly Ser Ser Gly Pro Gly Trp Pro Asp Arg Ala Met
        130                 135                 140
Ser Thr Gly Pro Leu Pro Leu Ala Pro Glu Gly Glu Ser Val Ala
145                 150                 155                 160
Ser Lys His Ala Ile Tyr Ala Val Gln Val Ile Ala Asp Pro Pro Gly
                165                 170                 175
Pro Gly Glu Gly Pro Pro Ala Gln His Ala Ala Phe Leu Val Pro Leu
            180                 185                 190
Gly Pro Gly Gln Ile Ser Ala Glu Val Gln Ala Pro Pro Val Val
        195                 200                 205
Asn Val Arg Val His His Pro Pro Glu Ala Ser Val Gln Val His Arg
210                 215                 220
Ile Glu Gly Pro Asn Ala Glu Gly Pro Ala Ser Ser Gln His Leu Leu
225                 230                 235                 240
Pro His Pro Lys Pro Pro His Pro Arg Pro Pro Thr Gln Lys Pro Leu
                245                 250                 255
Gly Arg Cys Phe Gln Asp Thr Leu Pro Lys Gln Pro Cys Gly Ser Asn
                260                 265                 270
Pro Leu Pro Gly Leu Thr Lys Gln Glu Asp Cys Cys Gly Ser Ile Gly
        275                 280                 285
Thr Ala Trp Gly Gln Ser Lys Cys His Lys Cys Pro Gln Leu Gln Tyr
        290                 295                 300
Thr Gly Val Gln Lys Pro Val Pro Val Arg Gly Glu Val Gly Ala Asp
305                 310                 315                 320
Cys Pro Gln Gly Tyr Lys Arg Leu Asn Ser Thr His Cys Gln Asp Ile
                325                 330                 335
Asn Glu Cys Ala Met Pro Gly Asn Val Cys His Gly Asp Cys Leu Asn
                340                 345                 350
Asn Pro Gly Ser Tyr Arg Cys Val Cys Pro Pro Gly His Ser Leu Gly
            355                 360                 365
Pro Leu Ala Ala Gln Cys Ile Ala Asp Lys Pro Glu Glu Lys Ser Leu
        370                 375                 380
Cys Phe Arg Leu Val Ser Thr Glu His Gln Cys Gln His Pro Leu Thr
385                 390                 395                 400
Thr Arg Leu Thr Arg Gln Leu Cys Cys Cys Ser Val Gly Lys Ala Trp
                405                 410                 415
Gly Ala Arg Cys Gln Arg Cys Pro Ala Asp Gly Thr Ala Ala Phe Lys
            420                 425                 430
Glu Ile Cys Pro Gly Trp Glu Arg Val Pro Tyr Pro His Leu Pro Pro
        435                 440                 445
Asp Ala His His Pro Gly Gly Lys Arg Leu Leu Pro Leu Pro Ala Pro
        450                 455                 460
Asp Gly Pro Pro Lys Pro Gln Gln Leu Pro Glu Ser Pro Ser Arg Ala
465                 470                 475                 480
Pro Pro Leu Glu Asp Thr Glu Glu Arg Gly Val Thr Met Asp Pro
                485                 490                 495
Pro Val Ser Glu Glu Arg Ser Val Gln Gln Ser His Pro Thr Thr Thr
            500                 505                 510
Thr Ser Pro Pro Arg Pro Tyr Pro Glu Leu Ile Ser Arg Pro Ser Pro
        515                 520                 525
```

-continued

```
Pro Thr Phe His Arg Phe Leu Pro Asp Leu Pro Pro Ser Arg Ser Ala
    530                 535                 540

Val Glu Ile Ala Pro Thr Gln Val Thr Glu Thr Asp Glu Cys Arg Leu
545                 550                 555                 560

Asn Gln Asn Ile Cys Gly His Gly Gln Cys Val Pro Gly Pro Ser Asp
                565                 570                 575

Tyr Ser Cys His Cys Asn Ala Gly Tyr Arg Ser His Pro Gln His Arg
            580                 585                 590

Tyr Cys Val Asp Val Asn Glu Cys Glu Ala Glu Pro Cys Gly Pro Gly
        595                 600                 605

Lys Gly Ile Cys Met Asn Thr Gly Gly Ser Tyr Asn Cys His Cys Asn
    610                 615                 620

Arg Gly Tyr Arg Leu His Val Gly Ala Gly Arg Ser Cys Val Asp
625                 630                 635                 640

Leu Asn Glu Cys Ala Lys Pro His Leu Cys Gly Asp Gly Gly Phe Cys
                645                 650                 655

Ile Asn Phe Pro Gly His Tyr Lys Cys Asn Cys Tyr Pro Gly Tyr Arg
            660                 665                 670

Leu Lys Ala Ser Arg Pro Pro Ile Cys Glu Asp Ile Asp Glu Cys Arg
        675                 680                 685

Asp Pro Ser Thr Cys Pro Asp Gly Lys Cys Glu Asn Lys Pro Gly Ser
    690                 695                 700

Phe Lys Cys Ile Ala Cys Gln Pro Gly Tyr Arg Ser Gln Gly Gly Gly
705                 710                 715                 720

Ala Cys Arg Asp Val Asn Glu Cys Ser Glu Gly Thr Pro Cys Ser Pro
                725                 730                 735

Gly Trp Cys Glu Asn Leu Pro Gly Ser Tyr Arg Cys Thr Cys Ala Gln
            740                 745                 750

Gly Ile Arg Thr Arg Thr Gly Arg Leu Ser Cys Ile Asp Val Asp Glu
        755                 760                 765

Cys Glu Ala Gly Lys Val Cys Gln Asp Gly Ile Cys Thr Asn Thr Pro
    770                 775                 780

Gly Ser Phe Gln Cys Gln Cys Leu Ser Gly Tyr His Leu Ser Arg Asp
785                 790                 795                 800

Arg Ser Arg Cys Glu Asp Ile Asp Glu Cys Asp Phe Pro Ala Ala Cys
                805                 810                 815

Ile Gly Gly Asp Cys Ile Asn Thr Asn Gly Ser Tyr Arg Cys Leu Cys
            820                 825                 830

Pro Leu Gly His Arg Leu Val Gly Gly Arg Lys Cys Lys Lys Asp Ile
        835                 840                 845

Asp Glu Cys Ser Gln Asp Pro Gly Leu Cys Leu Pro His Ala Cys Glu
    850                 855                 860

Asn Leu Gln Gly Ser Tyr Val Cys Val Cys Asp Glu Gly Phe Thr Leu
865                 870                 875                 880

Thr Gln Asp Gln His Gly Cys Glu Glu Val Glu Gln Pro His His Lys
                885                 890                 895

Lys Glu Cys Tyr Leu Asn Phe Asp Asp Thr Val Phe Cys Asp Ser Val
            900                 905                 910

Leu Ala Thr Asn Val Thr Gln Gln Glu Cys Cys Cys Ser Leu Gly Ala
        915                 920                 925

Gly Trp Gly Asp His Cys Glu Ile Tyr Pro Cys Pro Val Tyr Ser Ser
    930                 935                 940
```

```
Ala Glu Phe His Ser Leu Val Pro Asp Gly Lys Arg Leu His Ser Gly
945                 950                 955                 960

Gln Gln His Cys Glu Leu Cys Ile Pro Ala His Arg Asp Ile Asp Glu
            965                 970                 975

Cys Ile Leu Phe Gly Ala Glu Ile Cys Lys Glu Gly Lys Cys Val Asn
            980                 985                 990

Thr Gln Pro Gly Tyr Glu Cys Tyr Cys Lys Gln Gly Phe Tyr Tyr Asp
        995                 1000                1005

Gly Asn Leu Leu Glu Cys Val Asp Val Asp Glu Cys Leu Asp Glu Ser
    1010                1015                1020

Asn Cys Arg Asn Gly Val Cys Glu Asn Thr Arg Gly Gly Tyr Arg Cys
1025                1030                1035                1040

Ala Cys Thr Pro Pro Ala Glu Tyr Ser Pro Ala Gln Ala Gln Cys Leu
            1045                1050                1055

Ile Pro Glu Arg Trp Ser Thr Pro Gln Arg Asp Val Lys Cys Ala Gly
            1060                1065                1070

Ala Ser Glu Glu Arg Thr Ala Cys Val Trp Gly Pro Trp Ala Gly Pro
            1075                1080                1085

Ala Leu Thr Phe Asp Asp Cys Cys Cys Arg Gln Pro Arg Leu Gly Thr
            1090                1095                1100

Gln Cys Arg Pro Cys Pro Pro Arg Gly Thr Gly Ser Gln Cys Pro Thr
1105                1110                1115                1120

Ser Gln Ser Glu Ser Asn Ser Phe Trp Asp Thr Ser Pro Leu Leu Leu
            1125                1130                1135

Gly Lys Ser Pro Arg Asp Glu Asp Ser Ser Glu Glu Asp Ser Asp Glu
            1140                1145                1150

Cys Arg Cys Val Ser Gly Arg Cys Val Pro Arg Pro Gly Gly Ala Val
            1155                1160                1165

Cys Glu Cys Pro Gly Gly Phe Gln Leu Asp Ala Ser Arg Ala Arg Cys
            1170                1175                1180

Val Asp Ile Asp Glu Cys Arg Glu Leu Asn Gln Arg Gly Leu Leu Cys
1185                1190                1195                1200

Lys Ser Glu Arg Cys Val Asn Thr Ser Gly Ser Phe Arg Cys Val Cys
            1205                1210                1215

Lys Ala Gly Phe Thr Arg Ser Arg Pro His Gly Pro Ala Cys Leu Ser
            1220                1225                1230

Ala Ala Ala Asp Asp Ala Ala Ile Ala His Thr Ser Val Ile Asp His
            1235                1240                1245

Arg Gly Tyr Phe His
    1250
```

(2) INFORMATION FOR SEQ ID NO: 5:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO: 5:

```
Gly Glu Ser Val Ala Ser Lys His Ala Ile Tyr Ala Val Cys
1               5                   10
```

(2) INFORMATION FOR SEQ ID NO: 6:

(i) SEQUENCE CHARACTERISTICS:
        (A) LENGTH: 24 base pairs (B) TYPE: nucleic acid
            (C) STRANDEDNESS: single
            (D) TOPOLOGY: linear (xi) SEQUENCE DESCRIPTION: SEQ ID NO: 6:

TACCGATGCT ACCGCAGCAA TCTT                                                      24

(2) INFORMATION FOR SEQ ID NO: 7:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO: 7:

ATGCCTAAAC TCTACCAGCA CG                                                        22

(2) INFORMATION FOR SEQ ID NO: 8:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO: 8:

GAGTCACGTC ATCCATTCCA CA                                                        22

(2) INFORMATION FOR SEQ ID NO: 9:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO: 9:

CGTCCAAGTT GTGTCTTAGC AG                                                        22

(2) INFORMATION FOR SEQ ID NO: 10:

(i) SEQUENCE CHARACTERISTICS:
            (A) LENGTH: 53 amino acids
            (B) TYPE: amino acid
            (C) STRANDEDNESS: single
            (D) TOPOLOGY: linear (xi) SEQUENCE DESCRIPTION: SEQ ID NO: 10:

Gly Pro Pro Gly Pro Gln Gly Ala Thr Gly Pro Leu Gly Pro Lys Gly
1               5                   10                  15

Gln Thr Gly Glu Pro Gly Ile Ala Gly Phe Lys Gly Glu Gln Gly Pro
            20                  25                  30

Lys Gly Glu Thr Gly Pro Ala Gly Pro Gln Gly Ala Pro Gly Pro Ala
        35                  40                  45

Gly Glu Glu Gly Lys
    50

(2) INFORMATION FOR SEQ ID NO: 11:

(i) SEQUENCE CHARACTERISTICS:
            (A) LENGTH: 159 base pairs
            (B) TYPE: nucleic acid
            (C) STRANDEDNESS: single
            (D) TOPOLOGY: linear

```
        (xi) SEQUENCE DESCRIPTION: SEQ ID NO: 11:

GGCCCTCCCG GTCCTCAAGG TGCAACTGGT CCTCTGGGCC CCAAAGGTCA GACGGGTGAG        60

CCCGGCATCG CTGGCTTCAA AGGTGAACAA GGCCCCAAGG GAGAGACTGG ACCTGCTGGG       120

CCCCAGGGAG CCCCTGGCCC TGCTGGTGAA GAAGGAAAA                              159

(2) INFORMATION FOR SEQ ID NO: 12:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 16
        (D) OTHER INFORMATION: /note= "N = A or G or C or T"

(xi) SEQUENCE DESCRIPTION: SEQ ID NO: 12:

AAACGTCACA CGTGANACGT GAACGTTGCT TGCTGG                                  36

(2) INFORMATION FOR SEQ ID NO: 13:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO: 13:

TTACGTCCAC GTACACGTCT AGCAAGCAAG CA                                      32
```